US007189506B1

(12) United States Patent
Lim et al.

(10) Patent No.: US 7,189,506 B1
(45) Date of Patent: Mar. 13, 2007

(54) DNA BINDING COMPOUND-MEDIATED MOLECULAR SWITCH SYSTEM

(75) Inventors: Moon Young Lim, Redwood City, CA (US); Cynthia A. Edwards, Morgan Hill, CA (US); Kirk E. Fry, Palo Alto, CA (US); Thomas W. Bruice, Carlsbad, CA (US); Douglas B. Starr, Mountain View, CA (US); Megan E. Laurance, San Francisco, CA (US); Yan Kwok, Sunnyvale, CA (US); Albert W. Tam, San Francisco, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 0 days.

(21) Appl. No.: 09/518,297

(22) Filed: Mar. 3, 2000

Related U.S. Application Data

(60) Provisional application No. 60/154,605, filed on Sep. 17, 1999, provisional application No. 60/122,513, filed on Mar. 3, 1999.

(51) Int. Cl.
*C12Q 1/68* (2006.01)
*C07H 21/04* (2006.01)

(52) U.S. Cl. .................... 435/6; 435/7.21; 435/7.23; 435/69.1; 435/235.1; 436/501; 536/23.1; 536/23.4; 536/23.5; 536/23.6; 536/23.7

(58) Field of Classification Search .................. 435/6, 435/7.21, 7.23, 235.1, 69.1; 436/501; 424/78.08; 514/1; 536/23.1, 23.4, 23.5, 23.6, 23.7; 548/306.1, 548/312.4
See application file for complete search history.

(56) References Cited

U.S. PATENT DOCUMENTS

| | | | | |
|---|---|---|---|---|
| 5,071,773 | A | * | 12/1991 | Evans et al. ................. 436/501 |
| 5,306,619 | A | | 4/1994 | Edwards et al. |
| 5,527,690 | A | * | 6/1996 | Goldstein et al. .......... 435/69.1 |
| 5,578,444 | A | | 11/1996 | Edwards et al. |
| 5,693,463 | A | | 12/1997 | Edwards et al. |
| 5,716,780 | A | | 2/1998 | Edwards et al. |
| 5,726,014 | A | | 3/1998 | Edwards et al. |
| 5,738,990 | A | | 4/1998 | Edwards et al. |
| 5,744,131 | A | | 4/1998 | Edwards et al. |
| 5,843,653 | A | | 12/1998 | Gold et al. |
| 5,869,241 | A | | 2/1999 | Edwards et al. |
| 5,869,250 | A | | 2/1999 | Cheng et al. |
| 5,874,209 | A | | 2/1999 | Karin et al. |
| 5,912,411 | A | | 6/1999 | Bujard et al. |

FOREIGN PATENT DOCUMENTS

| | | |
|---|---|---|
| WO | WO 93/23431 | 11/1993 |
| WO | WO 94/29442 | 12/1994 |
| WO | WO 96/37609 | 11/1996 |
| WO | WO 96/41865 | 12/1996 |
| WO | WO 97/10337 | 3/1997 |
| WO | WO 98/03646 | 1/1998 |
| WO | WO 99/25856 | 5/1999 |
| WO | WO 00/09704 | 2/2000 |

OTHER PUBLICATIONS

Gottesfeld et al., Regulation of Gene Expression by Small Molecules. Nature 387, 202-205 (1997).*
Dickinson et al., Inhibition of RNA Polymerase II Transcription in Human Cells by Synthetic DNA-Binding Ligands. Proc. natl. Acad. Sci USA 95 12890-12895 (1998).*
Voet etal., Biochemistry pp. 854-856 and 868 (1990).*
Brar, D.S., et al., "Genetically Engineered Plants for Quality Improvement" *Biotechnology and Genetic Engineering Reviews 13*:167-179 (1995).
Delort, J.P., and Capecchi, M.R., "TAXI/UAS: A Molecular Switch to Control Expression of Genes In Vivo" *Human Gene Therapy* 7:809-820 (1996).
Gossen, M., et al., "Transcriptional Activation by Tetracyclines in Mammalian Cells" *Science 268*:1766-1769 (1995).
Martin, G.B., "Gene discovery for crop improvement" *Current Opinion in Biotechnology 9*:220-226 (1998).
Miller, N., and Whelan, J., "Progress in Transcriptionally Targeted and Regulatable Vectors for Genetic Therapy" *Human Gene Therapy 8*:803-815 (1997).
Moore, I., et al., "A transgenic activation system for regulated gene expression in transgenic plants" *Proc. Natl. Acad. Sci. USA 95*:376-381 (1998).
Pomerantz, J.L., et al., "Structure-Based Design of Transcription Factors" *Science 267*:93-96 (1995).
Walther, W., and Stein, U., "Cell type specific and inducible promoters for vectors in gene therapy as an approach for cell targeting" *J. Mol Med 74*:379-392 (1996).

* cited by examiner

*Primary Examiner*—Chih-Min Kam
(74) *Attorney, Agent, or Firm*—Perkins Coie LLP

(57) ABSTRACT

The present invention provides molecular switch system methods and compositions for use in regulatable gene expression. The system includes a nucleic acid construct which has a DNA response sequence for a transcriptional regulatory protein operably linked to a promoter, a compound binding sequence in the vicinity of the DNA response sequence, a transgene under the control of the promoter; and a DNA binding compound. In some cases, the molecular switch system further includes a nucleic acid sequence encoding a transcriptional regulatory protein operably linked to a second promoter. The invention further provides a method for screening compounds for the ability to function in the molecular switch system and thereby regulate gene expression.

6 Claims, 19 Drawing Sheets distal UP nnAAA(A/T)(A/T)T(A/T)TTTTnnAAAnnn proximal UP

Fig. 2A

```
-66      -59     UP element          -38
CCCCGTCAGAAAATTATTTTAAATTTCCTCTTGTCAGGCCCGAATAACTCCCTAT
AATGCGCCAC +1                                                  +50
CACTGACACGGAACAACGGCAAACACGCCGCCGGGTCAGCGGGGTTCTCCT
```

Fig. 2B

- Direct targeting
  - MEF    C(TTAAAAATAA)C    SEQ:22
  - 780BP  (TTGAAAAATCAA)CGCT    SEQ:23

- Overlapping Targeting (test for up or down-stream)
  - UL9    (ttttTGTT)CGCAC(TTtttttttt)    SEQ:24
  - NFκB   (tttttGGG[AtTTT)CCttttt)    SEQ:25
  - LacO   (aaaaAATT)GTGAGCGCTCAC(AATTtttt)  SEQ:26
  - NtBBF1 (tttACT[TTA)tttt]

Fig. 3 rrnB P1 promoter UP Sequences

| | | |
|---|---|---|
| RLG3097 (core) | GACTGCAGTGGTACCTAGGAGG | SEQ:14 |
| RLG3074 (wt) | AGAAAATTATTTTAAATTTCCT | SEQ:13 |
| RLG4192 | GGAAAATTTTTTTTCAAAAGTA | SEQ:16 |
| RLG4174 | TGAAATTTATTTTGCGAAAGGG | SEQ:17 |

Fig. 4A

```
YK 202LX  (52-mer) 5' CATGGACG CCACTG AGCCG TTTT  TGTTCGCACTT GAGGCGAGTCGATGCACC 3'
                   3' GTACCTGC GGTGAC TCGGC AAAA  ACAAGCGTGAA CTCCGCTCAGCTACGTGG 5'

YK 202RX-A (54-mer) 5' CATGGACG CCACTG AGCCG TTTTTT TGTTCGCACTT TTTTTTGAGGCGAGTCGATGCACC 3'
YK 202RX-B (54-mer) 3' GTACCTGC GGTGAC TCGGC ACAAGCGTGAA AAAAAACTCCGCTCAGCTACGTGGB 5'

YK 202LRX (58-mer) 5' CATGGACG CCACTG AGCCGTTTT TGTTCGCACTT TTTTTTGAGGCGAGTCGATGCACC 3'
                   3' GTACCTGC GGTGAC TCGGCAAAAA ACAAGCGTGAA AAAAAACTCCGCTCAGCTACGTGG 5'
```

Fig. 5

JF 101 (NFKB1) (50mer) (right side)

5' cgac cgtgctcgag TTAACGGGACTTTCCAAaaa cgatcg gact ggactc 3'
3' gctg gcacgagctc AATTGCCCTGAAAGGTTttt gctagc ctga cctgag 5'

JF 102 (NFKB2) (60mer) (right side)

5' cgac cgtgctcgag TTAACGGGAtTTTCCAAaaa cgatcg gact ggactc 3'
3' gctg gcacgagctc AATTGCCCTaAAAGGTTttt gctagc ctga cctgag 5'

JF 103 (NFKB3) (60mer) (both side)

5' cgac cgtgctcgag aaattGGGAtTTTCCAAaaa cgatcg gact ggactc 3'
3' gctg gcacgagctc tttaaCCCTaAAAGGTTttt gctagc ctga cctgag 5'

Fig. 7

```
TCAATATTGGCCATTAGCCATATTATTCATTGGTTATATAGCATAAATCAATATTGGCTATTGGC
CATTGCATACGTTGTATCTATATCATAATATGTACATTTATATTGGCTCATGTCCAATATGACCG
CCATGTTGGCATTGATTATTGACTAGTTATTAATAGTAATCAATTACGGGGTCATTAGTTCATAG
CCCATATATGGAGTTCCGCGTTACATAACTTACGGTAAATGGCCCGCCTGGCTGACCGCCCAACG
ACCCCCGCCCATTGACGTCAATAATGACGTATGTTCCCATAGTAACGCCAATAGGGACTTTCCAT
TGACGTCAATGGGTGGAGTATTTACGGTAAACTGCCCACTTGGCAGTACATCAAGTGTATCATAT
GCCAAGTCCGCCCCCTATTGACGTCAATGACGGTAAATGGCCCGCCTGGCATTATGCCCAGTACA
TGACCTTACGGGACTTTCCTACTTGGCAGTACATCTACGTATTAGTCATCGCTATTACCATGGTG
ATGCGGTTTTGGCAGTACACCAATGGGCGTGGATAGCGGTTTGACTCACGGGGATTTCCAAGTCT
CCACCCCATTGACGTCAATGGGAGTTTGTTTTGGCACCAAAATCAACGGGACTTTCCAAAATGTC
GTAACAACTGCGATCGCCCGCCCCGTTGACGCAAATGGGCGGTAGGCGTGTACGGTGGGAGGTCT
ATATAAGCAGAGCTCGTTTAGTGAACCGTCAGATCACTAGAAGCTTTATTGCGGTAGTTTATCAC
AGTTAAATTGCTAACGCAGTCAGTGCTTCTGACACAACAGTCTCGAACTTAAGCTGCAGTGACTC
TCTTAAGGTAGCCTTGCAGAAGTTGGTCGTGAGGCACTGGGCAGGTAAGTATCAAGGTTACAAGA
CAGGTTTAAGGAGACCAATAGAAACTGGGCTTGTCGAGACAGAGAAGACTCTTGCGTTTCTGATA
GGCACCTATTGGTCTTACTGACATCCACTTTGCCTTTCTCTCCACAGGTGTCCACTCCCAGTTCA
ATTACAGCTCTTAAGGCTAGAGTACTTAATACGACTCACTATAGGCTAGCCAGCTTGAAGCAAGC
CTCCTGAAAGATGGAGGCGTCGCTGCCGGCCCAGGCCGCCGAGACGGAGGAGGTGGGTCTTTTCG
TCGAAAAATACCTCCGGTCCGATGTCGCGCCGGCGGAAATTGTCGCGCTCATGCGCAACCTCAAC
AGCCTGATGGGACGCACGCGGTTTATTTACCTGGCGTTGCTGGAGGCCTGTCTCCGCGTTCCCAT
GGCCACCCGCAGCAGCGCCATATTTCGGCGGATCTATGACCACTACGCCACGGGCGTCATCCCCA
CGATCAACGTCACCGGAGAGCTGGAGCTCGTGGCCCTGCCCCCCACCCTGAACGTAACCCCCGTC
TGGGAGCTGTTGTGCCTGTGCAGCACCATGGCCGCGCGCCTGCATTGGGACTCGGCGGCCGGGG
ATCTGGGAGGACCTTCGGCCCCGATGACGTGCTGGACCTACTGACCCCCCACTACGACCGCTACA
TGCAGCTGGTGTTCGAACTGGGCCACTGTAACGTAACCGACGGACTTCTGCTCTCGGAGGAAGCC
GTCAAGCGCGTCGCCGACGCCCTAAGCGGCTGTCCCCGCGCGGGTCCGTTAGCGAGACGGACCA
CGCGGTGGCGCTGTTCAAGATAATCTGGGGCGAACTGTTTGGCGTGCAGATGGCCAAAAGCACGC
AGACGTTTCCCGGGGCGGGGCGCGTTAAAAACCTCACCAAACAGACAATCGTGGGGTTGTTGGAC
GCCCACCACATCGACCACAGCGCCTGCCGGACCCACAGGCAGCTGTACGCCCTGCTTATGGCCCA
CAAGCGGGAGTTTGCGGGCGCGCGCTTCAAGCTACGCGTGCCCGCGTGGGGGCGCTGTTTGCGCA
CGCACTCATCCAGCGCCAACCCCAACGCTGACATCATCCTGGAGGCGGCGCTGTCGGAGCTCCCC
ACCGAGGCCTGGCCCATGATGCAGGGGGCGGTGAACTTTAGCACCCTAATGAAGCTACTGTCTTC
TATCGAACAAGCATGCCCAAAAAAGAAGAGAAAGGTAGATGAATTCCCGGGGATCTCGACGGCCC
CCCCGACCGATGTCAGCCTGGGGGACGAGCTCCACTTAGACGGCGAGGACGTGGCGATGGCGCAT
GCCGACGCGCTAGACGATTTCGATCTGGACATGTTGGGGGACGGGGATTCCCCGGGTCCGGGATC
GCCAGGGATCCGTCGACTTGACGCGTTGATATCATCTAGAGCGGCCGCAGGTACCTGAATAACTA
AGGCCGCTTCCCTTTAGTGAGGGTTAATGCTTCGAGCAGACATGATAAGATACATTGATGAGTTT
GGACAAACCACAACTAGAATGCAGTGAAAAAAATGCTTTATTTGTGAAATTTGTGATGCTATTGC
TTTATTTGTAACCATTATAAGCTGCAATAAACAAGTTAACAACAACAATTGCATTCATTTATGT
TTCAGGTTCAGGGGGAGATGTGGGAGGTTTTTTAAAGCAAGTAAAACCTCTACAAATGTGGTAAA
ATCCGATAAGGATCGATTCCGGAGCCTGAATGGCGAATGGACGCGCCCTGTAGCGGCGCATTAAG
CGCGGCGGGTGTGGTGGTTACGCGCACGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAATCGGG
GGCTCCCTTTAGGGTTCCGATTTAGTGCTTTACGGCACCTCGACCCCAAAAAACTTGATTAGGGT
GATGGTTCACGTAGTGGGCCATCGCCCTGATAGACGGTTTTTCGCCCTTTGACGTTGGAGTCCAC
GTTCTTTAATAGTGGACTCTTGTTCCAAACTGGAACAACACTCAACCCTATCTCGGTCTATTCTT
TTGATTTATAAGGGATTTTGCCGATTTCGGCCTATTGGTTAAAAAATGAGCTGATTTAACAAAAA
TTTAACGCGAATTTTAACAAAATATTAACGCTTACAATTTCGCCTGTGTACCTTCTGAGGCGGAA
AGAACCAGCTGTGGAATGTGTGTCAGTTAGGGTGTGGAAAGTCCCCAGGCTCCCCAGCAGGCAGA
AGTATGCAAAGCATGCATCTCAATTAGTCAGCAACCAGGTGTGGAAAGTCCCCAGGCTCCCCAGC
AGGCAGAAGTATGCAAAGCATGCATCTCAATTAGTCAGCAACCATAGTCCCGCCCCTAACTCCGC
```

Fig. 14A

```
CCATCCCGCCCCTAACTCCGCCCAGTTCCGCCCATTCTCCGCCCCATGGCTGACTAATTTTTTTT
ATTTATGCAGAGGCCGAGGCCGCCTCGGCCTCTGAGCTATTCCAGAAGTAGTGAGGAGGCTTTTT
TGGAGGCCTAGGCTTTTGCAAAAAGCTTGATTCTTCTGACACAACAGTCTCGAACTTAAGGCTAG
AGCCACCATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCTGTCAGCG
CAGGGGCGCCCGGTTCTTTTGTCAAGACCGACCTGTCCGGTGCCCTGAATGAACTGCAGGACGA
GGCAGCGCGGCTATCGTGGCTGGCCACGACGGGCGTTCCTTGCGCAGCTGTGCTCGACGTTGTCA
CTGAAGCGGGAAGGGACTGGCTGCTATTGGGCGAAGTGCCGGGGCAGGATCTCCTGTCATCTCAC
CTTGCTCCTGCCGAGAAAGTATCCATCATGGCTGATGCAATGCGGCGGCTGCATACGCTTGATCC
GGCTACCTGCCCATTCGACCACCAAGCGAAACATCGCATCGAGCGAGCACGTACTCGGATGGAAG
CCGGTCTTGTCGATCAGGATGATCTGGACGAAGAGCATCAGGGGCTCGCGCCAGCCGAACTGTTC
GCCAGGCTCAAGGCGCGCATGCCCGACGGCGAGGATCTCGTCGTGACCCATGGCGATGCCTGCTT
GCCGAATATCATGGTGGAAAATGGCCGCTTTTCTGGATTCATCGACTGTGGCCGGCTGGGTGTGG
CGGACCGCTATCAGGACATAGCGTTGGCTACCCGTGATATTGCTGAAGAGCTTGGCGGCGAATGG
GCTGACCGCTTCCTCGTGCTTTACGGTATCGCCGCTCCCGATTCGCAGCGCATCGCCTTCTATCG
CCTTCTTGACGAGTTCTTCTGAGCGGGACTCTGGGGTTCGAAATGACCGACCAAGCGACGCCCAA
CCTGCCATCACGATGGCCGCAATAAAATATCTTTATTTTCATTACATCTGTGTGTTGGTTTTTTG
TGTGAAGATCCGCGTATGGTGCACTCTCAGTACAATCTGCTCTGATGCCGCATAGTTAAGCCAGC
CCCGACACCCGCCAACACCCGCTGACGCGCCCTGACGGGCTTGTCTGCTCCCGGCATCCGCTTAC
AGACAAGCTGTGACCGTCTCCGGGAGCTGCATGTGTCAGAGGTTTTCACCGTCATCACCGAAACG
CGCGAGACGAAAGGGCCTCGTGATACGCCTATTTTATAGGTTAATGTCATGATAATAATGGTTT
CTTAGACGTCAGGTGGCACTTTTCGGGGAAATGTGCGCGGAACCCCTATTTGTTTATTTTTCTAA
ATACATTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTGCGGCATTTTGCC
TTCCTGTTTTTGCTCACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAGTTTTCGCCCCGAAGA
ACGTTTTCCAATGATGAGCACTTTTAAAGTTCTGCTATGTGGCGCGGTATTATCCCGTATTGACG
CCGGGCAAGAGCAACTCGGTCGCCGCATACACTATTCTCAGAATGACTTGGTTGAGTACTCACCA
GTCACAGAAAAGCATCTTACGGATGGCATGACAGTAAGAGAATTATGCAGTGCTGCCATAACCAT
GAGTGATAACACTGCGGCCAACTTACTTCTGACAACGATCGGAGGACCGAAGGAGCTAACCGCTT
TTTTGCACAACATGGGGGATCATGTAACTCGCCTTGATCGTTGGGAACCGGAGCTGAATGAAGCC
ATACCAAACGACGAGCGTGACACCACGATGCCTGTAGCAATGGCAACAACGTTGCGCAAACTATT
AACTGGCGAACTACTTACTCTAGCTTCCCGGCAACAATTAATAGACTGGATGGAGGCGGATAAAG
TTGCAGGACCACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTGAGATAG
GTGCCTCACTGATTAAGCATTGGTAACTGTCAGACCAAGTTTACTCATATATACTTTAGATTGAT
TTAAAACTTCATTTTTAATTTAAAAGGATCTAGGTGAAGATCCTTTTGATAATCTCATGACCAA
AATCCCTTAACGTGAGTTTTCGTTCCACTGAGCGTCAGACCCCGTAGAAAAGATCAAAGGATCTT
CTTGAGATCCTTTTTTTCTGCGCGTAATCTGCTGCTTGCAAACAAAAAAACCACCGCTACCAGCG
GTGGTTTGTTTGCCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCAAGAACTCTGTAG
CACCGCCTACATACCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGTCGGGCTGAACGGG
GGGTTCGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAGGGGGCGGAGCCTAT
GGAAAAACGCCAGCAACGCGGCCTTTTTACGGTTCCTGGCCTTTTGCTGGCCTTTTGCTCACATG
GCTCGACAGATCT
```

Fig. 14B

```
TCAATATTGGCCATTAGCCATATTATTCATTGGTTATATAGCATAAATCAATATTGGCTATTGGC
CATTGCATACGTTGTATCTATATCATAATATGTACATTTATATTGGCTCATGTCCAATATGACCG
CCATGTTGGCATTGATTATTGACTAGTTATTAATAGTAATCAATTACGGGGTCATTAGTTCATAG
CCCATATATGGAGTTCCGCGTTACATAACTTACGGTAAATGGCCCGCCTGGCTGACCGCCCAACG
ACCCCCGCCCATTGACGTCAATAATGACGTATGTTCCCATAGTAACGCCAATAGGGACTTTCCAT
TGACGTCAATGGGTGGAGTATTTACGGTAAACTGCCCACTTGGCAGTACATCAAGTGTATCATAT
GCCAAGTCCGCCCCCTATTGACGTCAATGACGGTAAATGGCCCGCCTGGCATTATGCCCAGTACA
TGACCTTACGGGACTTTCCTACTTGGCAGTACATCTACGTATTAGTCATCGCTATTACCATGGTG
ATGCGGTTTTGGCAGTACACCAATGGGCGTGGATAGCGGTTTGACTCACGGGGATTTCCAAGTCT
CCACCCCATTGACGTCAATGGGAGTTTGTTTTGGCACCAAAATCAACGGGACTTTCCAAAATGTC
GTAACAACTGCGATCGCCCGCCCCGTTGACGCAAATGGGCGGTAGGCGTGTACGGTGGGAGGTCT
ATATAAGCAGAGCTCGTTTAGTGAACCGTCAGATCACTAGAAGCTTTATTGCGGTAGTTTATCAC
AGTTAAATTGCTAACGCAGTCAGTGCTTCTGACACAACAGTCTCGAACTTAAGCTGCAGTGACTC
TCTTAAGGTAGCCTTGCAGAAGTTGGTCGTGAGGCACTGGGCAGGTAAGTATCAAGGTTACAAGA
CAGGTTTAAGGAGACCAATAGAAACTGGGCTTGTCGAGACAGAGAAGACTCTTGCGTTTCTGATA
GGCACCTATTGGTCTTACTGACATCCACTTTGCCTTTCTCTCCACAGGTGTCCACTCCCAGTTCA
ATTACAGCTCTTAAGGCTAGAGTACTTAATACGACTCACTATAGGCTAGCCAGCTTGAAGCAAGC
CTCCTGAAAGATGGAGGCGTCGCTGCCGGCCCAGGCCGCCGAGACGGAGGAGGTGGGTCTTTTCG
TCGAAAAATACCTCCGGTCCGATGTCGCGCCGGCGGAAATTGTCGCGCTCATGCGCAACCTCAAC
AGCCTGATGGGACGCACGCGGTTTATTTACCTGGCGTTGCTGGAGGCCTGTCTCCGCGTTCCCAT
GGCCACCCGCAGCAGCGCCATATTTCGGCGGATCTATGACCACTACGCCACGGGCGTCATCCCCA
CGATCAACGTCACCGGAGAGCTGGAGCTCGTGGCCCTGCCCCCACCCTGAACGTAACCCCCGTC
TGGGAGCTGTTGTGCCTGTGCAGCACCATGGCCGCGCGCCTGCATTGGGACTCGGCGGCCGGGG
ATCTGGGAGGACCTTCGGCCCCGATGACGTGCTGGACCTACTGACCCCCACTACGACCGCTACA
TGCAGCTGGTGTTCGAACTGGGCCACTGTAACGTAACCGACGGACTTCTGCTCTCGGAGGAAGCC
GTCAAGCGCGTCGCCGACGCCCTAAGCGGCTGTCCCCGCGCGGGTCCGTTAGCGAGACGGACCA
CGCGGTGGCGCTGTTCAAGATAATCTGGGGCGAACTGTTTGGCGTGCAGATGGCCAAAAGCACGC
AGACGTTTCCCGGGGCGGGGCGCGTTAAAAACCTCACCAAACAGACAATCGTGGGGTTGTTGGAC
GCCCACCACATCGACCACAGCGCCTGCCGGACCCACAGGCAGCTGTACGCCCTGCTTATGGCCCA
CAAGCGGGAGTTTGCGGGCGCGCGCTTCAAGCTACGCGTGCCCGCGTGGGGGCGCTGTTTGCGCA
CGCACTCATCCAGCGCCAACCCCAACGCTGACATCATCCTGGAGGCGGCGCTGTCGGAGCTCCCC
ACCGAGGCCTGGCCCATGATGCAGGGGGCGGTGAACTTTAGCACCCTACCAAAAAAGAAGAGAAA
GGTAGATCGGACACTGGTGACCTTCAAGGATGTATTTGTGGACTTCACCAGGGAGGAGTGGAAGC
TGCTGGACACTGCTCAGCAGATCGTGTACAGAAATGTGATGCTGGAGAACTATAAGAACCTGGTT
TCCTTGGGTTATTGATGAGATATCATCTAGAGCGGCCGCAGGTACCTGAATAACTAAGGCCGCTT
CCCTTTAGTGAGGGTTAATGCTTCGAGCAGACATGATAAGATACATTGATGAGTTTGGACAAACC
ACAACTAGAATGCAGTGAAAAAAATGCTTTATTTGTGAAATTTGTGATGCTATTGCTTTATTTGT
AACCATTATAAGCTGCAATAAACAAGTTAACAACAACAATTGCATTCATTTTATGTTTCAGGTTC
AGGGGGAGATGTGGGAGGTTTTTTAAAGCAAGTAAAACCTCTACAAATGTGGTAAAATCCGATAA
GGATCGATTCCGGAGCCTGAATGGCGAATGGACGCGCCCTGTAGCGGCGCATTAAGCGCGGCGGG
TGTGGTGGTTACGCGCACGTGACCGCTACACTTGCCAGCGCCCTAGCGCCCGCTCCTTTCGCTTT
CTTCCCTTCCTTTCTCGCCACGTTCGCCGGCTTTCCCCGTCAAGCTCTAAATCGGGGGCTCCCTT
TAGGGTTCCGATTTAGTGCTTTACGGCACCTCGACCCCAAAAAACTTGATTAGGGTGATGGTTCA
CGTAGTGGGCCATCGCCCTGATAGACGGTTTTTCGCCCTTTGACGTTGGAGTCCACGTTCTTTAA
TAGTGGACTCTTGTTCCAAACTGGAACAACACTCAACCCTATCTCGGTCTATTCTTTTGATTTAT
AAGGGATTTGCCGATTTCGGCCTATTGGTTAAAAAATGAGCTGATTTAACAAAAATTTAACGCG
AATTTTAACAAAATATTAACGCTTACAATTTCGCCTGTGTACCTTCTGAGGCGGAAAGAACCAGC
TGTGGAATGTGTGTCAGTTAGGGTGTGGAAAGTCCCCAGGCTCCCCAGCAGGCAGAAGTATGCAA
AGCATGCATCTCAATTAGTCAGCAACCAGGTGTGGAAAGTCCCCAGGCTCCCCAGCAGGCAGAAG
TATGCAAAGCATGCATCTCAATTAGTCAGCAACCATAGTCCCGCCCCTAACTCCGCCCATCCCGC
```

Fig. 15A

```
CCCTAACTCCGCCCAGTTCCGCCCATTCTCCGCCCCATGGCTGACTAATTTTTTTATTTATGCA
GAGGCCGAGGCCGCCTCGGCCTCTGAGCTATTCCAGAAGTAGTGAGGAGGCTTTTTTGGAGGCCT
AGGCTTTTGCAAAAAGCTTGATTCTTCTGACACAACAGTCTCGAACTTAAGGCTAGAGCCACCAT
GATTGAACAAGATGGATTGCACGCAGGTTCTCCGGCCGCTTGGGTGGAGAGGCTATTCGGCTATG
ACTGGGCACAACAGACAATCGGCTGCTCTGATGCCGCCGTGTTCCGGCTGTCAGCGCAGGGGCGC
CCGGTTCTTTTTGTCAAGACCGACCTGTCCGGTGCCCTGAATGAACTGCAGGACGAGGCAGCGCG
GCTATCGTGGCTGGCCACGACGGGCGTTCCTTGCGCAGCTGTGCTCGACGTTGTCACTGAAGCGG
GAAGGGACTGGCTGCTATTGGGCGAAGTGCCGGGGCAGGATCTCCTGTCATCTCACCTTGCTCCT
GCCGAGAAAGTATCCATCATGGCTGATGCAATGCGGCGGCTGCATACGCTTGATCCGGCTACCTG
CCCATTCGACCACCAAGCGAAACATCGCATCGAGCGAGCACGTACTCGGATGGAAGCCGGTCTTG
TCGATCAGGATGATCTGGACGAAGAGCATCAGGGGCTCGCGCCAGCCGAACTGTTCGCCAGGCTC
AAGGCGCGCATGCCCGACGGCGAGGATCTCGTCGTGACCCATGGCGATGCCTGCTTGCCGAATAT
CATGGTGGAAAATGGCCGCTTTTCTGGATTCATCGACTGTGGCCGGCTGGGTGTGGCGGACCGCT
ATCAGGACATAGCGTTGGCTACCCGTGATATTGCTGAAGAGCTTGGCGGCGAATGGGCTGACCGC
TTCCTCGTGCTTTACGGTATCGCCGCTCCCGATTCGCAGCGCATCGCCTTCTATCGCCTTCTTGA
CGAGTTCTTCTGAGCGGGACTCTGGGGTTCGAAATGACCGACCAAGCGACGCCCAACCTGCCATC
ACGATGGCCGCAATAAAATATCTTTATTTTCATTACATCTGTGTGTTGGTTTTTTGTGTGAAGAT
CCGCGTATGGTGCACTCTCAGTACAATCTGCTCTGATGCCGCATAGTTAAGCCAGCCCCGACACC
CGCCAACACCCGCTGACGCGCCCTGACGGGCTTGTCTGCTCCCGGCATCCGCTTACAGACAAGCT
GTGACCGTCTCCGGGAGCTGCATGTGTCAGAGGTTTTCACCGTCATCACCGAAACGCGCGAGACG
AAAGGGCCTCGTGATACGCCTATTTTTATAGGTTAATGTCATGATAATAATGGTTTCTTAGACGT
CAGGTGGCACTTTTCGGGGAAATGTGCGCGGAACCCCTATTTGTTTATTTTTCTAAATACATTCA
AATATGTATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTGTTT
TTGCTCACCCAGAAACGCTGGTGAAAGTAAAAGATGCTGAAGATCAGTTGGGTGCACGAGTGGGT
TACATCGAACTGGATCTCAACAGCGGTAAGATCCTTGAGAGTTTTCGCCCCGAAGAACGTTTTCC
AATGATGAGCACTTTTAAAGTTCTGCTATGTGGCGCGGTATTATCCCGTATTGACGCCGGGCAAG
AGCAACTCGGTCGCCGCATACACTATTCTCAGAATGACTTGGTTGAGTACTCACCAGTCACAGAA
AAGCATCTTACGGATGGCATGACAGTAAGAGAATTATGCAGTGCTGCCATAACCATGAGTGATAA
CACTGCGGCCAACTTACTTCTGACAACGATCGGAGGACCGAAGGAGCTAACCGCTTTTTTGCACA
ACATGGGGGATCATGTAACTCGCCTTGATCGTTGGGAACCGGAGCTGAATGAAGCCATACCAAAC
GACGAGCGTGACACCACGATGCCTGTAGCAATGGCAACAACGTTGCGCAAACTATTAACTGGCGA
ACTACTTACTCTAGCTTCCCGGCAACAATTAATAGACTGGATGGAGGCGGATAAAGTTGCAGGAC
CACTTCTGCGCTCGGCCCTTCCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATCGTAGTTATCTA
CACGACGGGGAGTCAGGCAACTATGGATGAACGAAATAGACAGATCGCTGAGATAGGTGCCTCAC
TGATTAAGCATTGGTAACTGTCAGACCAAGTTTACTCATATATACTTTAGATTGATTTAAAACTT
CATTTTTAATTTAAAAGGATCTAGGTGAAGATCCTTTTTGATAATCTCATGACCAAAATCCCTTA
ACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGT
TTGCCGGATCAAGAGCTACCAACTCTTTTTCCGAAGGTAACTGGCTTCAGCAGAGCGCAGATACC
AAATACTGTCCTTCTAGTGTAGCCGTAGTTAGGCCACCACTTCAAGAACTCTGTAGCACCGCCTA
CATACCTCGCTCTGCTAATCCTGTTACCAGTGGCTGCTGCCAGTGGCGATAAGTCGTGTCTTACC
GGGTTGGACTCAAGACGATAGTTACCGGATAAGGCGCAGCGGTCGGGCTGAACGGGGGGTTCGTG
CACACAGCCCAGCTTGGAGCGAACGACCTACACCGAACTGAGATACCTACAGCGTGAGCTATGAG
AAAGCGCCACGCTTCCCGAAGGGAGAAAGGCGGACAGGTATCCGGTAAGCGGCAGGGTCGGAACA
GGAGAGCGCACGAGGGAGCTTCCAGGGGGAAACGCCTGGTATCTTTATAGTCCTGTCGGGTTTCG
CCACCTCTGACTTGAGCGTCGATTTTTGTGATGCTCGTCAGGGGGGCGGAGCCTATGGAAAAACG
CCAGCAACGCGGCCTTTTTACGGTTCCTGGCCTTTTGCTGGCCTTTTGCTCACATGGCTCGACAG
ATCT
```

Fig. 15B

DNA BINDING COMPOUND-MEDIATED MOLECULAR SWITCH SYSTEM

This application claims priority to U.S. Provisional application Ser. Nos. 60/154,605, filed Sep. 17, 1999, now abandoned, and 60/122,513, filed Mar. 3, 1999, now abandoned, both of which are expressly incorporated by reference herein.

FIELD OF THE INVENTION

The present invention relates to methods for the regulated expression of a gene using cells which comprise a molecular switch, including a transcriptional regulatory protein, a DNA response site for the transcriptional regulatory protein, and a compound binding sequence in the vicinity of the DNA response site, such that sequence-dependent binding of a compound to the compound binding sequence modulates expression of a gene operably linked thereto.

REFERENCES

Albanese et al., J Biol Chem 1995 Oct. 6;270(40):23589–97.
Antona V et al., *Cytogenet Cell Genet.* 83(1–2):90–2 (1998).
Arber et al., Cancer Res. 1997 Apr. 15;57(8):1569–74.
Ausubel, et al., *CURRENT PROTOCOLS IN MOLECULAR BIOLOGY*, John Wiley & Sons, New York, N.Y., (1989).
Ayer, D. E., et al., *Mol. Cell Biol* 16(10):5772–5781, (1996).
A-Mohammadi, S., et al., *Gene Ther* 4:993–997, (1997).
Bagai, S., and Sarkar, D. P., *FEBS Lett* 326:183–188, (1993).
Bailey PJ et al., *J Steroid Biochem Mol Biol.* 63(4–6):165–74, (1997).
Baim, S. B., et al., *Proc Natl Acad Sci USA* 88(12):5072–5076, (1991).
Baumann et al., Plant Cell. 11(3):323–34, 1999.
Beerli, R. R., et al., *Proc Natl Acad Sci USA* 95(25):14628–33, (1998).
Beier et al., Proc Natl Acad Sci USA. 1999 Feb. 16;96(4):1433–8.
Bilbao, G., et al., *FASEB J* 11(8):624–634, (1997).
Blaese, R. M., et al., *Science* 270:475–480, (1995).
Bohl, D., et al., *Nat Med* (3):299–305; 278–9, (1997).
Bohl, D., and Heard, J. M., *Hum Gene Ther* 8(2):195–204, (1997).
Bourillot et al., J Gen Virol. 1998 February;79 (Pt 2):363–70.
Brand NJ, Int J Biochem Cell Biol. 1997 December;29(12):1467–70.
Brar, D. S., et al., *Biotechnol Genet Eng Rev* 13:167–79, (1996).
Braselmann, S., et al., *Proc Natl Acad Sci USA.* 90(5):1657–1661, (1993).
Briata P, et al., FEBS Lett 402(2–3):131–5 (1997).
Busch et al., Mol Endocrinol. 1997 March;11(3):379–89.
Bremer, R. E., et al., *Chem Biol* 5(3): 119–33, (1998).
Burcin, M. M., et al., *Proc Natl Acad Sci USA* 96(2):355–60, (1999).
Bushman, F., *Science* 267:1443–1444, (1995).
Butler, M., *MAMMALIAN CELL BIOTECHNOLOGY: A PRACTICAL APPROACH*, IRL Press, (1991).
Culig, Z., et al., *Cancer Res* 54(20):5474–5478, (1994).
Delgado MD et al., FEBS Lett 444(1):5–10 (1999).
Delort, J.P., and Capecchi, M. R., *Hum Gene Ther* 7(7):809–820, (1996).
Dzau, V., Keystone Symposium Molecular and Cellular Biology of Gene Therapy, Keystone, Co. Jan. 19–25, (1998).
Egholm, M., et al., *J. Am. Chem. Soc* 114:1895–1897, (1992).
Egholm, et al., *Science* 254:1497, (1991).
Evans, et al., *HANDBOOK OF PLANT CELL CULTURES*, Vol. 1, MacMillan Publishing Co. New York, (1983).
Fisher F et al., EMBO J. 12(13):5075–82 (1993).
Fraley, et al., *Proc Natl Acad Sci USA* 79:1859–1863, (1982).
Fraley, et al., *Proc Natl Acad Sci USA* 80:4803, (1983).
From, et al., *Proc. Nat Acad Sci USA* 82:5824, (1985).
Gatz, C., et al., *R Mol Gen Genet* 227(2):229–37, (1991).
Gelvin, S. B., et al., eds. *PLANT MOLECULAR BIOLOGY MANUAL*, (1990).
Gossen, M., and Bujard, H., *Proc Natl Acad Sci* 89(12):5547–5551, (1992).
Gossen, M., et al., *Trends Biochem. Sci* 18:471–475, (1993).
Gossen, M., et al., *Science* 268(5218):1766–1769, (1995).
Greisman, H. A., and Pabo, C. O., *Science* 275(5300):657–61, (1997).
Guo, H., and Kohlhaw, G. B., *FEBS Lett* 390(2):191–195, (1996).
Hanvey, et al., *Science* 258:1481–1485, (1992).
Horsch, et al., *Science* 233:496498, (1984).
Hsiao, et al., *Proc Natl Acad Sci USA* 76:3829, (1979).
Ido, A., et al., *Cancer Res* 55(14):3105–3109, (1995).
Ikeda et al., Mol. Cell. Biol. 18(1):10–18, (1998).
Isner, J., Keystone Symposium Molecular and Cellular Biology of Gene Therapy, Keystone, Co. Jan. 19–25, (1998).
Jiang, et al., Oncogene, 8:3447–3457, 1993.
Johnstone RW et al., *Biochemistry* 37(34):11924–31 (1998).
Jones FS, Proc Natl Acad Sci USA 90(14):6557–61, 1993
Kasuga, M., et al., *Nat Biotechnol* 17(3):287–291, (1999).
Keown, et al., *Methods in Enzymology* 185:527–537 (1990).
Klein, et al., *Nature* 327:70–73, (1987).
Knudsen and Muller, *Planta* 185:330–336, (1991).
Koh, G. Y., et al., *J Clin Invest* 95(1):114–121, (1995).
Kolodziejczyk, P. P., *Adv Exp Med Biol* 464:5–20, (1999).
Krens, et al., *Nature* 296:72–74, (1982).
Larrick, J.W., *Res Immunol* 149:603–608, (1998).
Li S et al., J Biol. Chem., 274(12):7803–15 (1999).
Lu, B., and Federoff, H. J., *Hum Gene Ther* 6(4):419–428, (1995).
Ma, J. K., and Vine, N. D., *Curr Top Microbiol Immunol* 236:275–92, (1999).
Mailly F et al., Mol Cell Biol 16(10):5346–57 (1996).
Maniatis, et al., *MOLECULAR CLONING: A LABORATORY MANUAL*, 2d Edition (1989).
Mansour, et al., *Nature* 336:348–352 (1988).
Margolin, J. F., et al., *Proc NatlAcad Sci USA* 91(10):4509–13, (1994).
McBryant, S. J., et al., *J Mol Biol* 286(4):973–81, (1999).
Miller, N., et al., *Melanoma Res* 5(2):75–81, (1995).
Miller, N., and Whelan, J., *Hum. Gene Ther* 8:803–815, (1997).
Mizuno, M., et al., *Cancer Res* 50:7826–7829, (1990).
Montenay-Garestier, T., et al., *CIBA Found Symp* 158:147–157, (1991).
Moore, I., et al., *PNAS* 95:376–381, (1998).
Moosmann P et al., *Biol Chem* 378(7):669–77 (1997).
Morishita, R., et al., *Hypertension* 21:894–899, (1993).
Nagel, R., et al., *FEMS Microbiol. Lett* 67:325, (1990).
Nan X et al., *Nature* 393(6683):386–389 (1998).
No, D., et al., *Proc Natl Acad Sci USA.* 93(8):3346–3351, (1996).
Peffer, N. J., et al., *Proc. Natl. Acad. Sci. USA* 90(22):10648–10652, (1993).

Perros, M., et al., *J Virol* 69(9):5506–5515, (1995).
Pomerantz, et al., *Science* 267(5194):93–96, (1995).
Redolfi, et al., *Neth J Plant Pathol* 89:245–254, (1983).
Rehli M et al., J Immunol 162(3):1559–1565 (1999).
Ren B et al., *Genes Dev.* 13(1):125–37 (1999).
Rivera, V. M., et al., *Nat Med* 2(9):1028–1032, (1996).
Sadowski, I., et al., *Nature* 335(6190):563–564, (1988).
Salmons, B., and Gunzburg, W. H., *Hum Gene Ther*4: 129–141, (1993).
Sambrook, et al., *MOLECULAR CLONING: A LABORATORY MANUAL,* 2nd Edition, Cold
Spring Harbor Laboratory press (1989).
Satijn DP et al., Mol. Cell. Biol. 17(7):4105–4113, (1997).
Schell, J., *Science* 237:1176–1183, (1987).
Shaw, et al., *Gene* 23:315 (1983).
Seipel, K., et al., *EMBO J.* 13:4961–4968, (1992).
Smith, J. D., et al., *Proc Natl Acad Sci USA* 92(25): 11926–11930, (1995).
Smolenska, L., et al., *FEBS Lett* 441:379–382, (1998).
Soucek L, et al., Oncogene 17(19):2463–72 (1998).
Stelnicki EJ et al., Differentiation 62(1):33–41 (1997).
Takahashi T et al., Jpn J Cancer Res 89(4):347–51 (1998).
Thiel G et al., J Biol Chem 273(41):26891–9 (1998).
Tian, X. C., and Yang, X. J., *Mol Med Today* 4(10):424425, (1998).
Triezenberg, S. J., et al., *Genes Dev* 2:718–729, (1988).
Uknes, et al., *Plant Cell* 4:645–656, (1982).
Valsesia-Wittman, S., et al., *J. Virol* 68:4609–4619, (1994).
Van Loon, *Plant Mol Viol* 4:111–116, (1985).
Van Solingen, et al., *J. Bact* 130:946, (1977).
Vasil, I. R., *CELL CULTURE AND SOMATIC CELL GENETICS OF PLANTS,* ed., Acad. Press,
Orlando, Vol. I, (1984), and Vol. III, (1986).
Walther, W., and Stein, U., *J. Mol. Med* 74:379–392, (1996).
Wang, J. C., and Van Dyke, M. W., *Biochim Biophys Acta* 1218(3):308–314, (1994).
Warren, G. J., *Curr Biol* 8(15):R514–6, (1998).
White RJ et al., Science 266(5184) 448–450 (1994).
White, S., et al., *Chem Biol* 4(8):569–78, (1997).
Wingo, P. A., et al., *Cancer* 82(6):1197–1207, 1998.
Wittung, P., et al., *Nature* 368:561–563, (1994).
Wolfgang CD et al., Mol Cell Biol 17(11):6700–6707 (1997).
Wu, G. Y., et al., *J. Biol. Chem* 269:11542–11546, 1994.
Xu, Z., et al., *Bioorg Med Chem* 5(6): 113747, (1997).
Ye, X., et al., *Science* 283(5398):88–91, (1999).
Yarranton, G. T., *Curr. Opin. Biotechnol* 3:506–511, 1992.
Zazopoulos E et al., *Nature,* 390(6657):311–5, (1997).
Zhang D et al., *J Biol Chem* 273(29):18086–91 (1998).
Zipfel PF et al., Biochim Biophys Acta 1354(2): 134–144 (1997).
Cowell et al., Nucleic Acids Res. 1996 Sep. 15;24(18): 3607–1.
Deuschle et al., Mol Cell Biol. 1995 April; 15(4):1907–14.
Estrem et al., Proc Natl Acad Sci USA. 1998 Aug. 18;95 (17):9761–6.
Gansauge et al., Cancer Res. 1997 May 1;57(9):1634–7.
Hall et al., Adv Cancer Res. 1996;68:67–108.
Herber et al., Oncogene, 9(7):2105–7, 1994a.
Herber et al., Oncogene, 9(4):1295–304, 1994b.
Hinz et al. Mol Cell Biol. 19(4):2690–8, 1999.
Hunter and Pines, Cell. 1994 Nov. 18;79(4):573–82.
Jiang et al., Oncogene. 1993 December;8(12):3447–57.
Kornmann et al., J Clin Invest. 1998 Jan. 15;101(2):344–52.
Lenzmeier et al., Mol Cell Biol. 1998 February;18(2): 721–31.
Licht et al., Mol Cell Biol. 1994 June; 14(6):4057–66.
Loser et al., Biol Chem Hoppe Seyler. 1996 March;377(3): 187–93.
Matsumura et al., EMBO J. 1999 Mar. 1;18(5):1367–77.
Matsumura et al., EMBO J. 1999 Mar. 1;18(5):1367–77.
Motokura and Arnold, Genes Chromosomes Cancer. 1993 June;7(2):89–95.
Motokura et al., Nature. 1991 Apr. 11;350(6318):512–5.
Philipp et al., Mol Cell Biol. 1994 June; 14(6):4032–43.
Quelle et al., Genes Dev. 1993 August;7(8):1559–71.
Resnitzky et al., Mol Cell Biol. 1994 March; 14(3):1669–79.
Saha et al., Nature. 1993 Jun. 17;363(6430):648–52.
Sandig et al., Gene Ther. 1996 November;3(11):1002–9
Schnabell et al., Mol Cell Biol. 1996 June;16(6):2678–88.
Schwechheimer et al., Plant Mol. Biol. 1998 January;36(2): 195–204.
Sherr et al., Science. 1996 Dec. 6;274(5293):1672–7.
Shtutman et al., Proc Natl Acad Sci USA. 1999 May 11;96(10):5522–7.
Swirnoff et al., Mol Cell Biol. 1998 January;18(1):512–24.
Tetsu et al., Nature. 1999 Apr. 1;398(6726):422–6.
Tzamarias et al., Nature. 1994 Jun. 30;369(6483):758–61
Ulmasov et al., Plant Mol. Biol. 1997 November;35(4): 417–24.
Watanabe et al., J Biol. Chem. 1996 Sep. 13;271(37): 22570–7.
Watanabe et al., Mol Cell Biol. 1998 June;18(6):3212–22.
Welch et al., J Biol. Chem. 1994 Dec. 9;269(49):31051–8.
Whelan et al., J Steroid Biochem Mol. Biol. 1996 April;58 (1):3–12.
Wilde et al., EMBO J. 1992 April;11(4):1251–9.
Withers et al., Mol Cell Biol. 1991 October;11(10):4846–53.
Xiong et al., Cell. 1991 May 17;65(4):691–9.
Yan, Nakagawa et al., J Biol. Chem. 1997 Dec. 26;272(52): 33181–90.
Zhang et al., J Biol. Chem. 1997 Nov. 14;272(46):29272–80.
Zhou et al., Genes Chromosomes Cancer. 1995 August; 13(4):285–90.

BACKGROUND OF THE INVENTION

Regulated gene expression has utility in a variety of applications including the expression of recombinant proteins, modified production of various metabolites, functional studies in cell-based assays and in vivo in transgenic animals, in gene therapy vectors, and in plant expression vectors for controlled transgene expression.

Gene therapy is a fast evolving area of medical and clinical research. Gene therapy encompasses gene correction therapy and transfer of therapeutic genes and is being applied for treatment of cancer, infectious diseases, monogenic diseases, multigenic diseases, and acquired diseases.

There are an increasing number of anecdotal cases of efficacy in the use of gene therapy for the treatment of monogenic diseases, early stage tumors, and cardiovascular disease (Blaese, et al., 1995; Wingo, et al., 1998; Dzau, et al., 1998; Isner, et al., 1998). However, all of the currently utilized methods of gene transfer typically demonstrate low transfer efficiency and expression rates. As the technology is improved and high efficiency gene transfer and expression is achieved, the ability to regulate such expression on both a temporal and spatial level becomes increasingly important.

In addition, the development of plants having desired traits such as improved yield; disease resistance to fungal, bacterial, viral and other pathogens; insect resistance; improved fruit ripening characteristics; cold temperature and dehydration tolerance; increased salt and drought tolerance; improved food quality (i.e., nutritional content) and improved appearance has been the focus of agribusiness for many years. At present, the regulated expression of transgenes in plants with optimal expression of target genes in manner that does not result in harm to the plant is the focus of extensive research.

Attempts to control gene activity have been made using various inducible eukaryotic promoters, such as those responsive to heavy metal ions, heat shock or hormones. In most cases, the effect of exogenous inducers is pleiotropic, in that it induces the expression of endogenous cellular genes in addition to the target transgene. Second, many promoter systems exhibit high levels of basal activity in the non-induced state, i.e., endogenous activators often interfere with regulation of transgene expression.

Several systems for regulatable expression of genes ("gene switch" systems) have been reported in the literature. Such systems are based on modifying the activity of synthetic regulatory proteins, which bind to double stranded DNA and control the activity of a promoter for a given gene, by the use of exogenous inducers (compounds) that specifically interact with a particular synthetic regulatory protein.

In systems where an inducer interacts with a regulatory protein, the regulatory protein dictates the selection of inducer. So, the ability to choose an inducer with better pharmacological properties are limited by the selection of regulatory protein.

Methods for screening and constructing molecules, which have properties of sequence specific DNA binding and displacement of protein that is bound at flanking or adjacent sites on a DNA sequence, have been reported in co-owned U.S. Pat. Nos. 5,306,619, 5,693,463, 5,716,780, 5,726,014, 5,744,131, 5,738,990, 5,578,444, 5,869,241.

Using such methods, several classes of small molecules that interact with double-stranded DNA have been identified, and shown to preferentially recognize specific nucleotide sequences.

A need exists for the development of systems for regulatable gene expression which are controlled, inducible by compounds targeted to polynucleotides, and characterized by low toxicity and favorable pharmacokinetic properties.

SUMMARY OF THE INVENTION

The invention provides a molecular switch which employs a natural, engineered or synthetic DNA binding transcriptional regulatory protein and a compound (inducer) that interacts with double stranded DNA in the vicinity of the transcriptional regulatory protein binding site or DNA response element.

The binding of the compound to DNA affects the binding of the transcriptional regulatory protein to its DNA response element, thereby modifying the expression of a gene operably linked to the DNA response element.

More particularly, the invention provides a molecular switch which includes a first nucleic acid construct that has a DNA response sequence for a transcriptional regulatory protein operably linked to a first promoter; a compound binding sequence in the vicinity of the DNA response sequence for binding to a DNA binding compound; a transgene under the control of the first promoter; and a DNA binding compound.

In some cases, the molecular switch includes an engineered, non-native exogenous or synthetic transcriptional regulatory protein, by providing a second nucleic acid sequence having the coding sequence for a transcriptional regulatory protein operably linked to a second promoter.

The molecular switch may take the form of a single vector comprising one or more promoters, or may take the form of a two vector embodiment, wherein each vector comprises a promoter, which may be the same or different.

Promoters for use in the molecular switch may be compound inducible or constitutive promoters.

The molecular switch may provide from 1 to 12 compound binding sequences, wherein each compound binding sequence has from about 8 to 20 nucleotides.

The molecular switch may further provide from 1 to 12 tandem repeated transcriptional regulatory protein DNA response sequences.

The invention further includes a method of producing cells comprising a molecular switch for modulating gene expression, and cells produced by that method.

A method of screening DNA-binding compounds for the ability to regulate a molecular switch is also included in the invention and is based on: (i) identifying a DNA sequence to which a DNA binding compound is to bind; (ii) providing a nucleic acid construct having a DNA response sequence for a transcriptional regulatory protein and a compound binding sequence in the vicinity of the DNA response sequence; (iii) screening a plurality of candidate DNA binding compounds, by exposing each of the candidate compounds to the nucleic acid construct and identifying DNA binding compounds having the ability to bind to the compound-binding sequence.

BRIEF DESCRIPTION OF THE FIGURES

FIG. 2A shows the consensus sequence of the rrnB P1 promoter UP element which has been previously described (Estrem et al., 1998).

FIG. 2B shows the sequence of nucleotides −66 to +50 of the rrnB P1 promoter.

FIG. 3 depicts exemplary switchable promoter constructs (SEQ ID NOs:22–26 and 75, respectively) engineered to have a compound, ligand or drug binding sequence near the cis element, with the transcriptional regulatory protein DNA response element indicated as bolded and uppercase, the introduced nucleic acid sequence for compound binding indicated in lowercase and potential compound binding sequences indicated as ( ) or [ ]. In such constructs, the compound binding sequence may be introduced relative to the transcriptional regulatory protein DNA response element, in one or more locations including: (1) on either side, (2) on both sides, (3) upstream, (4) downstream, or (5) overlapping the DNA response element.

FIG. 4A depicts various oligonucleotide constructs engineered to have a compound-binding sequence, indicated as ( ) or [ ], in the vicinity of rrnB P1 promoter UP element.

Cells were incubated with or without 21x for 24 hrs and promoter activities assayed following treatment. Promoter activities are expressed as a percentage of basal promoter activity. All samples were in triplicate, the error bars represent standard errors of the mean (SEM) for three separate experiments.

FIG. 5 depicts the upper strand of various double-stranded oligonucleotides engineered to have a compound-binding sequence in the vicinity of a UL9 DNA response element, wherein the transcriptional regulatory protein DNA response element is indicated as bolded and uppercase, introduced compound binding sites are indicated in lowercase and potential compound binding sites are indicated as ( ) or [ ].

Figure 6:
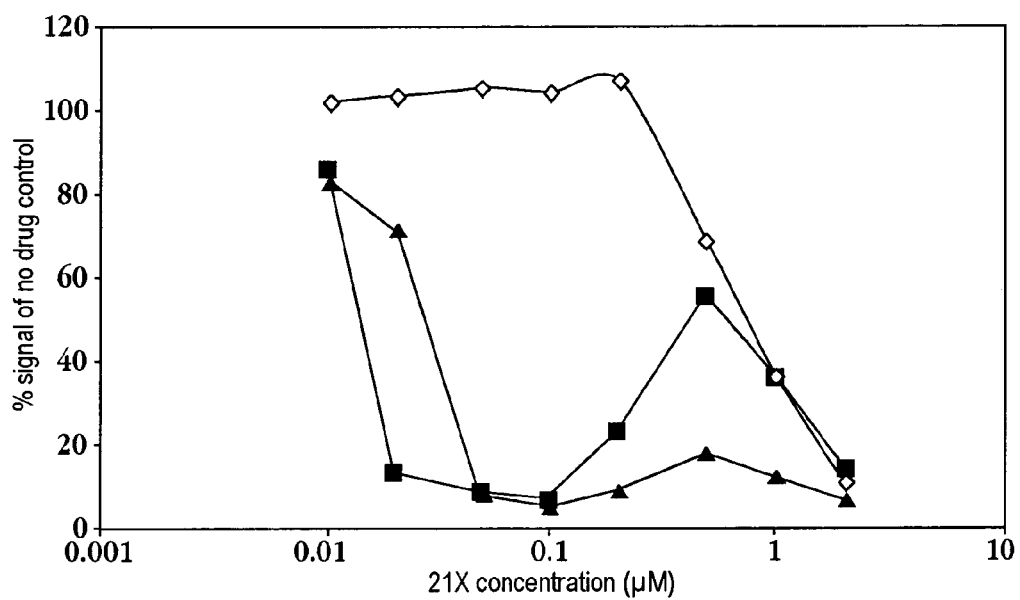

FIG. 6 depicts the results of DNA binding studies with the modified UL9 DNA response sequences presented in FIG. 5 and $^{32}$P labeled oligos, incubated with various concentrations of 21x. The modified sequences include "YK 202LX" (shown as diamonds, SEQ ID NO:18), "YK 202RX-A" (shown as squares, SEQ ID NO:19), and "YK 202RX" (shown as triangles, SEQ ID NO:21).

FIG. 7 depicts the upper strand of various double-stranded oligonucleotides engineered to have a drug-binding sequence overlapping an p50 NF-κB DNA response element, with the transcriptional regulatory protein DNA response element indicated as bolded and uppercase, introduced drug binding sites indicated in lowercase and potential drug binding sites indicated as ( ) or [ ].

Figure 8A:
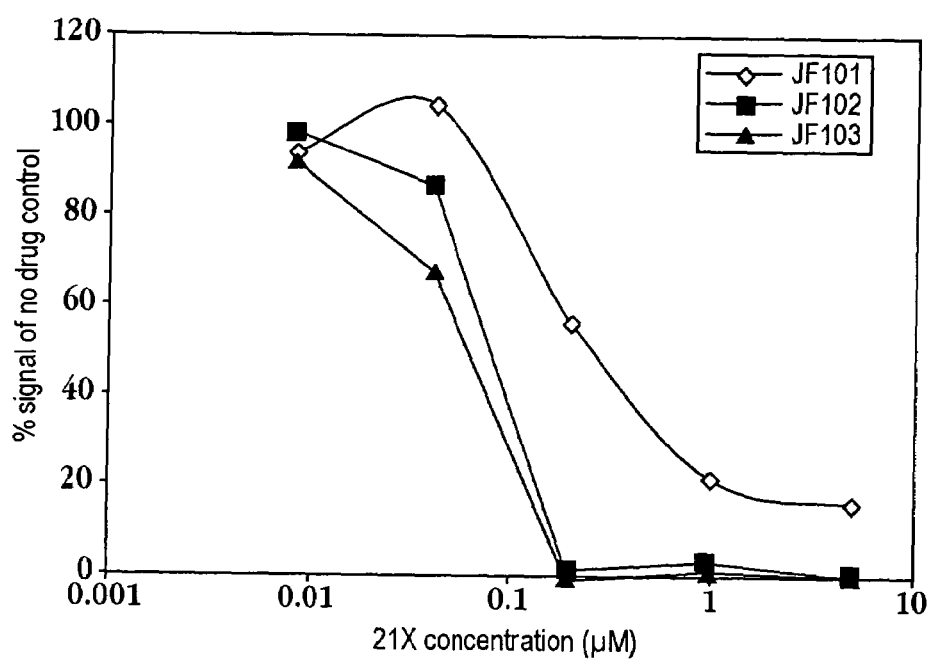

FIG. 8A depicts the results of DNA binding studies with the modified p50 NF-KB DNA response sequences of 21x. The modified sequences include "JF101" (shown as diamonds, SEQ ID NO:31), "JF102" (shown as squares, SEQ ID NO:32), and "JF3" (shown as triangles, SEQ ID NO:33).

Figure 8B:
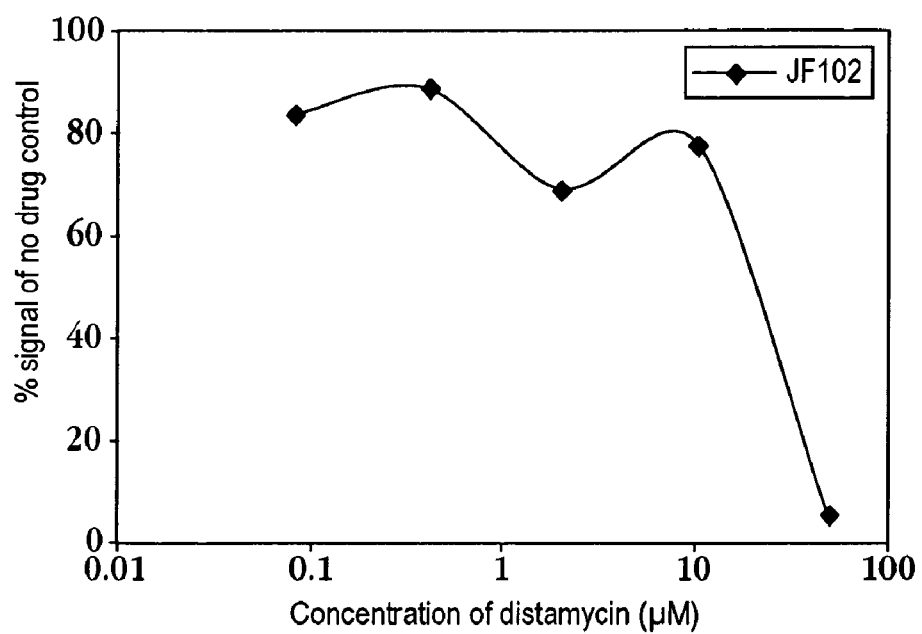

FIG. 8B depicts the results of DNA binding studies with the modified p50 NF-KB DNA response site, JF102 and $^{32}$P labeled oligonucleotides, incubated with various concentrations of distamycin.

Figure 9:
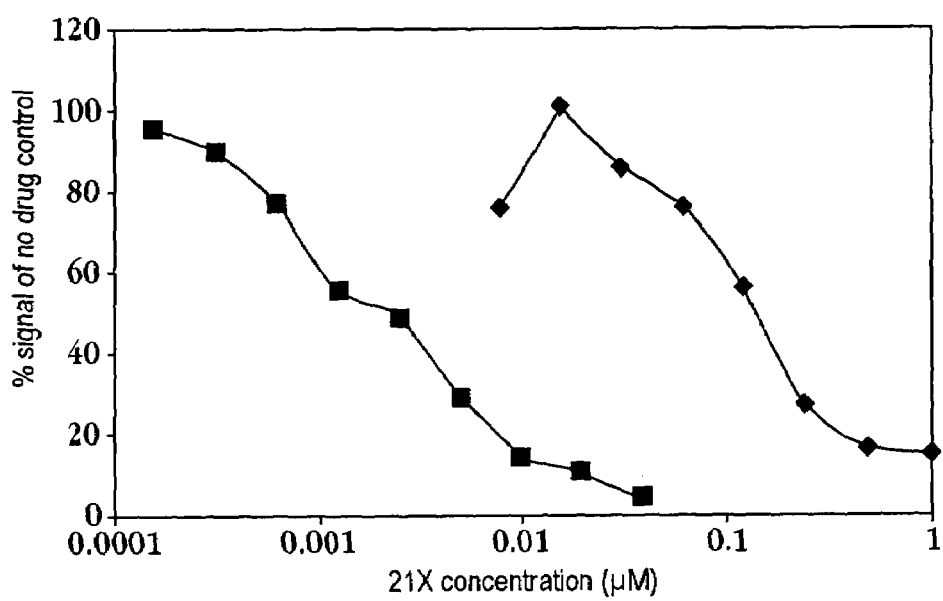

FIG. 9 depicts the results of DNA binding studies with the modified LacR DNA response sequences (lacO) and $^{32}$P labeled oligos, incubated with various concentrations of 21x. The modified sequences include the sequence presented as SEQ ID NO:34 (shown as squares) and the sequence presented as SEQ ID NO:35 (shown as diamonds).

Figure 10:
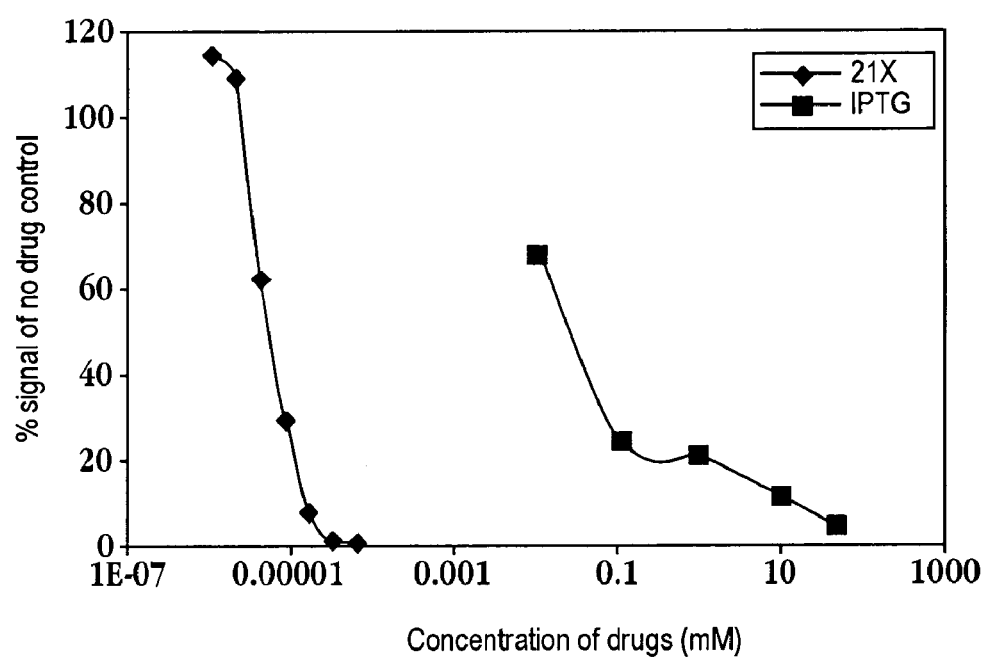

FIG. 10 depicts the results of DNA binding studies with a modified LacR DNA response sequence (SEQ ID NO:35) and $^{32}$P labeled oligos, incubated with various concentrations of 21x (shown as diamonds) or IPTG (shown as squares).

Figure 11:
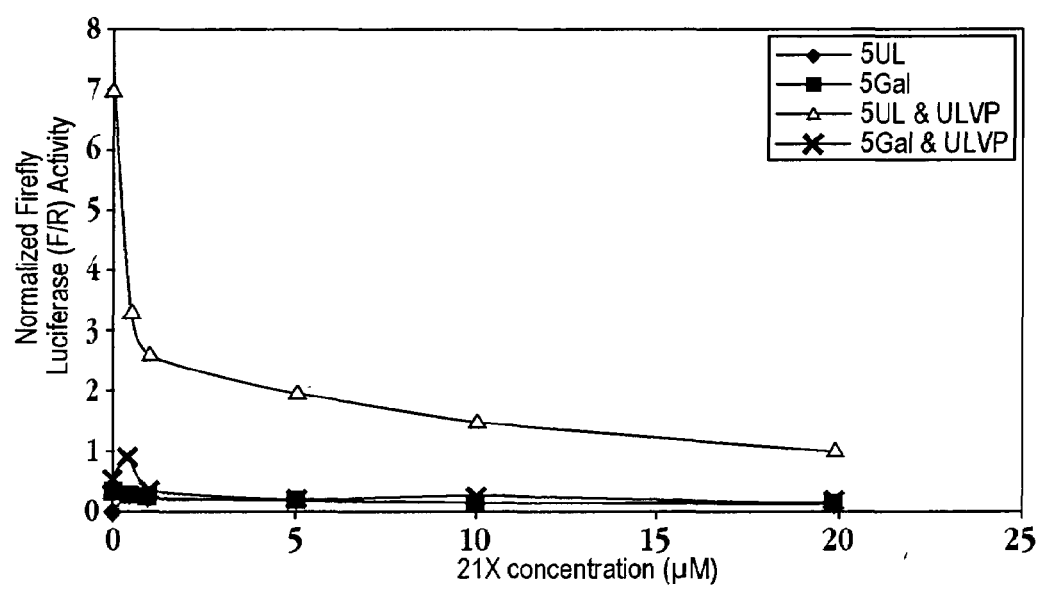

FIG. 11 depicts the effect of 21x on the activity of the chimeric activator ULVP on various promoter constructs driving firefly luciferase, transfected into MCF7 cells. Transfected cells were incubated with or without 21x for 48 hrs and promoter activities assayed at 48 hrs post-transfection. Promoter activities were normalized relative to the co-transfected internal control (pRL-NULL basal promoter) driving Renilla luciferase and expressed as a percentage of the untreated wild-type promoter construct.

Figure 12:
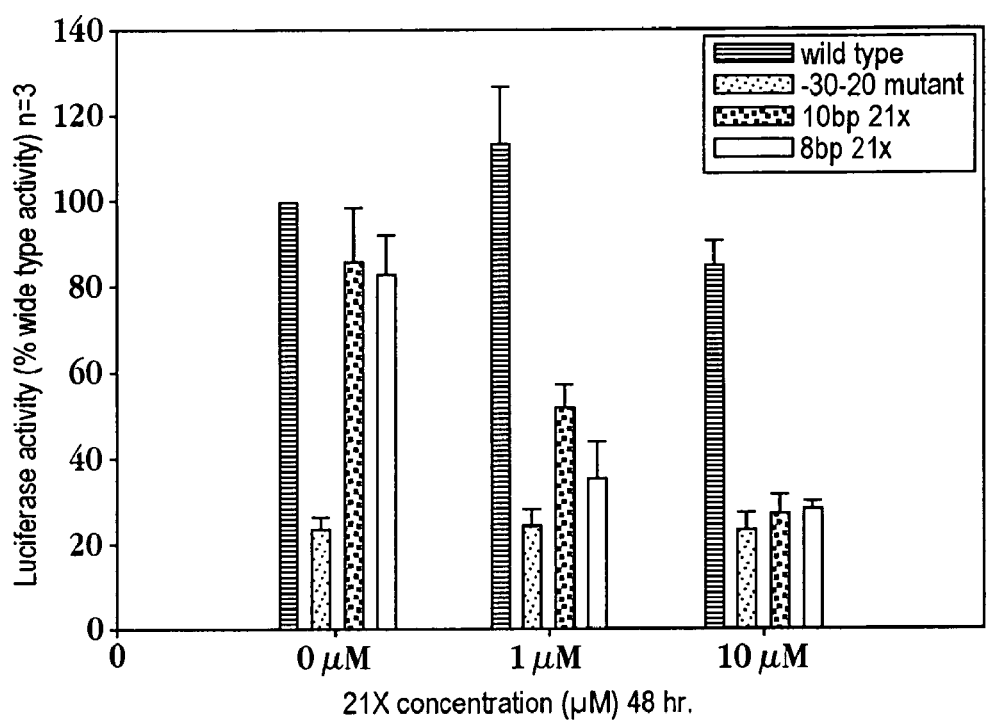

FIG. 12 depicts the effect of 21x on various cyclin D1 promoter derivatives driving firefly luciferase in pGL3 basic, transfected into MCF7 cells, as indicated on the Figure. Transfected cells were incubated with or without 21x for 48 hrs and promoter activities assayed at 48 hrs post-transfection. Promoter activities were normalized relative to the co-transfected internal control (pRL-NULL basal promoter) driving Renilla luciferase and expressed as a percentage of the untreated wild-type promoter construct. All samples were in triplicate, the error bars represent standard errors of the mean (SEM) for three separate experiments.

Figure 13:
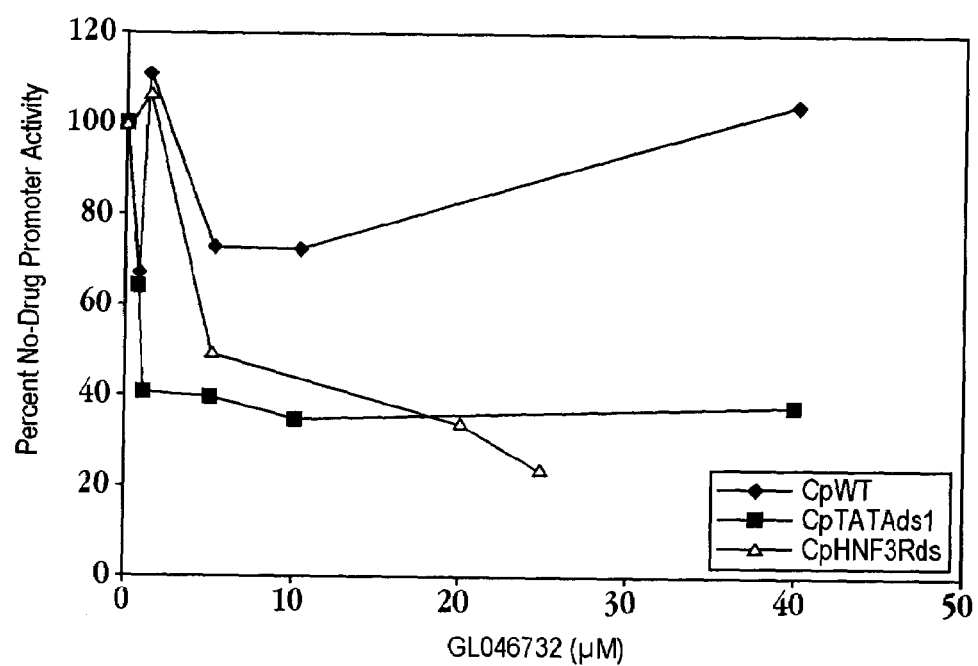

FIG. 13 depicts the dosage-dependent effect of the DNA-binding compound GL046732 on the activity of engineered HBV core promoter constructs driving firefly luciferase in pGL3 basic, in HepG2 cells, where CpWT is the core promoter wild type construct (SEQ ID NO:51), CpTA-TARds1 (SEQ ID NO:55) and CpHNF3Rds1 (SEQ ID NO:58), have ds1 sequences placed adjacent and overlapping the TATA and proximal HNF3 site, respectively.

FIGS. 14 A and B depict the sequence of the pACT ULVP activator construct construct (SEQ ID NO:61).

FIGS. 15 A and B depict the sequence of the pACT ULKRAB repressor construct (SEQ ID NO:62).

DETAILED DESCRIPTION OF THE INVENTION

I. Definitions

As used herein, a nucleic acid may be double stranded, single stranded, or contain portions of both double stranded or single stranded sequence. The depiction of a single strand also defines the sequence of the other strand and thus also includes the complement of the sequence.

As used herein, the term "recombinant nucleic acid" refers to a nucleic acid, originally formed in vitro, in general, by the manipulation of nucleic acid.

A "heterologous nucleic acid construct" has a sequence portion which is not native to the cell in which it is expressed. Heterologous, with respect to a control sequence/ coding sequence combination refers to a control sequence (i.e., promoter or enhancer) together with a coding sequence or gene, that is not found together in nature, in other words, the promoter does not regulate the expression of the same gene in the heterologous nucleic acid construct and in nature. Generally, heterologous nucleic acid sequences are not endogenous to the cell or part of the genome in which they are present, and have been added to the cell, by transfection, microinjection, electroporation, or the like. Such a heterologous nucleic acid construct may also be referred to herein as an "expression cassette".

As used herein, the term "vector" refers to a nucleic acid construct useful for transfer of the vector between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, the term "plasmid" refers to a circular double-stranded (ds) DNA construct used as a vector, and which forms an extrachromosomal self-replicating genetic element in many bacteria and some eukaryotes.

As used herein, the term "gene" means the segment of DNA involved in producing a polypeptide, which may or may not include regions preceding and following the coding region. For example, 5' untranslated (5' UTR) or "leader" sequences and 3' UTR or "trailer" sequences, as well as intervening sequences (introns) between individual coding segments (exons), may or may not be included in the DNA segment designated as the gene.

As used herein the term "transgene" refers to the portion of a heterologous nucleic acid construct, expression cassette or vector which comprises the coding sequence for a polypeptide, wherein the gene is associated with other components, i.e., the promoter with which it is not normally associated in nature.

As used herein, the term "regulatable expression system", or "molecular switch system" includes the DNA response element (site or sequence) for a transcriptional regulatory protein, a promoter, a compound-binding sequence, and a DNA binding compound. In some cases, the "regulatable expression system", or "molecular switch system" further includes an exogenously provided transcriptional regulatory protein.

As used herein, the term "DNA response element" refers to the DNA binding site or sequence for a transcriptional regulatory protein, which may be the same as, overlapping, or adjacent to, a compound-binding sequence.

As used herein, the terms "compound binding sequence", "compound binding site", "ligand binding sequence", and "ligand binding site" are used interchangeably and refer to the portion of a DNA sequence with which a compound, ligand, or molecule interacts resulting in the modified binding of a transcriptional regulatory protein to its DNA binding site (or DNA response element). In some cases the compound, ligand, or molecule may also be designated a compound or inducer. The "compound-binding sequence" or equivalent is in the vicinity of the DNA response element for transcriptional regulatory protein and may be adjacent (i.e., flanking), overlapping, or the same as the DNA binding site for a transcriptional regulatory protein.

As used herein, the term "promoter" refers to a sequence of DNA that functions to direct transcription of a gene which is operably linked thereto. The promoter will generally be appropriate to the host cell in which the target gene is being expressed. The promoter may or may not include additional control sequences (also termed "transcriptional and translational regulatory sequences"), involved in expression of a given gene product. In general, transcriptional and translational regulatory sequences include, but are not limited to, promoter sequences, ribosomal binding sites, transcriptional start and stop sequences, translational start and stop sequences, and enhancer or activator sequences. The promoter may be homologous or heterologous to the cell in which it is found.

As used herein, the terms "regulatable promoter", "inducible promoter" and "switchable promoter", are used interchangeably and refer to any promoter the activity of which is affected by a cis or trans acting factor.

As used herein, the terms "transcriptional regulatory protein", "transcriptional regulatory factor" and "transcription factor" may be used interchangeably with the term "DNA-binding protein" and refer to a cytoplasmic or nuclear protein that binds a DNA response element and thereby transcriptionally regulates the expression of an associated gene or genes. Transcriptional regulatory proteins generally bind directly to a DNA response element, however in some cases may bind indirectly to the another protein, which in turn binds to or is bound to the DNA response element.

As used herein, the term "transcriptional regulatory fusion protein" refers to a recombinant fusion protein consisting essentially of a DNA binding domain and a regulatory domain. The terms "chimeric protein" and "fusion protein" are used interchangeably herein, and refer to the transcriptional regulatory fusion proteins of the invention. It will be understood that in some cases a DNA binding protein may lack a regulatory domain and that the methods of the invention are also applicable to such transcriptional regulatory proteins.

Such a transcriptional regulatory protein may be (1) natural (native), (2) chimeric (chimera of the DNA-binding domain of a natural protein and the regulatory (activator or repressor) domain of a natural protein, (3) synthetic, having a novel DNA-binding domain designed by structural modeling, phage display screen, or other methods, and (4) may or may not take the form of a fusion protein.

As used herein, the terms "natural regulatory factor", "natural regulatory protein", "native regulatory factor", and "native regulatory protein" are used interchangeably and refer to transcriptional regulatory factors that are either broadly effective, tissue-specific, disease-specific or heterologous natural (native) factors. Such factors may be provided exogenously or may be endogenous to a particular tissue or cell type.

As used herein, the terms "synthetic regulatory factor", "synthetic regulatory protein" and "engineered regulatory factor", are used interchangeably and refer to factors that are non-native (not natural) to the host, and are provided exogenously to a cell.

As used herein, the term "operably linked" relative to a recombinant DNA construct or vector means a nucleotide component of the recombinant DNA construct or vector is in a functional relationship with another nucleotide component of the recombinant DNA construct or vector. For example, a promoter or enhancer is operably linked to a coding sequence if it affects the transcription of the coding sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

As used herein, the term "expression" refers to the process by which a polypeptide is produced based on the information contained in a given DNA sequence. The process includes both transcription and translation.

A host cell has been "transformed" by exogenous or heterologous DNA when the DNA has been introduced into the cell. Transformation may or may not result in integration (covalent incorporation) into the chromosomal DNA of the cell. For example, in eukaryotic cells such as yeast and mammalian cells, the transfected DNA may be maintained on an episomal element such as a plasmid.

As used herein, the terms "stably transformed", "stably transfected" and "transgenic" refer to cells that have a non-native (heterologous) nucleic acid sequence integrated into the genome. Stable transformation is demonstrated by the establishment of cell lines or clones comprised of a population of daughter cells containing the transfecting DNA.

In some cases "transformation" is not stable, i.e., it is transient. In the case of transient transformation, the exogenous or heterologous DNA is expressed, however, the introduced sequence is not integrated into the genome.

As used herein, the term "co-transformed" refers to a process by which two or more recombinant DNA constructs or vectors are introduced into the same cell. "Co-transformed" may also refer to a cell into which two or more recombinant DNA constructs or vectors have been introduced.

As used herein, the term "adjacent" refers to two sites on a given DNA sequence which in general are separated by less than about 20 nucleotides.

As used herein, the term "flanking compound-binding sequence" means a sequence of from about 8 to 20 nucleotides which is introduced in the vicinity of the DNA response element for a transcriptional regulatory protein. For example, a sequence of from about 8 to 20 nucleotides may be introduced, 3' and 5', respectively, of the transcriptional regulatory protein DNA response element.

As used herein, the term "sequence preferential binding" refers to the binding of a molecule to DNA in a manner which indicates a preference for binding to a certain DNA sequence relative to others.

As used herein, the term "sequence specific binding" refers to the binding of a molecule to DNA in a manner which indicates a strong binding preference for a particular DNA sequence.

As used herein, the term "sequence-dependent binding" refers to the binding of molecules to DNA in a manner that is dependent upon the target nucleotide sequence. Such binding may be "sequence-preferential" or "sequence-specific."

As used herein, the term "inhibit binding" relative to the effect of a given concentration of a particular compound on the binding of a transcriptional regulatory protein to its DNA response element refers to a decrease in the amount of binding of the transcriptional regulatory protein to its DNA response element relative to the amount of binding in the absence of the same concentration of the particular compound, and includes both a decrease in binding as well as a complete inhibition of binding.

As used herein, the term "regulate a molecular switch" refers to the ability of a DNA binding compound to bind to a nucleic acid sequence in the vicinity of the DNA response element for a transcriptional regulatory protein, thereby modifying the expression of a gene operably linked to the DNA response element.

As used herein, the terms "compound", "molecule", "ligand" and "inducer" are used interchangeably and refer to molecules or ligands characterized by sequence-preferential or sequence-specific binding to DNA at a sequence which is adjacent (i.e., flanking), overlapping, or the same as, the DNA binding site for a transcriptional regulatory protein.

As used herein, the term "dimer" refers to a compound that has two subunits, which are linked to one another and each of which may or may not have the same chemical structure. "Dimers" are a preferred embodiment for compounds used in the methods and compositions of the invention.

As used herein, the terms "modulate" and "modify" are used interchangeably and refer to a change in biological activity. Modulation may relate to an increase or a decrease in biological activity, binding characteristics, or any other biological, functional, or immunological property of the molecule.

The systems of the present invention described herein as systems for "modifying the level of expression of an exogenous gene by a DNA-binding compound", or "regulatable expression systems", are also referred to as "molecular switch systems".

As used herein, the terms "native", "natural" and "wild-type" relative to a particular nucleic acid sequence, trait or phenotype refers to the form in which that nucleic acid sequence, trait or phenotype is found in nature.

As used herein, the term "transgenic plants" refers to plants that have incorporated exogenous nucleic acid sequences, i.e., nucleic acid sequences which are not present in the native ("untransformed") plant or plant cell.

As used herein, the term "T DNA sequence" refers to a sequence derived from the $T_I$ plasmid of *Agrobacterium tumifaciens* containing the nucleic acid sequence, which is transferred to a plant cell host during infection by *Agrobacterium*.

As used herein, the term "border sequence" refers to the nucleic acid sequence, which corresponds to the left and right edges ("borders") of a T-DNA sequence.

As used herein, a "plant cell" refers to any cell derived from a plant, including undifferentiated tissue (e.g., callus) as well as plant seeds, pollen, progagules and embryos.

As used herein, the term "modified" regarding a plant trait, refers to a change in the phenotype of a transgenic plant relative to a non-transgenic plant, as it is found in nature.

As used herein, the term "in vitro" relative to the molecular switch system described herein, refers to cell-based assays carried out in vitro, including, but not limited to, binding and displacement assays and expression assays using reporter genes.

As used herein, the term "in vivo" refers to the in vivo expression of a transgene using a regulatable molecular switch, as described herein.

II. Regulatable Gene Expression/Molecular Switch Systems

A. General Considerations

An effective regulatable gene expression system for use in the methods and compositions of the invention has the following properties: (1) the ability to increase or decrease the expression of a gene of interest, (2) the ability to control the level of expression, and (3) the ability to reduce the potential toxicity of the compound used to induce expression.

B. Expression Systems Induced by Binding to Transcriptional Regulatory Proteins

Many DNA binding transcription factors are comprised of separable DNA binding and transcriptional activation domains. By interchanging DNA-binding and transcriptional activation domains from bacterial, yeast, mammalian, and viral proteins, chimeric regulatory proteins may be developed which have unique specificity and can be regulated in various host cell systems.

Several groups have successfully engineered chimeric regulatory proteins, which are generally composed of a non-mammalian DNA-binding domain and a regulatory domain of either mammalian or non-mammalian origin. A chimeric transcriptional activator with a non-mammalian DNA-binding domain allows activation of a non-mammalian response element in a mammalian system. Depending upon the level of activation required, strong viral or cellular activation domains are used.

Synthetic inducible systems utilizing both prokaryotic and eukaryotic non-mammalian DNA-binding domains have been described in the literature. The present invention makes use of various components of the synthetic inducible systems and chimeric regulatory proteins, as summarized below.

Prokaryotic inducible systems generally make use of prokaryotic repressor/operator systems such as the tet (tetR) or lac (lacI) repressor proteins. The repressor proteins contain domains that bind operator sequences specifically and domains that bind specific exogenous inducers (e.g. tetracycline for tetR and IPTG for lacI), and bind their operators in the absence of exogenous inducers that block transcription. In the presence of an exogenous inducer, the repressor binds to the inducer, changing its conformation, resulting in release of the repressor from the operator, and activation of transcription. New synthetic regulatable systems have been developed by fusing the DNA binding and inducer binding domains of these bacterial regulatory proteins to viral trans-activation domains (Baim et al., 1991; Gossen and Bujard, 1992).

The purine repressor protein, PurR, is a member of the lac repressor, LacI, family of DNA-binding proteins and binding to the operator of the pur regulon results in negative coregulation of expression. The exemplary native transcriptional regulators of PurR: purF, purFMUT, IHF, and Lef-1 provide potential binding sites for the purR protein, making them targets for regulation of the repressor using DNA-binding compounds.

Further exemplary systems include a synthetic expression system containing a modified CMV promoter with tandem repeats of tetO elements and a fusion protein consisting of a TetR DNA binding domain and a VP16 transactivator. Upon binding of tetracycline or doxycycline to the TetR protein, the chimeric TetR/VP16 protein is released from tetO elements and gene expression is down regulated (tet OFF system). Inducer mediated up-regulation of transcription has been achieved by mutating the TetR such that the mutant TetR (TetR*) binds to tetO elements in the presence of inducers such as tetracycline or doxycycline and up-regulates transcription of the transgene (tet ON system). (Gossen, et al., 1995). The TetR systems lack appropriate pharmacokinetics for rapid temporal regulation in that to reach the maximal activation in the tet ON system, the inducer needs to be cleared from the cells. Following removal, the resumption of full promoter activity takes 48 hours for tetracycline and 216 hours for doxycycline for (A-Mohammadi, et al., 1997).

Also described in the literature are similar synthetic expression systems which are responsive to hormones such as estradiol or RU486. (See, e.g., Wang, et al., 1994; Delort and Capecchi, 1996.) However, the inducers used in these systems, estradiol and RU486, are toxic or abortive.

A further type of regulatable expression system includes a DNA binding unit (ZFHD1/FKB12), and transcriptional activation unit (NF-κB p65/FRAP, Rivera, et al., 1996), expressed as separate polypeptides which come together in the presence of an exogenous inducer (rapamycin), to function as a response element specific transcriptional activator. Although the synthetic components of the chimeric transactivator are of human origin, and accordingly may be less immunogenic in humans, the inducer, rapamycin, is an immunosuppressive agent.

Non-mammalian eukaryotic elements which have also been utilized to generate chimeric regulators include the yeast *Saccharomyces cerevisiae* Gal4 DNA binding domain (Braselmann et al., 1993; Wang et al., 1994) or Leu3 (Guo and Kohlhaw, 1996) has been fused with various regulatory domains. For example, a fusion protein consisting of the Gal4 DNA binding domain, the estrogen receptor or the mutated progesterone receptor ligand binding domain and the VP16 transactivation domain may be regulated by exogenous estradiol or RU486, respectively (Whelan and Miller, 1996; Wang et al., 1994). Several variations of this basic system have been described (Whelan and Miller, 1996).

The insect hormone ecdysone inducible expression system (No et al., 1996), is based on a chimeric ecdysone receptor/VP16 fusion protein which dimerizes with the retinoid X receptor in the presence of ecdysone or its synthetic analogue, muristerone. The dimerized receptor binds the ecdysone response element and acts as transcriptional activator.

A further type of regulatable expression system includes a DNA binding domain and transcriptional activation domain expressed as separate polypeptides, and which come together in the presence of an exogenous inducer to function as a response element specific transcriptional activator. An exemplary construct includes, as a DNA binding domain, ZFHD1 (a synthetic fusion protein that contains zinc fingers 1 and 2 from Zif268, a short polypeptide linker, and the homodomain of Oct-1; Pomerantz et al., 1995), fused to the human protein FKB12, and the p65 activation domain of the human transcription factor NF-κB fused to another human protein FRAP (Rivera et al., 1996). Although the synthetic components of the chimeric transactivator are derived from human origin, and accordingly may be less immunogenic in humans, the inducer, rapamycin, is an immunosuppressive agent.

None of the aforementioned regulatable expression systems exhibit all the features of an effective regulatable gene expression system. The TetR system lacks pharmacokinetics necessary for a tightly controlled system. In addition, systems such as TetR are not applicable to agricultural applications, in that it is not practical for an inducer (i.e. tetracycline) to be sprayed on an entire field of plants.

The hormone (estradiol or RU486) and rapamycin-inducible systems suffer from toxicity problems with the specific compounds used to induce expression. Further, in the ecdysone system and the rapamycin inducible system, two chimeric proteins need to be expressed in order to make the chimeric transcription factor.

C. Expression Systems Induced by Binding to DNA

All of the aforementioned regulatable expression systems utilize compounds (inducers) that act on protein transcriptional factors. The binding of a compound or inducer to a transcriptional regulatory protein appears to change the conformation of the protein, which leads to the changes in either the DNA binding property or the dimerization property of the factors, resulting in changes in the regulatory properties of the chimeric regulator. The fact that prior art protein-inducible systems require a compound which is specific to the inducer domain of the transcriptional regulatory protein significantly limits the choice of compounds capable of functioning as inducers in a given system. Any DNA binding compound that modulates the binding of the transcriptional regulatory protein can be utilized as an inducer in the molecular switch systems of the present invention. In both switch-on and switch-off systems, described herein, the incorporation of compound-binding sequences in the vicinity of the DNA response element for a transcriptional regulatory protein permits a wide selection of compounds effective to regulate the expression of genes operably linked to such a response element. However, it will be understood that in some cases the compound-binding sequence and the DNA response element for the transcriptional regulatory compound have the same sequence.

The present invention is directed to a molecular switch system utilizing a transcriptional regulatory protein and an exogenously supplied compound, which targets nucleic acid, not protein. It has been well established through the Merlin™ technology that DNA binding compounds, when bound to double stranded DNA at sites in the vicinity of regulatory protein binding sequences, can displace the bound protein. See, e.g., U.S. Pat. Nos. 5,306,619, 5,693, 463, 5,716,780, 5,726,014, 5,744,131, 5,738,990, 5,578,444, and 5,869,241, expressly incorporated reference herein.

III. Methods and Compositions of the Invention

In the molecular switch methods and compositions of the invention, when a transcriptional regulatory protein DNA binding site is in the vicinity of (the same as, overlapping or adjacent to), a compound-binding site, the binding of the transcriptional regulatory protein may be controlled by an exogenous DNA binding compound.

A. Embodiments of the Molecular Switch System

Figure 1:
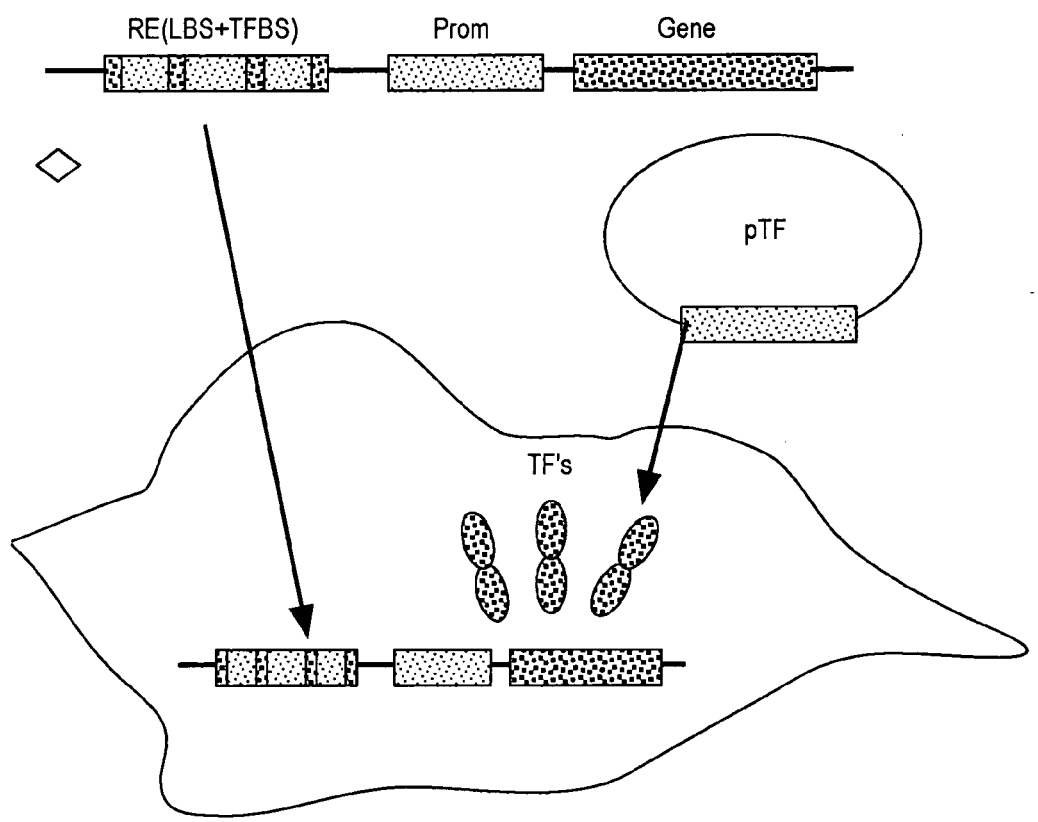
FIG. 1 is a schematic illustration of a transcriptional regulatory protein/DNA binding compound-mediated molecular switch system, wherein a transcriptional regulatory factor (TF, consisting of a transcriptional activator or repressor domain and a compound-binding domain), which may be native to a cell or provided exogenously in a plasmid (pTF), interacts with a response element (RE) comprising a ligand binding site (LBS) and a transcriptional regulatory factor binding site (TFBS). Components of the system include a transcription factor, a small molecule or ligand and a switchable promoter construct.

A number of embodiments of the molecular switch systems of the invention may be used to regulate gene expression. In its basic form, the molecular switch system includes a nucleic acid construct which has a compound-binding site in the vicinity of (the same as, overlapping or adjacent to), the DNA response site for a transcriptional regulatory protein, a DNA binding compound and a transcriptional regulatory factor (FIG. 1). Transcriptional regulatory factors or proteins for use in the molecular switch systems of the invention may be one or more of (1) endogenous, (2) exogenously supplied, (3) native, (4) synthetic (engineered), (5) chimeric, (6) effective in specific tissues or cell types, and (7) effective in a tissue or cell type independent manner.

The components of the molecular switch system of the invention may be provided to a cell by way of one or two vectors.

In one exemplary one vector embodiment of the invention, the transcriptional regulatory protein may be a native endogenous protein. In such cases, the vector comprises a synthetic DNA response element for the transcriptional regulatory protein which has a compound-binding sequence in the vicinity of the DNA response sequence and a transgene under the control of a first promoter.

In another one vector embodiment, an engineered transcriptional regulatory protein is exogenously provided to a cell in the same vector construct as a synthetic DNA response element and associated compound-binding sequence. In this aspect, the vector comprises a synthetic DNA response element for the transcriptional regulatory protein which has a compound-binding sequence in the vicinity of the DNA response sequence and a transgene under the control of a first promoter and the coding sequence for an engineered transcriptional regulatory protein under the control of a second promoter.

In still other cases, a single vector is effective to express both a transcriptional regulatory protein and a transgene under the control of a single compound-inducible promoter, utilizing IRES.

In one exemplary two vector embodiment of the invention, the first vector comprises the synthetic DNA response element for a transcriptional regulatory protein which has a compound-binding sequence in the vicinity of the DNA response element and a transgene under the control of a first promoter and the second vector comprises the coding sequence for an engineered transcriptional regulatory protein operably linked to a second promoter.

In some cases, the expression of the engineered transcriptional regulatory protein may also be regulated by a compound. In such cases, the construct has a compound-binding sequence in the vicinity of the DNA response element for a transcriptional regulatory protein and a second promoter operably linked to the coding sequence for the engineered transcriptional regulatory protein. In such cases, the first and second vectors may or may not have the same compound-binding sequence and DNA response element.

In such two vector embodiments, when the transcriptional regulatory protein is engineered, it may be an exogenously supplied native protein, it may be synthetic or chimeric, and may be effective in specific tissues or cell types, or may be effective in a tissue or cell type independent manner.

In both the one and two vector embodiments of the molecular switch system, the invention includes a compound or inducer, which when bound to a compound-binding sequence is effective to modify expression of a gene under control of the promoter.

In a chimeric activator DNA binding compound-mediated molecular switch system, the binding of a compound directly to, adjacent, or overlapping the DNA binding site for a transcriptional regulatory protein displaces the bound transcriptional regulatory protein from the DNA response element of a promoter. In such cases, the displacement of the transcriptional regulatory protein leads to down-regulation of transcription of an operably linked transgene (switch-off system).

A similar system which is switched-on by binding of a compound includes a chimeric transcriptional regulatory protein with a repressor domain instead of a transactivator domain.

Incorporation of a strong activator or repressor domain into an engineered transcriptional regulatory protein confers a wide range of activity to the regulatory protein in a regulatable gene expression construct. By incorporating promoters that function in a variety of cell types into vector constructs which have an appropriate DNA response element, expression can be achieved in the particular cell types.

In the methods of the invention, cell lines which produce a given transcriptional regulatory protein may be generated and transformed with vector constructs having a variety of compound-binding sequences. A repertoire of different regulatable expression systems may then be generated using the same basic transcriptional regulatory protein construct and DNA response element, by modifying the number of copies (repeats) of the DNA response element, and by the use of different compound-binding sequences.

In one embodiment, the system involves a natural transcriptional regulatory factor (protein) that is either tissue-specific, disease-specific or heterologous and unique to the host. Such natural or native factors may be provided exogenously or may be endogenous to a particular tissue, cell or host. In either case, such a natural DNA-binding regulatory factor will bind to a synthetic DNA response element which has been introduced into cells and has a compound-binding sequence which is the same as, overlapping, or adjacent to the DNA response element. A synthetic DNA response element for one or more natural factors may be provided to a cell.

As set forth above, in another embodiment, the system incorporates engineered regulatory proteins (activators or repressors), which are provided to cells together with a corresponding synthetic DNA response element and associated compound-binding sequence. It will be understood that the DNA sequence encoding an engineered transcriptional regulatory protein is exogenously supplied, it may be provided in the same or in a different vector construct as the synthetic DNA response element and associated compound-binding sequence. In addition, the expression of an engineered regulatory protein may be under the control of a constitutive promoter or a compound inducible promoter. When the expression of an engineered regulatory protein is under the control of a compound inducible promoter, expression may be induced by a compound which is the same as, or differs from, the compound which binds a sequence in the vicinity of the DNA response element for the regulatory protein.

Regulatable gene expression systems may be designed wherein the compound-binding sequence and the regulatory protein binding site are the same. In such cases, a native endogenous regulatory protein is used or alternatively, an exogenous, synthetic regulatory protein may be "designed" which has a DNA-binding domain which specifically binds the compound-binding sequence/transcriptional regulatory protein binding site. (See, e.g., Greisman and Pabo, 1997, which describes the selection of novel zinc three-finger proteins which bind to a specific 9 to 10 bp sequence.)

It will be understood that in some cases the DNA response element for a given transcriptional regulatory protein will include a site that also functions as the preferential binding sequence for a DNA-binding compound, i.e., a small molecule. In such cases, the DNA response element may be incorporated into the regulatable expression system of the invention in a single copy or constructs may be engineered including one or more tandem repeats of the sequence.

In other cases, the promoter sequence in the vicinity of the DNA response element will be modified to include one or more preferred binding sequences for a DNA-binding compound resulting in a regulatable promoter construct.

In one preferred embodiment, a single vector molecular switch system is employed wherein the vector contains a transgene under the control of a promoter operably linked to the DNA response element for a native transcriptional regulatory protein which has a compound binding site in the vicinity of the DNA response element. A luciferase reporter gene may be used to evaluate regulatable gene expression in vitro in cell culture. However, any reporter gene known to those of skill in the art may also be used (as further described below).

Once the ability of a compound to displace a transcriptional regulatory protein from its DNA response element has been demonstrated in a cell-based assay using a reporter construct, the genetic construct may be readily modified to include a gene of interest, such as a therapeutic gene, recombinant protein-encoding gene or drug resistance gene, in place of the reporter gene. Such modifications may be made using techniques routinely used by those of skill in the art.

In cases where the molecular switch system takes advantage of natural regulatory proteins or factors, i.e., those having tissue specificity or disease specificity, the genetic construct may deliver a therapeutic gene under control of an inducible promoter with multiple natural factor response elements flanked by compound-binding sequences without a need for an exogenous regulatory protein.

Alternatively, a natural promoter may be modified to include one or more compound binding sequences near the natural factor binding sites in the promoter, e.g., NF-KB and TFIID sites in a modified CMV promoter.

When the molecular switch system employs an exogenous transcriptional regulatory protein, the regulatory protein is supplied along with therapeutic gene, either in a single genetic construct or in separate genetic constructs.

An exogenous regulatory protein gene and a therapeutic gene may be placed under the control of the same compound-inducible promoter, and delivered by a single vector, e.g., by placing an internal ribosomal entry site in front of the synthetic activator gene. In such cases, the compound not only displaces the exogenous regulatory protein, e.g., activator, from the promoter, down-regulating the expression of the therapeutic gene, it also reduces the expression of the activator protein, providing a system with tighter regulation.

In summary, the molecular switch system provides single vector embodiments comprising one or more promoters and two vector embodiments, each comprising a promoter which may be the same or different.

Once the one or more binding sites for such an essential transcriptional regulatory protein are determined, compound binding sequence(s), e.g. for a small molecule, are engineered into the promoter near the transcriptional regulatory protein DNA response element(s) and thereby used to regulate the binding of the transcriptional regulatory protein to the promoter, resulting in regulation of promoter activity.

For example, an engineered promoter that is regulated by a DNA binding molecule can be created. In one example, a sequence comprising from about 1 to 12 or more tandem repeats of the NF-kB site with a corresponding number of compound binding sequences in the vicinity of the NF-kB site is added to a CMV minimal promoter sequence (Example 2).

Alternatively, the DNA response element for more than one type of transcriptional regulatory factor may be incorporated into a single promoter, particularly when the selected transcriptional regulatory factors work cooperatively.

In a further embodiment, a natural tissue-specific promoter is modified to include one or more introduced compound binding sequences near one or more natural transcriptional regulatory factor binding sites which are essential for transcriptional regulation of the natural tissue-specific promoter.

Temporal and spatial regulation of gene expression can be achieved by combining the tissue specificity of such a promoter with regulation of the interaction between the tissue-specific promoter and one or more essential transcriptional regulatory proteins, by the exposure of the promoter to a DNA binding compound which exhibits sequence-preferential binding to the introduced compound binding sequence(s).

A synthetic promoter may be made by introducing one or more tissue-specific transcription factor binding sites and one or more compound binding sequences into the sequence of a tissue-specific regulatable promoter such that the promoter may be regulated by a compound which preferentially binds the compound binding sequence(s), e.g., a small molecule. Such a small molecule may target an essential transcription factor or tissue specific transcription factor if it is essential to the activity of the promoter.

For example, a CMV/HBV enhancer II hybrid promoter (Sandig, et al., 1996; Loser, et al., 1996), which displays liver specificity, may be modified to have compound-binding sequences in the vicinity of (i.e., adjacent to, or overlapping), essential transcription factor binding sites, such as C/EBP, HNF-1, HNF-3 and SP-1 and/or TATA box.

In another example, tandem repeats of the myocyte-specific enhancer factor 2 (MEF2, SEQ ID NO:22) binding sequence may be fused to the sequence of a CMV minimal promoter to give muscle specificity. MEF2 sites, which are present in many muscle genes (Brand NJ, 1997), may be preferentially targeted by a small molecule such as 21x, given that the MEF2 sequence is "AT-rich".

B. Components of the Molecular Switch System

In all of the embodiments described above, the DNA response site for a transcriptional regulatory protein may contain from 1 to 12 copies of a given response sequence, with multiple copies facilitating amplification of the response. In addition, in each embodiment, natural factor and synthetic factor DNA response sites may be the same as, overlapping, or adjacent to compound-binding sequences. Accordingly, nucleic acid constructs for use in the molecular switch system of the invention may have a compound-binding sequence on one or both sides of each transcriptional regulatory protein DNA response element. Such compound-binding sequences are introduced into the DNA response element of a regulatable expression construct, allowing induction by a DNA binding compound and modulation of the activity of a promoter operably linked thereto.

It will be understood that the various components of the molecular switch systems of the invention are interchangeable. For example, a given regulatory domain may be combined with any of a number of DNA binding domains in a synthetic transcriptional regulatory protein. Similarly, any of a number of DNA response elements which bind a given transcriptional regulatory protein may be used. Many such regulatory domains, DNA binding domains and corresponding DNA response elements are known to those of skill in the art, and are summarized below. DNA binding proteins which affect transcription, but lack a regulatory domain also find utility in the methods of the invention. In general, multiple copies of a transcriptional regulatory protein may bind to its corresponding DNA response element.

Synthetic or engineered transcriptional regulatory proteins for use in the methods and compositions of the invention include a mammalian or a non-mammalian DNA binding domain and a regulatory domain of choice. Synthetic regulatory proteins can be designed by consideration of the DNA response elements for the DNA binding domain and the activity of the transcriptional regulatory protein. Activators or repressors can be used for switch-off or switch-on system, respectively.

In some cases, one or more natural transcriptional regulatory proteins may be employed in the methods and compositions of the invention to facilitate regulated gene expression, such as, homologous, heterologous, host-, tissue- or disease-specific expression. In such cases, a compound-binding sequence is inserted into a nucleic acid construct and is the same as, overlapping, or adjacent to the DNA response element(s) for the one or more natural transcriptional regulatory proteins. For example, a nucleic acid construct which has introduced compound-binding sequences in the vicinity of the TFIID and NF-κB DNA response elements in a CMV promoter.

C. Transcriptional Regulatory Proteins

In the molecular switch systems of the invention, the choice of DNA binding domain in a given transcriptional regulatory protein will determine the appropriate response element. Different DNA response elements can be utilized together with a corresponding DNA binding transcriptional regulatory protein, and need not have sequence homology to the associated compound binding sequence. The sequences of a number of DNA binding transcriptional regulatory proteins and corresponding response elements are known in the art and examples are provided in Table 1.

TABLE 1

Non-mammalian DNA binding proteins and their response elements

| DNA BINDING PROTEIN | RESPONSE ELEMENT | |
|---|---|---|
| TetR (prokaryotic) | tetO | (SEQ ID NO:5) |
| LacR (prokaryotic) | lacO | (SEQ ID NO:6) |
| GAL4 (yeast) | GAL4 | (SEQ ID NO:2) |
| Ecdysone receptor | Ecdysone | (SEQ ID NO:7) |
| ZFHD1 (mammalian) | ZFHD1 | (SEQ ID NO:3) |
| UL9 (viral) | UL9 | (SEQ ID NO:1) |

Activator and repressor protein domains which may be incorporated into engineered transcriptional regulatory proteins for use in the methods and compositions of the invention may be of mammalian, plant, Drosophila, yeast, bacterial, or viral origin, if, when linked to a DNA binding domain, the domain functions as an activator or repressor, respectively when an appropriate DNA response element is introduced into the host cells of the regulatable expression system.

In one embodiment of the regulatable expression system of the present invention, an engineered transcriptional regulatory protein is provided which includes a strong sequence specific activator, UL9–VP16, which has the C-terminal DNA binding domain of UL9 fused to the N-terminus of the activation domain of VP16 utilizing pGEX-UL9 (Genelabs) and pACT (Promega), expressed under the control of a CMV immediate early enhancer/promoter.

In another embodiment, an engineered transcriptional regulatory protein is provided which includes the UL9 C-terminal DNA binding domain fused to the N-terminus of activation domain of NF-κB p65, prepared by replacing the VP16 domain in the UL9–VP16 construct, with the activation domain of NF-κB p65 (SEQ ID NO:4).

In a further preferred embodiments, the UL9 C-terminal DNA binding domain is fused to the N-terminus of the repressor domain of kruppel protein (KRAB which is present in about one third of the vertebrate Kruppel-type zinc finger factors (Margolin JF, et al., 1994), or Mad protein (Ayer et al., 1996).

D. Activators

Polypeptides which can function to activate transcription in eukaryotic cells are well known in the art. In particular, transcriptional activation domains of many DNA binding proteins have been described and have been shown to retain their activation function when the domain is transferred to a heterologous protein. Activator domains which may be incorporated into chimeric transcriptional regulatory proteins for use in the methods and compositions of the invention, include but are not limited to VP16, NF-KB, TFE3, ITF1, Oct-1, Sp1, Oct-2, NFY-A, ITF2, c-myc, and CTF (Seipel, et al., 1992).

An exemplary polypeptide for use in a transcriptional regulatory protein of the invention is the herpes simplex virus virion protein 16, referred to herein as VP16, the amino acid sequence of which is disclosed in Triezenberg, et al., 1988. In one embodiment, amino acids from about 413489 of the C-terminus of VP16 are used as the transactivator domain (Sadowski, et al. 1988). In another embodiment, a tetramer of amino acids 437–447 of VP16 is used as the transactivator domain (Beerli, et al. 1998).

E. Repressors

Native repressors such as LacR or TetR may also be utilized in the molecular switch system of the invention. Such repressors are provided exogenously as one component of a transcriptional regulatory protein, together with a regulatable promoter which has been modified to include one or more compound-binding sequences in the vicinity of (the same as, overlapping, or adjacent to), the DNA response element for a given transcriptional regulatory protein.

Exemplary repressor proteins and their corresponding DNA binding domains for use in the methods and compositions of the invention are summarized in Table 2. The repressor domains include Kruppel (KRAB; Margolin et al., 1994), kox-1 (Deuschle et al., 1995), even-skipped (Licht et al., 1994), LacR, engrailed (Li et al, 1997), hairy (HES; Fisher et al., 1996), Groucho (TLE; Fisher et al., 1996), RING1 (Satjini et al., 1997), SSB16 and SSB24 (Saha et al., 1993), Tupl (Tzamarlas, Struhl, 1994), Nab1 (Swirnoff et al., 1998), AREB (Ikeda et al., 1998), E4BP4 (Cowell & Hurst, 1996), HoxA7 (Schnabell et al, 1996), EBNA3 (Bourillot et al., 1998), and v-erbA (Busch et al., 1997).

Further exemplary repressors for use in the methods and compositions of the invention include the basic helix-loophelix (bHLH) proteins (a family of transcription factors, which act as dimers, with their selective dimerization affecting cell proliferation, differentiation or apoptosis), such as Mxi (which is involved in repressing transcription of c-myc-responsive genes, Fisher F et al., 1993); Mnt (Soucek L, et al., 1998), Rox (Takahashi T et al., 1998), and TFEC (Rehli M et al., 1999); the homeoproteins (transcription factors known to exist in all eukaryotes where they perform important functions during development) such as Msx-1 (Stelnicki EJ et al., 1997), Evx1 (Briata P, et al., 1997) and HoxC6 (or Hox-3.3-encoded homeoprotein, Jones FS, 1993); Zn finger proteins such as CTCF (Delgado MD et al., 1999), AREB, Ikeda et al., 1998, REST (zinc finger protein RE-1-silencing transcription factor, Thiel G et al., 1998), EGR-4 (Zipfel PF et al., 1997) and KOX1 (which contains a KRAB domain, Moosmann P et al., 1997); in addition to CDP/cut (human homeodomain CCAAT displacement protein/cut homolog, Li S et al., 1999; Mailly F et al., 1996); ATF-3 (Wolfgang CD et al., 1997); MBP (Ghosh AK et al., 1999); BP1 (Berg PE et al., 1991); ERF (Day RN et al., 1998); Dr1 (White RJ et al., 1994), MeCP2 (methyl Cp-G-binidng protein; Nan X et al., 1998); ZFM1 (human zinc finger motif 1, Zhang D et al., 1998), BERF-1 (Antona V et al., 1998); PRDI-BF 1/Blimp-1 protein (Ren B et al., 1999), IFI 16 (interferon-inducible transcriptional repressor, Johnstone RW et al 1998), ICER (inducible cAMP early repressor, Bodor J et al., 1998), COUP TF (Chicken ovalbumin upstream promoter-transcription factor, Bailey PJ et al., 1997); DAX-1 (Zazopoulos E et al., 1997), ATF3 [in the activating transcription factor/cAMP responsive element binding protein (ATF/CREB) family of transcription factors, Wolfgang CD et al., 1997], and polyhomeotic protein (Ph, Satijn DP et al., 1997).

TABLE 2

Repressors with tethering DNA binding domain

| Repressor | Origin | DNA binding domain | Reference |
|---|---|---|---|
| kruppel | *Drosophila* | Gal4 | Margolin et al., 1994 |
| kox-1 | Human | TetR | Deuschle et al., 1995 |
| even-skipped | *Drosophila* | LacR | Licht et al., 1994 |
| engrailed | *Drosophila* | Qin | Li et al., 1997 |
| hairy (hes) | *Drosophila* (human) | Gal4 | Fisher et al., 1996 |
| Groucho (TLE) | *Drosophila* (human) | Gal4 | Fisher et al., 1996 |
| RING1 | *Drosophila* | LexA Gal4 | Satjin et al., 1997 |
| SSB16 SSB24 | *E. coli* | Gal4 | Saha et al., 1993 |
| Tup1 | Yeast | LexA | Tzamarlas Struhl, 1994 |
| Nab1 | Human | Gal4 | Swirnoff et al., 1998 |
| AREB | Human | Gal4 | Ikeda et al., 1998 |
| E4BP4 | Human | Gal4 | Cowell & Hurst, 1996 |
| HoxA7 | Mouse | Gal4 | Schnabell et al., 1996 |
| EBNA3 | EBV | Gal4 | Bourillot et al., 1998 |
| v-erbA | virus | Gal4 | Busch et al., 1997 |
| Mad | Mammalian | Gal4 | Ayer et al., 1996 |

F. DNA Response Elements

In the molecular switch system described herein, the DNA response element which binds the transcriptional regulatory protein may be of mammalian or non-mammalian origin and is generally present in multiple (about 1 to 12) copies, as tandem repeats.

For example, the transcriptional regulatory protein DNA response sequence may be a UL9 sequence, an NF-κB sequence or a LacR sequence which is present as 1 to 12 tandem repeats. (See Examples 1, 2 and 3.)

Preferred DNA response sequences for use in the methods and compositions of the invention are UL9, NF-κB, GALA, ZFHD1, LacR, TetR, LexA, the UP element of rrnB P1, and the ecdysone receptor binding sequence. However, it will be understood that the DNA response sequence for any known DNA-binding protein may be incorporated into the regulatable gene expression systems of the invention. Such a DNA-binding protein, may or may not contain an activator or repressor domain.

G. Promoters

The choice of promoter can significantly affect both temporal and spatial aspects of gene expression. Strong promoters with enhancers may result in a high level of expression. However, when a low level of basal activity is desired, a weak promoter may be a better choice. Expression of transgenes of interest may also be controlled at the level of transcription, by the use of cell type specific promoters or promoter elements in gene transfer vectors. Exemplary cell type specific promoters/elements and their target cell/tissue specificity are provided in Table 3. (See also, Walther and Stein, 1996; Miller and Whelan, 1997).

TABLE 3

Promoters with tissue specificity

| Gene Promoter | Target cell/tissue |
|---|---|
| *Hematopoietic cells* | |
| CD11a | Leukocytes |
| CD11b | Leukocytes |
| CD18 | Leukocytes |
| β-Globin promoter/LCR | Erythroid cells |
| Immunoglobulin promoters | B-lymphoma |
| Human parvovirus B19 | Erythroid cells |
| Scavenger receptor A | Macrophages, foam cells |
| Glycoprotein IIb | Megakaryocytes, platelets |
| γc chain | Mature myeloid cells |
| *Brain* | |
| *Liver, intestine and kidney* | |
| PEPCK | Hepatocytes |
| Albumin | Hepatocytes |
| hAAT | Hepatocytes |
| HBV | Hepatocytes |
| Fatty acid synthetase | Liver, adipose tissue |
| Factor VII | Liver |
| Carbamoyl phosphate Synthetase I | Portal vein hepatocytes |
| Na—K—Cl transporter | Small intestine Kidney |
| *Mammary gland* | |
| MMTV-LTR | Mammary carcinoma |
| WAP | Mammary carcinoma |
| β-casein | Mammary carcinoma |
| *Epithelium and endothelium* | |
| SPC | Broncheolar and alveolar epithelium |
| SP-A | Broncheolar and alveolar epithelium |
| SP-B | Broncheolar and alveolar epithelium |
| E-cadherin | Epithelium |
| Flt-1 | Endothelial cell |
| Preproendothelin | Endothelium, epithelium, muscle |
| *Keratinocytes and others* | |
| Cytokeratins | Keratinocytes |
| Transglutaminase 3 | Keratinocytes |
| Bullous pemphigoid antigen | Basal keratinocytes |
| Keratin 6 | Proliferating epidermis |
| Collagen α1 | Hepatic stellate cells skin/tendon fibroblast |
| Type X collagen | Hypertrophic chondrocytes |
| *Muscle* | |
| MCK | Undifferentiated myogenic cells |
| VLCI | Myoblasts |
| GLUT4 | Skeletal muscle |

TABLE 3-continued

Promoters with tissue specificity

| Gene Promoter | Target cell/tissue |
| --- | --- |
| Slow/fast troponins | Slow/fast twitching myofibers |
| α-actin | Smooth muscle |
| myosin heavy chain | Smooth muscle |
| | Virus infected cells |
| HIV-LTR | HIV infected Lymphocytes |
| Tat/Rev-responsive elements | HIV infected CD4+ T-cells |
| Tat-inducible element | HIV infected CD4+ T-cells |
| EBNA-1 | EBV infected cells |
| | Cancer |
| PSA | Prostate |
| Aromatase | Cancer |
| CEA | Colon and lung carcinomas |
| AFP | Hepatocellular carcinomas |
| SLPI | Carcinomas |
| Tyrosinase | Melanomas |
| Varicella Zoster virus | Melanocytes |
| c-erbB2 | Breast, pancreatic, gastric carcinomas |
| | Lung cancer |
| Myc-Max responsive element | Ras-transformed cells |
| Murine parvovirus MVMp | |
| | Pathological milieu |
| Egr-1 | Irradiated tumors |
| Grp78 | Anoxic, acidic tumors |
| MDR1 | Tumors treated with chemotherapy |
| HSP70 | Tumors treated with hyperthermy |
| VEGF | Hypoxic angiogenesis |
| Nitric oxide synthase | Hypoxic angiogenesis |
| Murine CF3 | Liver, lung inflammation |
| Serum amyloid 3 | Liver inflammation |
| Bovine keratin 6 | Hyperproliferating epithelial cells |

The promoter component of the heterologous nucleic acid constructs for use in the molecular switch systems of the invention may be a minimal or full length promoter sequence. An exemplary engineered or synthetic promoter may comprise a minimal promoter sequence fused to a cis element, such as an endogenous DNA response element for: NF-κB, myocyte-specific enhancer factor (MEF), or hepatic nuclear factor (HNF); or alternatively a bacterial sequence such as LacO, or a viral sequence such as UL9.

Preferred constitutive promoters for use in the methods and compositions of the invention include any of a number of promoters known to those of skill in the art, examples of which are a minimal CMV promoter, a CMV immediate/early enhancer promoter, an SV40 promoter, the HSV TK promoter, the MuLV LTR promoter and the HIV LTR promoter. Such promoters may be used in the native form in conjunction with natural transcriptional regulatory proteins or may be modified to include the DNA response elements for a natural or synthetic transcriptional regulatory protein.

In molecular switch systems which utilize either synthetic or natural transcriptional regulatory proteins, promoter activity may be amplified by incorporating tandem repeats of the appropriate DNA response element into the regulatable gene expression system.

Promoter activity may be further amplified by the use of an enhancer sequence, e.g., SV40, HIV or CMV enhancer sequences.

H. Compound Binding Sites

Compound-binding sequences are generally 8–20 bp in length and may be the same as, overlapping, or adjacent to the DNA response element for a transcriptional regulatory protein.

In one embodiment, the sequences are inserted next to either one or both ends of a transcriptional regulatory protein DNA response element.

In another embodiment, the compound binding sequences overlap a transcriptional regulatory protein DNA response element.

In the case of transcriptional regulatory protein response sites which consist of repeated sequence portions, the compound-binding sequence may flank each repeated sequence portion, or may flank the entire transcriptional regulatory protein response site.

In both repressor- and activator-mediated systems, incorporating compound-binding sequences in the vicinity of the DNA response element for a given transcriptional regulatory protein permits a wide selection of inducers.

Typically, binding of a DNA-binding compound to a compound-binding sequence interferes with the binding of a transcriptional regulatory protein to its corresponding DNA response element. However, the binding of some DNA-binding compounds to such DNA response elements may have the opposite effect, causing increased binding of the transcriptional regulator, i.e., activator, under conditions effective to result in expression of a transgene operably linked thereto.

In addition, each embodiment set forth above further includes one or more compound binding sequences in the vicinity of the DNA response element, as exemplified by an 8 to 20 or more bp "AT-rich" sequence which is the preferred binding preferred binding sequence for the netropsin dimer, designated 21x.

I. Transgenes

When evaluating the affect of the molecular switch system on transcription in cell based in vitro screening assays, selection of the reporter gene, determines the assay format. For example, luciferase activity can be measured by biochemical reaction with lysates from transfected cells followed by using a luminometer. If the green fluorescence protein is used as reporter, cells can be directly monitored for their fluorescence without biochemical assay, and transformed cells can be separated easily by FACS, which facilitates faster selection and enrichment of transformed cells compared to conventional methods which involve antibiotic selection.

Preferred reporter genes for use in the methods and compositions of the invention include, luciferase, green fluorescent protein (GFP), blue fluorescent protein (BFP), CAT, β-galactosidase, human growth hormone, alkaline phosphatase, etc., under the control of an appropriate promoter.

In nucleic acid constructs for use in cell-based reporter assays using the molecular switch system set forth above, the DNA response element for the transcriptional regulatory protein has from 1 to 12 copies of the DNA response element for the transcriptional regulatory protein, together with a promoter and a reporter gene, e.g., luciferase.

In one exemplary embodiment, a luciferase reporter construct with a series of tandem repeated UL9 binding sites and flanking compound-binding sequences is made by modification of the pG5luc vector (Promega). In this construct, the firefly luciferase is under the control of a synthetic promoter that is composed of five tandem repeats of the GAL4 binding site followed by the site for the major late minimal promoter of adenovirus. For use in the methods of the present invention, the Gal4 binding sites in the vector are replaced with 1 to 12 copies of the UL9 binding site, flanked by 21x binding sequences.

IV. Introduction of Nucleic Acid Constructs into Cells

A nucleic acid construct for use in the molecular switch system of the invention is introduced into either eukaryotic or prokaryotic cells. In the case of engineered, synthetic and heterologous native transcriptional regulatory proteins, a vector encoding the protein is introduced into a host cell, wherein the nucleic acid is in a form suitable for expression of the protein in that host cell. For example, a recombinant expression vector of the invention, encoding the protein, is introduced into a host cell.

A "host cell" includes any cell or cell line which is not incompatible with the protein to be expressed, the selection system chosen or the fermentation system employed. Host cells for use in the molecular switch systems of the invention include human cells, other non-human mammalian cells, yeast, bacteria, insect cells, plant cells, archea, fungi, etc.

In addition to cell lines, the invention is applicable to normal cells in vitro, ex vivo and in vivo, such as cells to be modified for gene therapy purposes, embryonic cells modified to create a transgenic or homologous recombinant animal, and plant cells.

Methods known in the art for delivery of nucleic acid constructs into mammalian cells include viral methods using adenoviral vectors, retroviral vectors, or adeno-associated viral vectors; non-viral methods using plasmids, liposomes, or other vehicles; and physical or chemical methods using calcium phosphate transfection or gene gun techniques.

Similarly, methods known in the art for delivery of a nucleic acid construct into plant cells include bacterial vectors such as the *Agrobacterium* Ti vector, and viral vectors such as the tomato mosaic virus and potato X virus.

In addition, baculovirus vectors may be used to deliver a nucleic acid construct into insect cells, and bacteria may be transformed with plasmids, and phage such as lambda phage.

For example, vectors encoding transcriptional regulatory proteins can be introduced into a host cell by standard techniques for transfecting cells. The term "transfecting" or "transfection" is intended to encompass all conventional techniques for introducing a nucleic acid construct into a host cell, including calcium phosphate co-precipitation, DEAE-dextran-mediated transfection, lipofection, electroporation and microinjection. Suitable methods for transfecting cells can be found e.g., in Sambrook, et al., 1989, expressly incorporated by reference herein.

The number of host cells transformed with a nucleic acid construct of the invention will depend, at least in part, upon the type of recombinant expression vector used and the type of transfection technique used. Nucleic acid can be introduced into a host cell transiently, or more typically, for long term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is introduced into the host cells along with the nucleic acid of interest, and the transfected cells are cultured in medium containing the appropriate drug. Preferred selectable markers include neomycin, zeomycin and hygromycin.

In some cases, two separate plasmids may be used to deliver a transcription factor and a transgene into a cell; one or both of which are under the control of regulatable or constitutive promoters. In such cases, the same compound may be used to regulate the expression of both the transcriptional regulatory protein and the transgene, which may result in feedback regulation.

In an exemplary embodiment of the method of the invention, HeLa, COS, MCF7 or HepG2 cells are transfected with an expression vector encoding a synthetic transcriptional activator protein under conditions effective to generate transformants which express the transcriptional activator. Expression of the activator is monitored by Western blot or Northern.

Once transformants expressing the transcriptional regulatory protein have been generated, they are transfected with vector constructs having different numbers of UL9 DNA binding sites, and co-transfected with a copy control, e.g., a *Renilla* luciferase plasmid.

In some cases, cells are co-transfected with plasmids containing: (1) nucleic acid sequences for expression of an engineered transcriptional regulatory protein, (2) nucleic acid sequences which have various different numbers of transcriptional regulatory protein DNA binding sites, and (3) nucleic acid sequences which serve as a copy number control at the same time.

The luciferase activity of transformants is measured and constructs selected which have an operable number of UL9 binding sites selected, i.e., constructs which give detectable luciferase activity are selected. Molecular switch constructs for use in the methods and compositions of the invention are generated by adding compound-binding sequences in the vicinity of the DNA response element for the transcriptional regulatory protein to constructs having an operable number of DNA response elements for the transcriptional regulatory protein.

Transformants that express a transcriptional regulatory protein are transfected with promoter constructs which have a response site and a copy control reporter plasmid, followed by treatment with different amounts of appropriate compounds. The effect of the compound on reporter (e.g., luciferase) activity is then determined. In most cases, the initial assay is done with transiently transfected cells. In such cases, double stable transformants are made later and the activity is verified.

Reporter constructs are used to identify and optimize operable nucleic acid constructs for use in the molecular switch systems of the invention. Once the components of the system have been engineered and tested in the context of reporter constructs, the reporter is generally replace by a transgene which encodes a protein or polypeptide of interest.

It will be understood that following engineering, optimization and testing, the components of the molecular switch system are then transferred to vectors appropriate to the application, e.g. gene therapy vectors or vectors for expression in plant cells.

V. Compounds (Inducers)

Small molecules are desirable as therapeutics for several reasons related to compound delivery: (i) they are commonly less than 10K molecular weight; (ii) they are more likely to be permeable to cells; (iii) they may be less susceptible to degradation by cellular mechanisms; and, (iv) they are not as apt to elicit an immune response. Many pharmaceutical companies have extensive libraries of chemical and/or biological mixtures, often fungal, bacterial, or algal extracts, that would be desirable to screen with the assay of the present invention.

Compounds for use in the regulatable gene expression systems of the invention may be small molecules; biological or synthetic organic compounds; peptides, oligonucleotides (and derivatives thereof); or even inorganic compounds (i.e., cisplatin).

Several classes of small molecules that interact with double-stranded DNA have been identified. Although the sequence binding preferences of most known DNA binding molecules have not, to date, been identified, several small DNA-binding molecules have been shown to preferentially recognize specific nucleotide sequences. In most cases, the DNA binding activity of a candidate compound is first evaluated in a pre-screening assay. In other cases, a compound with a known or predicted sequence binding preference is directly incorporated in the molecular switch system of the invention.

Preferred compounds for use in the molecular switch system of the invention include, but are not limited to dimers or multimers of known DNA-binding compounds, peptide nucleic acids (PNAs), polyamides, various triplex forming DNA-binding compounds, and derivatives thereof.

PNAs are compounds that are analogous to oligonucleotides, but differ in composition. In PNAs, the deoxyribose backbone of oligonucleotide is replaced by a peptide backbone. (See, e.g., Hanvey et al., 1992; Egholm, M. et al., 1992; Peffer, N. J. et al., 1993; Wittung, P. et al., 1994).

Exemplary polyamides include N-methylpyrrole and N-methylimidazole amino acids which act as synthetic DNA ligands that bind to predetermined sequences in the minor groove of DNA. (See, e.g., McBryant SJ et al., 1999; Bremer RE et al., 1998; and White S et al., 1997.)

Exemplary triplex forming DNA-binding compounds include the aromatic diamidine, DAPI (4',6-diamidino-2-phenylindole), which can induce the formation of an RNA-DNA hybrid triplex (Xu Z et al., 1997); homopyrimidine PNAs which have been shown to bind complementary DNA or RNA forming $(PNA)_2$/DNA(RNA) triplexes (Egholm et al., 1991); nucleic acid analogs such as methylphosphonates and phosphorothioates (Miller, et al., U.S. Pat. No. 4,757,055, issued Jul. 19, 1988); and other small intercalating agents coupled to oligonucleotides have been described (Montenay-Garestier T., et al., 1991).

Although exemplary classes of compounds are described herein, it will be understood that any compound effective to bind to a sequence in the vicinity of the DNA response sequence for a transcriptional regulatory protein and thereby modify the binding of a transcriptional regulatory protein to its corresponding DNA response sequence finds utility in the molecular switch system of the invention.

Pre-selected compounds may be initially identified as monomers, however, such monomers may be modified or dimerized for use in the regulatable gene expression systems of the invention.

Once identified, a DNA binding compound may be modified to improve any of a number of properties, including binding affinity, transcriptional regulatory protein displacement activity, solubility, pharmacokinetics, side effects or toxicity and production cost.

Compounds for use in the molecular switch system of the invention are characterized by sequence-specific or sequence-preferential binding, binding affinity, and the ability to modify the binding of a transcriptional regulatory protein to its corresponding response element.

By way of example, a compound designated "21x" has been identified which binds to an 8 to 10 base pair stretch of AT rich double stranded DNA. 21x is a dimer of Netropsin, which is known to bind to the minor groove of DNA, and accordingly was predicted to interact with double stranded DNA through minor groove contacts.

An additional exemplary compound, GL046732, has been identified which has two linked netropsin moieties and similar binding properties to 21x.

DNA footprinting results indicate that 21x binds to the TATA box region of the IL-1 promoter region, confirming the preferential binding of 21x to AT rich sequences of DNA.

Protein displacement data indicate that when preferred 21x sequences are introduced into the DNA response sequence for UL9, NF-kB and LacR, displacement of the transcriptional regulatory protein results. (See FIGS. 6, 8A–B and 10.)

In some cases, compounds which preferentially bind to "GC-rich" sequences will be used in the molecular switch systems of the invention together with any of a number of appropriate transcriptional regulatory proteins and their DNA response sequences, e.g., chromomycin (Lenzmeier et al, 1998; Welch et al, 1994).

VI. Exemplary Systems for Regulated Gene Expression

UL9-Based Systems for Regulated Gene Expression

Chimeric transcriptional regulatory constructs containing the UL9 DNA response element were constructed. In one example, the strong sequence specific chimeric activator, UL9–VP16, was constructed with the C-terminal DNA binding domain of UL9 fused to the N-terminus of the activation domain of VP16 and expressed under the control of a CMV immediate early enhancer/promoter. Luciferase reporter constructs with a series of tandem repeated UL9 binding sites and flanking compound-binding sites were made by modifying a commercially available vector (Example 1).

When exemplary modified promoters are operably linked to the UL9 DNA response element and a reporter gene, such as firefly luciferase in a promoter test vector, e.g., pGL3-basic (Promega), expression of the reporter gene may be measured in the presence or absence of a DNA binding molecule. An introduced "AT-rich" sequence results in preferential binding of a DNA binding molecule, such as 21x to the modified promoter, affecting the binding of UL9–VP16 to the UL9 DNA response element, resulting in down-regulation of transcription.

The effect of the exogenously provided chimeric activator UL9–VP16 ("ULVP") on expression of four different engineered reporter constructs in HeLa cells was evaluated. Low concentrations of pULVP encoding the UL9–VP16 activator significantly increased the expression of specific reporter constructs that have UL9 response elements while non-specific reporter constructs were not activated significantly (Example 1, Table 4). The results showed specific activation of expression by the ULVP activator promoter construct together with UL9 response elements.

The effect of an exemplary compound, 21x, on different engineered reporter constructs in MCF7 cells was also evaluated. The results suggest that reporter expression in the presence of chimeric activator ULVP was down-regulated with 21x treatment (7 fold at 20 μM 21x) and that the observed down-regulation was concentration dependent.

Regulated Gene Expression Using a Native Transcriptional Regulatory Protein and Modifications Thereof In one example, NF-kB and TFIID sites of the CMV immediate early promoter are targeted with 21x or another DNA-binding compound (Example 2).

The enhancer/promoter region of the CMV immediate early promoter contains multiple cellular transcription factor binding sites, including 6×SPI, 4×CRE/ATF, 4×NF-kB, and 2×AP1. Targeting a transcriptional regulatory protein to such DNA response elements which are modified to include compound-binding sequences may provide a means to modulate the activity of the promoter. Given that NF-kB is implicated as an important transcription activator for the CMV promoter which is widely used in gene therapy field, oligonucleotides were constructed based on the NF-kB DNA response sequence of the CMV promoter in order to determine if the molecular switch system described herein could be used to regulate CMV promoter the expression of genes under the control of the CMV promoter.

As detailed in Example 2, gel mobility shift assays used to detect protein displacement indicated that (1) 21x can efficiently displace p50 NF-κB at concentrations as low as 1 µM, (2) the displacement is more efficient when the NF-κB binding sequence is an IL-6 sequence (SEQ ID NO:30) relative to an IgK sequence (SEQ ID NO:29), and (3) 21x displaces NF-κB more efficiently than distamycin. These results suggest that the exemplary molecular switch system which utilizes 21x and NF-κB has broad applicability to gene therapy.

The expression of exemplary modified CMV promoters operably linked to a reporter gene, such as firefly luciferase in a promoter test vector, e.g., pGL3-basic (Promega) was measured in the presence and absence of the DNA binding molecule, 21x. The results show that an introduced "AT-rich" sequence resulted in preferential binding of a DNA binding molecule, such as 21x to the modified promoter, affecting the binding of NF-kB and TFIID to the transcriptional regulatory protein DNA response element, resulting in down-regulation of transcription.

A series of purely engineered NF-kB/TATA binding protein (TBP) based 21x ligand switchable constructs were created having 0, 2 and 4 tandem repeats of a response element consisting of the NF-kB response sequence flanked by 21x sites fused to a CMV minimal promoter with the TBP site modified to include a 9 A/T stretch to optimize 21x binding. These promoters were cloned into pGL3-Basic to create firefly luciferase reporter constructs, and reporter activity evaluated as detailed in Example 2.

LacR

The feasibility of using LacR as an exogenous factor for a switch-on molecular switch system was evaluated using LacR, which is a repressor that represses transcription of the lac operon by binding to lacO operator sequences. Binding and displacement of LacR was tested using oligonucleotides with introduced drug binding sites that overlap the transcriptional regulatory protein binding site (FIG. 9).

A gel mobility shift assay was carried out as described above for UL9, and the results of the assay indicate that: (1) 21x can efficiently displace LacR, and that (2) 21x appears to displace LacR more efficiently when the oligo JF107 was used, as further described in Example 3.

Regulation of Prokaryotic Gene Expression

The *E. coli* promoter rrnB P1 (SEQ ID NO:12), was selected as a prokaryotic model promoter for evaluating the use of 21X in the molecular switch systems of the invention, and confirming its utility in engineered switchable promoter systems.

In *Escherichia coli*, ribosome synthesis is limited by the rate of synthesis of ribosomal RNA (rRNA), which increases with growth rate. Multiple mechanisms contribute to the transcription and regulation of the rrnB P1 promoter. These include interactions with the alpha and sigma subunits of RNA polymerase. Transcriptional control involves the UP element, and core promoter.

The (−38) to (−59) region of the promoter functions as the binding site for the a subunit of RNA polymerase (RNAP, Ross et al., 1993). This AT-rich recognition element or "UP element" is responsible for the strong activity of rrnB P1 promoter, which is 30 fold greater than activity of the promoter without the UP element. The consensus sequence of the UP element has been previously described (Estrem et al., 1998) and is shown in FIG. 2A (SEQ ID NO:13).

The rrnB P1 promoter UP element is composed of two sub sites, (proximal and distal), both of which are implicated in binding of the promoter to the a subunit of RNAP. The wild type UP element of rrnB P1, which contains a 17 base pair stretch of AT-rich sequences, was used to test the affect of various compounds which preferably bind to AT-rich sequences.

The affect of 21x on the interaction of the a subunit of RNAP with the rrnB P1 UP element was evaluated based on the transcriptional activity of the promoter. The sequence of nucleotides −66 to +50 of the rrnB P1 promoter is shown in FIG. 2B (SEQ ID NO:12).

Several *E. coli* strains carrying various rrnB P1 promoters fused to a lacZ reporter on its chromosome, were tested as a phage mono-lysogen, as detailed in Example 4.

Each of the promoters described above has intact RNAP a binding consensus sequences in the −35 and −10 regions of the promoter.

Components of bacterial cell-based assay systems for evaluation of regulated expression using the molecular switch include:
(1) a recombinant promoter construct including a reporter gene, such as *Renilla* luciferase or β-galactosidase;
(2) a recombinant DNA response sequence which has transcription factor binding sites, such as RNA polymerase sigma and RNA polymerase alpha with drug binding sequences in the vicinity thereof; and
(3) a small molecule (compound) designed to bind in the vicinity of the DNA response element.

In such an assay system, gene expression is measured as a function of compound concentration using wild type and engineered promoters and may include both plasmid and chromosomal DNA.

An exemplary assay is described in Example 4, below. The results indicate that the 21x effect is concentration dependent up to 10 µM. The observed effect was not altered by targeting both sites of the UP element, relative to targeting the distal site of the UP element alone. The differences in the magnitude of the down-regulating effect of 21x suggest that the 21x binding sequence can be optimized in engineered promoters.

Such targeting studies suggest that a strong promoter like rrnB P1, and engineered variants thereof, can be down-regulated with a sequence preferential DNA-binding compound when the engineered promoter contains a compound binding sequence in the vicinity of the transcriptional regulatory protein DNA response element.

Regulated Gene Expression Using the Cyclin D1 Promoter

Mammalian cyclin D1 (CCND1, also named PRAD1 or BCL1) has applications to a number of cancers including but not limited to breast cancers, colon cancers and pancreatic cancers, and functions as a major positive regulator of the $G_1$ restriction checkpoint of the cell cycle of normal mature animal cells. (See Hunter and Pines, 1994; Sherr, 1996.)

Cyclin D1 (CCND1) is a regulatory protein overexpressed in many carcinomas. Cyclin D1 acts by binding to and regulating the cyclin dependent kinases CDK4 and CDK6. CCN D1 gene expression is low in quiescent cells (in $G_0$) but is induced as cells respond to growth factors and enter the cell cycle leading to an increase in active cyclin D1-CDK4/CDK6 complexes.

Rapid cell cycling irrespective of appropriate growth signals and failure to respond to growth inhibition signals such as contact inhibition are characteristics of cancer cells.

Inappropriate expression of cyclin D1 during chromosomal inversion, translocation or amplification has been characterized in a variety of tumor cells (Hall and Peters, 1996; Sherr, 1996 for reviews). Cyclin D1 gene overexpression is also seen in many tumors without gross chromosomal rearrangements or amplification of the cyclin D1 gene. In fact, overexpression of cyclin D1 is seen in 50% of primary breast carcinomas, in 30% of adenocarcinomas of the colon (Hall and Peters, 1996), in familial adenomatous polyposis (Zhang et al., 1997) as well as in many cases of pancreatic cancer (Gansauge et al., 1997).

In addition, transgenic mice that overexpress the cyclin D1 gene in mammary epithelium show mammary hyperplasia and develop mammary adenocarcinomas (Wang et al., 1994). Overexpression of cyclin D1 in cultured cells has been shown to result in early phosphorylation of pRB (Jiang, et al., Oncogene, 8:3447–3457, 1993), shortening of the G1 phase and makes the cells growth factor independent (Jiang et al., 1993; Quelle et al., 1993;

Resnitzky et al., 1994). When injected into nude mice these cells produce tumors (Jiang et al., 1993).

The link between inappropriate expression of cyclin D1 and tumorigenesis indicates that cyclin D1 is a good target for therapeutic intervention. Cyclin D1 antisense molecules have been shown to reduce the neoplastic phenotype of human esophageal, colon and pancreatic cancer cells overexpressing cyclin D1 in culture as well as the ability of these cells to produce tumors in mice (Zhou et al., 1995; Arber et al., 1997; Kornmann et al., 1998). In these studies antisense technology was used to specifically inhibit cyclin D1 mRNAs.

Accordingly, regulated expression of cyclin D1 finds utility in cancer and other therapies. The present invention provides identification of DNA response elements within the cyclin D1 promoter that are involved in regulation of gene expression and a demonstration of the utility of DNA-binding compounds that bind to a sequence in the vicinity of a DNA response element of the cyclin D1 promoter as a means to modulate expression of a gene operably linked to the cyclin D1 promoter.

The human CCND1 gene has been previously cloned and sequenced (Motokura et al., 1991; Withers et al., 1991; Xiong et al., 1991). An upstream promoter sequence of the CCND1 gene has also been cloned and sequenced (Herber et al., 1994a,1994b; Philipp et al. 1994). The CCND1 promoter sequence may be found in GenBank at Accession HUMPRDA1A (Motokura and Arnold, 1993).

Potential Sp1, E2F, CRE, Oct1, Myc/Max, AP-1, Egr, NFκB, STAT5, Ets, PRAD and TCF/LEF sites have been previously identified in the cyclin D1 promoter (Motokura & Arnold 1993; Herber, Truss, et al. 1994; Philipp, Schneider, et al. 1994; Hinz, Krappmann, et al. 1999; Matsumura, Kitamura, et al. 1999; Shtutman, Zhurinsky, et al. 1999; and Tetsu & McCormick 1999). Several of these sites have been demonstrated to play a role in cyclin D1 regulation in various cell lines (Philipp, Schneider, et al. 1994; Albanese, Johnson, et al. 1995; Watanabe, Lee, et al. 1996; Yan, Nakagawa, et al. 1997; Watanabe, Albanese, et al. 1998; Beier, Lee, et al. 1999; Hinz, Krappmann, et al. 1999; Matsumura, Kitamura, et al. 1999; Shtutman, Zhurinsky, et al. 1999; and Tetsu & McCormick 1999).

The prior art includes some analysis of the cyclin D1 promoter, but does not indicate appropriate targets for regulated gene expression using the cyclin D1 promoter. Analysis of transcription factor binding sites in the cyclin D1 promoter was carried out to identify portions of the cyclin D1 promoter that can be used to regulate the expression of a gene operably linked to the cyclin D1 promoter and important transcription factor binding sites were identified, and modified as detailed in Example 5.

A 1900-bp fragment of the human cyclin D1 promoter was PCR amplified from genomic DNA and subcloned into the vector pGL3-basic (Promega) to form a reporter construct. A series of modified promoters were made and promoter activities compared to that of the full-length (−1745) cyclin D1 promoter following transfection into asynchronous MCF7 human breast carcinoma cells, which overexpress cyclin D1, and important regulatory regions of the promoter were identified.

The −30 to −21 region of the CCND1 promoter was identified as an important regulatory region for promoter activity. The −30 to −21 sequence was modified to contain binding sites for the netropsin dimer 21x, which were introduced overlapping the −30 to −21 sequence. In one case, the site was introduced into the 3' end of the A/T-rich −30 to −21 site (SEQ ID NO:36), by changing only 2 bp (10 bp 21x, SEQ ID NO:37, Example 5). A second 21x binding site was constructed by mutating 5 bp of the wild-type promoter sequence to produce an uninterrupted 8 A/T stretch (8 bp 21x, SEQ ID NO:38, Example 5). These constructs were cloned in the context of the −1745 cyclin D1 promoter in pGL3 basic, transfected into MCF7 cells and demonstrated to retain high levels of promoter activity in MCF7 cells in the absence of 21x.

Binding of 21x to these sites was confirmed using a hybridization stabilization assay, as detailed herein and described in co-owned application U.S. Ser. No. 09/151,890 and U.S. Ser. No. 09/393,783, incorporated herein by reference.

In summary, the binding preference of compounds to various the cyclin D1 promoter sequences was examined in a competitive hybridization-stabilization binding assay (HSA). In the H1SA a nucleotide sequence of interest is represented in an oligonucleotide duplex, and the duplex was tested for its ability to compete with an indicator oligonucleotide duplex which is known to bind the test molecule with a certain degree of affinity. The indicators are rich in AT bases and labeled with either a fluorescent probe or a quencher moiety on each of the two strands. The binding of the compound to the indicator stabilizes the duplex formation allowing the fluorescence to be quenched. If the compound prefers the test sequence (competitor) more than the indicator, it is less available to stabilize the indicator duplex and thus quenching is reduced. Therefore, a higher fluorescence signal implies a higher degree of binding preference to the test sequence relative to the indicator.

In one example, the hybridization stabilization assay employs a DNA duplex as an indicator for binding, wherein one strand of the duplex is 5' labeled with fluorescein, and the complementary strand was 5' labeled with a dabsyl quenching molecule. When the two strands are mixed together with a DNA-binding molecule, which can stabilize the duplex form, the signal from the fluorescein is quenched by the dabsyl on the complementary strand. Various cold competitor duplexes are then added to see whether they provide preferred binding sites for a DNA-binding compound, e.g., 21x. If the competitor DNA, for example, an oligonucleotide containing a 21x binding site, or the wild-type cyclin D1 control sequence bind 21x, 21x is titrated away from the indicator duplex. This results in destabilization of the indicator duplex and as the strands separate, quenching is diminished and fluorescence increases.

In the experiments described in Example 5, treatment of MCF7 cells containing these constructs with 21x resulted in down regulation of cyclin D1 promoter activity while promoter constructs lacking the 21x sites were unaffected. The results show that 21x treatment of MCF7 cells was able to specifically lower cyclin D1 promoter activity 4-fold when a 21x binding site was present overlapping a transcriptional activator site.

One application of the present invention is the use of the molecular switch to modulate cyclin D1 expression in cancer cells that overexpress the gene.

Regulated Gene Expression Using the HBV Core Promoter

Viral induced Hepatitis B (HBV) in humans is estimated to have infected 300 million people worldwide, with a small but significant number of infected individuals developing severe pathologic consequences, including chronic hepatic insufficiency, cirrhosis, and hepatocellular carcinoma. HBV-specific promoters involved in viral replication are therefore relevant to both therapy of HBV disease and regulated gene expression which is specific to liver cells.

Characterization of the HBV core promoter, which directs the transcription of two greater than genome size messenger transcripts, has been described (for reviews, see Ganem D, in Field Virology $3^{rd}$ Ed. 1996 and Kann M and Gerlich, W, in Viral Hepatitis, $2^{nd}$ Ed).

The results of studies on the promoter activity of linker scanner mutants of the native sequences HBV core promoter indicated that the TATA box and proximal HNF3 sites are control elements critical for promoter activity (data not shown).

Small DNA-binding compounds were utilized to test their ability to alter the transcription level from wild type and engineered HBV core promoters, either by interference and/or displacement of protein factor binding to its cognate nucleotide binding sequences. The nucleotide composition at the core TATA box contains a run of seven A and T (adenine and thymine) bases that could serve as a preferred binding site for the compounds 21x and GL046732, which exhibit a binding preference of A/T-rich sequences. In addition, various engineered promoter constructs were prepared containing introduced A/T-rich sequences. Treatment with 21x and/or GL046732 was effective to down-regulate the core wild type promoter activity in constructs with A/T-rich sequences in a regulatory region (Example 6), indicating that DNA-binding compounds, are capable of altering levels of gene transcription through interaction with a basal transcription factor.

VII. Selection Of DNA-Binding Compounds

Exemplary pre-screening assays for candidate compounds include, but are not limited to, DNA binding assays and protein displacement assays, such as gel mobility shift assays, competitive binding assays, DNA footprinting, etc. Such assays may be carried out using various techniques which are known in the art. Briefly, an exemplary assay provides information about the sequence-specific or sequence-preferential binding to DNA sequences, for example, binding to A/T rich sequences. Gel mobility shift assays may be used to determine the effect of a compound on the binding of a transcriptional regulatory protein to its DNA response element, based on the change in size (and corresponding mobility on a gel) of the DNA/protein complex relative to the DNA alone.

DNA footprinting may then be used to characterize the binding region based on the stability of drug binding sequence/drug complex to nuclease degradation.

In one embodiment, compounds for use in the regulatable gene expression system of the invention are pre-selected for DNA-binding and transcriptional regulatory protein displacement in a form of the Merlin™ assay. Exemplary pre-screening assays include various forms of the Merlin™ assay. See, e.g., co-owned U.S. Pat. Nos. 5,306,619, 5,693, 463, 5,716,780, 5,726,014, 5,744,131, 5,738,990, 5,578,444, 5,869,241, expressly incorporated reference herein.

In other embodiments, compounds are pre-selected in a nucleic acid ligand interaction assay, such as that described in co-owned, co-pending, U.S. Ser. No. 09/151,890 (expressly incorporated by reference, herein), or another nucleic acid binding assay known to those of skill in the art.

Candidate compounds may be modified or dimerized, screened in a DNA binding and displacement assay, as further described for NF-κB, UL9, LacR, cyclin D1 and HBV HNF3. Further evaluation of interesting compounds may then be carried out in a cell-based aspect of the molecular switch system, as further described below for UL9/VP16, rrnB P1 in E. coli, cyclin D1 and HBV HNF3 and TATA sites. The potential efficacy, toxicity and pharmacokinetic properties of a compound may be evaluated in a cellular environment in such assay systems.

In order to develop an effective regulatable in vivo gene expression systems, additional studies are carried out in vivo.

Animal models such as mice, rat, rabbit, dog, chimpanzee, zebra, fish, etc., can be employed for such in vivo tests.

VIII. In vivo Gene Therapy

A. Regulatable In vivo Expression Systems

An effective regulatable in vivo expression system for use in the methods and compositions of the invention must have the following properties: (1) the ability to both increase and decrease the expression of a selected therapeutic transgene, (2) the ability to tightly control the expression level of a given transgene, (3) the potential for cell type-, tissue-specific or broadly-based expression, (4) a stable vector which may be efficiently transduced into cells in vivo and maintain promoter activity for an extended time following transduction, (5) the ability to be regulated by a compound with minimal toxicity, (6) the ability to operate with either engineered (exogenous) or natural (native), exogenous or endogenous transcriptional regulatory elements, and (7) application to (a) treatment of genetic and non-genetic diseases (i.e., cancer and infectious diseases), (b) toxic recombinant protein or secondary metabolite production, as well as (c) agricultural uses.

B. Vectors for In vivo Delivery of Therapeutic Genes

Successful gene therapy depends on the controlled expression of transgenes. Factors which affect the expression of such transgenes include the efficiency of transduction, the stability of the vector, and efficient activation of the promoter that regulates expression of the transgene.

The regulatable molecular switch constructs of the invention may be delivered in vivo by gene delivery vehicles known to those of skill in the art, including, but not limited to viral vectors (retroviral, adenoviral or adeno-associated viral vectors; Bohl, et al., 1997; Bohl and Heard, 1997; Burcin, et al, 1999; Ye, et al., 1999) herpes virus vectors, pox virus vectors; non-viral vectors, including non-liposomal vectors (i.e., FuGene™6, Roche Molecular Biochemicals), liposomal vectors (i.e., DOSPER and DOTAP, Roche Molecular Biochemicals) and other non-viral means including receptor-mediated delivery, calcium phosphate transfection, electroporation, particle bombardment (gene gun), and pressure-mediated gene delivery.

In general, the efficiency of gene transfer by viral vectors, e.g., retroviral vectors and adenoviral vectors, is higher than that of non-viral vectors. Retroviral vectors, including the most widely used amphotrophic murine leukemia virus (MuLV) vector, can infect only replicating cells, and typically, their transduction rate is lower than that of adenoviral vectors. However, since retroviral vectors integrate into the host genome the expression of the transgene is persistent. Recently retroviral vectors have been developed in which the therapeutic gene carrying vector construct is introduced into a packaging cell line that carries two independent constructs, which express structural proteins for packaging, thereby addressing safety issues surrounding the generation of replication competent retroviruses (Salmons and Gunzburg, 1997).

Adenoviral vectors can infect many cell types, resting and replicating, with high efficiency. However, the expression of the transgene is transient, and in addition, these vectors induce a strong host immune response. An improved adenoviral vector has the majority of the viral genome removed and increased the capacity of the vector for transgenes. Recently, a hybrid adeno/retroviral vector has been designed (Bilbao, et al., 1997).

Adeno-associated virus vectors also facilitate integration of transgenes into host chromosomes, and constitutive expression of a transgene, without evoking a strong host immune response. However, limited cloning capacity, and the requirement of a helper adenovirus virus for its replication have hampered use of these types of vectors in gene therapy.

Once a transgene has been transferred into cells either via a viral or non-viral vector, expression of the transgene is governed by the strength and nature of the promoter (i.e., constituitively active vs. tightly regulated). In most cases high levels of expression are preferred in the methods and compositions of the invention, and strong viral promoters are incorporated into vectors for in vivo expression of transgenes. However, in some cases lower levels of expression are desired, and cellular promoters are used.

Factors to be considered in order to achieve non-toxic, selective and controlled expression of transgenes include, targeted delivery of therapeutic genes to a particular tissue, cell type specific expression, and expression which may be modified by an exogenous inducer.

For example, replicating cells may be targeted by retroviral vectors and neuronal tissue may be targeted by Herpes simplex virus (HSV) vectors. In the case of retroviral and adenoviral vectors, which lack tissue specificity, targeting may be improved, for example, by the use of recombinant pseudo-typed viruses which are produced in a packaging cell line that provides a different envelope protein (Salmons and Gunzberg, 1993), by engineering the envelope protein to redirect the interaction between the envelope protein and a cell surface receptor (Valsessia-Wittman et al., 1994), or to improve internalization of the vector upon receptor binding (Bushman, 1995). For adenoviral vectors, cell type specificity can be augmented by modification of the fiber protein (Wu, et al., 1994). Similarly, non-viral vectors may be modified by coupling of antibodies to liposomes (Mizuno, et al., 1990). In addition, incorporation of viral surface glycoproteins or fusogenic proteins into liposomes confers the tropism of the coupled molecules onto the liposomes (Morishida, et al., 1993; Bagai, et al., 1993).

Expression of transgenes of interest may also be controlled at the level of transcription, by the use of cell type- or developmental stage- specific promoters or promoter elements in gene transfer vectors, as further described in co-owned U.S. Ser. No. 60/122,513, expressly incorporated by reference herein.

Although many promoters and elements confer a degree of cell type specificity, transgene expression is typically constitutive in target tissues. Temporal regulation of therapeutic transgenes is highly desirable, to avoid toxicity which may occur with constitutive expression. Promoters which are inducible by exogenous factors such as hormones, growth factors, metabolites and stress factors are useful in the methods and compositions of the invention. (See, e.g., Yarranton, 1992; Gossen, et al., 1993). Exemplary inducible cellular and viral promoters which exhibit restricted tissue specificity find utility in the methods and compositions of the invention, e.g., the tyrosinase (Miller, et al., 1995), prostate specific antigen (Culig et al., 1994), $\alpha$-feto protein (Ido, et al., 1995) and MVMp P4 (Perros, et al., 1995) promoters. Exemplary cellular promoters which are generally not tissue-specific, may also be used in the methods and compositions of the invention, e.g., a glucocorticoid responsive promoter (Lu and Federoff, 1995), a heavy metal responsive promoter (Koh, et al., 1995) and the cytochrome P450 1A1 promoter (Smith, et al., 1995).

The feasibility of tissue-specific regulatable gene expression in vivo has been demonstrated by liver-specific expression using a liver-specific promoter (Burcin, et al., 1999).

Gene therapy is applicable to many medical indications including monogenic diseases, multigenic diseases, oncology, infectious diseases, and acquired diseases. Temporal and spatial regulation of therapeutic transgenes is of value in many of these fields. In many of these fields molecular switch technology will be needed for optimal gene therapy protocols.

Disease targets include, but are not limited to, cancer such as prostate cancer, breast cancer, lung cancer, colorectal cancer, melanoma and leukemia; infectious diseases, such as HIV, monogenic diseases such as CF, hemophilia, phenylketonuria, ADA, familial hypercholesterolemia, and multigenic diseases, such as restenosis, ischemia, and diabetes.

In one embodiment, a natural tissue-specific promoter is modified to include one or more introduced compound binding sequences near one or more natural transcriptional regulatory factor binding sites which are essential for transcriptional regulation of the natural tissue-specific promoter.

Temporal and spatial regulation of gene expression can be achieved by combining the tissue specificity of such a promoter with regulation of the interaction between the tissue-specific promoter and one or more essential transcriptional regulatory proteins, by the exposure of the promoter to a DNA binding compound which exhibits sequence-preferential binding to the introduced compound binding sequence(s).

Once the one or more binding sites for such an essential transcriptional regulatory protein are determined, compound binding sequence(s), e.g. for a small molecule, are engineered into the promoter near the transcriptional regulatory protein DNA response element(s) and thereby be used to regulate the binding of the transcriptional regulatory protein to the promoter, resulting in regulation of promoter activity.

In a related aspect of the invention, a synthetic promoter is made by introducing one or more tissue-specific transcription factor binding sites and one or more compound binding sequences into the sequence of a tissue-specific regulatable promoter such that the promoter may be regulated by a compound which preferentially binds the compound binding sequence(s), e.g., a small molecule. Such a small molecule may target an essential transcription factor or tissue specific transcription factor if it is essential to the activity of the promoter.

IX. Expression of Recombinant Proteins

In vitro

Suitable host cells for cloning or expressing recombinant proteins include prokaryotic, yeast, and higher eukaryotic cells. Suitable prokaryotes include, but are not limited to, gram-negative and gram-positive bacteria, for example, *E. coli*, various strains of which are publicly available.

Host cells are transfected or transformed with expression or cloning vectors for recombinant protein production and cultured in conventional nutrient media modified as appropriate for inducing promoters, selecting transformants, and/or amplifying the expression of genes encoding the desired sequences. The culture conditions, such as media, temperature, pH and the like, may be optimized according to knowledge generally available to those of skill in the art. In general, principles, protocols, and practical techniques for maximizing the productivity of cell cultures can be found in Butler, 1991, and Sambrook, et al. 1989.

Methods of transfection are known to those of skill in the art, for example, CaPO$_4$ transfection, bacterial protoplast fusion with intact cells, nuclear microinjection, electroporation, or in methods that employ polycations, such as, polybrene or polyornithine. Transfection is carried using standard techniques, as appropriate to the particular type of cells being transformed.

Infection with *Agrobacterium tumefaciens* is generally used for transformation of plant cells, as described by Shaw, et al., 1983 and WO 89/05859 published 29 Jun. 1989. Mammalian cell transformations may be carried out as generally described in U.S. Pat. No. 4,399,216: Keown, et al., 1990 and Mansour, et al., 1988.

In addition to prokaryotes, eukaryotes such as filamentous fungi or yeast are useful for expression of recombinant proteins. *Saccharomyces cerevisiae* is a commonly used lower eukaryotic host microorganism.

Expression of recombinant proteins in yeast are typically carried out following transfection according to the methods described in Van Solingen, et al., 1977 and Hsiao, et al., 1979.

Suitable host cells for the expression of glycosylated recombinant proteins are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line, 293, Graham, et al., (1977); Chinese hamster ovary cells (Cho, et al., (1980); human lung cells (W138, ATCC CCL 75); and human liver cells (Hep G2, HB 8065). Large numbers of cell lines are publicly available, e.g., from the American Type Culture Collection (ATCC, Manassas, Va.). The selection of the appropriate host cell is deemed to be within the skill in the art.

In general, in methods for production of recombinant proteins, the nucleic acid (e.g., cDNA or genomic DNA) encoding a recombinant protein or polypeptide of interest is inserted into a replicable vector for cloning, or for expression. Various vectors are publicly available, and may take the form of a plasmid, cosmid, viral particle, or phage. The appropriate nucleic acid coding sequence may be inserted into the vector by a variety of procedures known to those skilled in the art of recombinant DNA technology.

In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The desired recombinant protein or polypeptide may be produced recombinantly directly, or as a fusion polypeptide with a heterologous polypeptide, which may be a signal sequence or other polypeptide having a specific cleavage site at the N-terminus of the mature protein or polypeptide. Included in heterologous nucleic acid constructs for use in the methods of the invention are signal sequences that allow processing and translocation of the protein, as appropriate. The heterologous nucleic acid construct typically lacks any sequence that might result in the binding of the desired protein to a membrane.

In some cases, the recombinant protein may be produced as a precursor protein, which may be further processed in cell culture or following extraction from the culture medium.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most gram-negative bacteria, and various viral origins of replication (SV40, polyoma, adenovirus, VSV or BPV) are useful for cloning vectors in mammalian cells.

In cases where two separate plasmids are transformed into bacteria, compatible replicons are used employing techniques generally known to those of skill in the art.

In most cases, expression and cloning vectors also contain a selectable marker gene. Typical selectable marker genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors generally contain a promoter operably linked to the recombinant protein- or polypeptide-encoding nucleic acid sequence to direct mRNA synthesis. Promoters recognized by a variety of potential host cells are well known. Such promoters my be inducible or constitutive, and may be of prokaryotic, eukaryotic or viral origin.

In the methods and compositions of the invention, the molecular switch systems described herein are used for expression of recombinant proteins and polypeptides.

When an endogenous transcriptional regulatory protein is utilized in the molecular switch system of the invention, a vector is provided which includes a DNA binding site for the transcriptional regulatory protein, a compound-binding sequence, a promoter, and a transgene which encodes a recombinant protein or polypeptide of interest, under the control of the aforementioned promoter.

In some cases, the molecular switch systems of the invention for expression of recombinant proteins include two vectors, wherein one vector comprises the DNA binding site for a transcriptional regulatory protein, a compound-binding sequence, a first promoter, and a transgene which encodes a recombinant protein or polypeptide of interest, under the control of the aforementioned promoter. A second vector is effective to express an engineered transcriptional regulatory protein or natural regulatory protein having a regulatory domain and a DNA binding domain under the control of a first promoter (inducible or constitutive). The regulatable expression system also includes compounds or inducers which bind to the compound-binding sequence.

In other cases, a single vector system is used for expression of recombinant proteins in vitro. In such cases, the vector includes the DNA binding site for a transcriptional regulatory protein, a compound-binding sequence, a first promoter, and a transgene which encodes a recombinant protein or polypeptide of interest, under the control of the first promoter and is effective to express an engineered transcriptional regulatory protein or natural regulatory protein under the control of a second promoter. The expression of one or both of the transgene and transcriptional regulatory protein may be under the control of a constitutive or compound-inducible promoter.

In still other cases, a single vector is effective to express both a transcriptional regulatory protein and a transgene under the control of a single compound-inducible promoter, utilizing internal ribosomal entry sites (IRES).

Alternatively, the molecular switch comprises a single vector which has a transcriptional regulatory protein under the control of a single compound-inducible and a transgene under the control of a constitutive promoter.

Transcription of a DNA encoding a recombinant protein or polypeptide by higher eukaryotes may be increased by inserting an enhancer sequence into the vector. Enhancers are cis-acting elements of DNA, usually from about 10 to 300 bp, that act on a promoter to increase its transcription. Many enhancer sequences are now known from mammalian genes, however, frequently eukaryotic viral enhancers are used. The enhancer may be incorporated into the vector at a position 5' or 3' to the recombinant protein or polypeptide coding sequence, but is preferably located at a site 5' to the promoter.

Expression vectors used in eukaryotic host cells (yeast, fungi, insect, plant, animal, or human) will also contain sequences necessary for the termination of transcription and for stabilizing the mRNA. Such sequences are commonly available from the 3' and, occasionally 5', untranslated regions of eukaryotic or viral DNAs or cDNAs.

Molecular biological procedures routinely employed by those of skill in the art for production of recombinant proteins are provided in Sambrook, et al., 1989 and Ausubel, et al., 1989, both of which are expressly incorporated by reference herein.

Heterologous nucleic acid constructs for use in the methods of the invention may encode any protein or polypeptide of interest, or an intermediate in a biosynthetic pathway leading to a product or secondary metabolite of interest.

Exemplary recombinant proteins or polypeptides which may be expressed using the molecular switch systems of the invention, include, but are not limited to, enzymes; immunoglobulins; recombinant proteins such as those used in therapeutics; including, but not limited to; serum albumin; Factor VIII, tissue plasminogen factor, erythropoietin, colony stimulating factors, such as G-CSF and GM-CSF, cytokines such as interleukins, integrins; surface membrane protein receptors; T cell receptors; structural proteins, such as, collagen, fibrin, elastin, tubulin, actin, and myosin; growth factors and growth hormones. The protein may also be an industrial protein or enzyme as exemplified by peroxidase, glucanase, alpha-amylase, and glucose oxidase).

Such exemplary recombinant proteins or polypeptides may be expressed using the molecular switch systems of the invention in the context of in vitro expression in bacteria, yeast, insect cells, mammalian cells and plant cells as well as in vivo in transgenic animals and plants.

In one further embodiment the molecular switch system may be used to express more than one recombinant protein at the same time. For example, a "switch on" system using a transcriptional regulatory protein with a repressor as the regulator component could be used to increase expression of one recombinant protein at the same time a "switch off" system using a transcriptional regulatory protein with an activator component is used to decrease expression of a second protein, e.g., a proteolytic enzyme.

In vivo in Transgenic Animals

Nucleic acids which encode recombinant proteins, polypeptides, and modified forms thereof, may be used to generate transgenic animals which, in turn, are useful in the production of therapeutically useful reagents. A transgenic animal (e.g., a mouse, rat or goat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a polypeptide or protein of interest can be used to clone genomic DNA encoding that polypeptide or protein in accordance with established techniques. Methods for generating transgenic animals, particularly animals such as mice, rats and goats, have become conventional in the art and are described, for example, in U.S. Pat. Nos. 4,736,866, 4,870,009 and 5,907,080.

Typically, transgenic animals that include a copy of a transgene encoding a polypeptide or protein of interest introduced into the germ line of the animal at an embryonic stage can be used to examine the effect of increased expression of DNA encoding the polypeptide or protein of interest.

Recently, transgenic animals are being used to produce various types of recombinant proteins. Transgenic goats which produce therapeutic proteins in their milk have been developed and recently a commercial kit, the pBC1 Milk Expression Vector Kit (Genzyme Transgenics Corporation and Invitrogen Corp.), became available for the production of recombinant proteins in the milk of transgenic mice. In such methods, the DNA sequences for a milk protein promoter is operably linked to the coding sequence for a recombinant protein or polypeptide of interest. Similarly, the molecular switch system described herein find utility in regulated, e.g., switch-on, expression of recombinant proteins or polypeptides of interest in transgenic animals.

X. Agricultural Applications

A. Regulation of Gene Expression

Regulatable gene expression is applicable to many agricultural uses as well. This aspect of the invention includes methods directed to the production of transgenic plants using the regulatable expression (molecular switch) systems of the invention, resulting in the production of; (1) non-native recombinant proteins and polypeptides, (2) modified native proteins and polypeptides, and (3) secondary metabolites in such transgenic plants.

Regulation of transcription using exogenous bacterial transcriptional repressors such as LacR and TetR together with plant promoters modified to contain an appropriate bacterial operator sequence, have been successfully employed in various plant systems such as *Arabidopsis*, carrot and tobacco cells (Gatz, et al., 1991; Wilde, et al, 1992; Ulmasov, et al, 1997).

The use of chimeric transcriptional activators such as LacR/Gal4 (Moore et al, 1998) and Gal4/VP16 or Gal4/THM18 (Schwechheimer, et al., 1998) for the regulation of transgene expression from engineered promoters has also been demonstrated in plant systems.

The molecular switch system of the invention finds utility in the regulation of plant gene expression by providing either an exogenous or endogenous transcriptional regulatory factor (repressor or activator), which is active in plants, together with a corresponding DNA response element for the transcriptional regulatory factor, a compound binding site and a DNA-binding compound which preferentially binds to the compound binding site.

In most cases, gene expression is achieved by introducing a single vector or nucleic acid construct into plant cells, wherein the vector includes either: (1) a DNA response element for a transcriptional regulatory protein, a compound-binding sequence, a promoter, and a transgene which encodes a recombinant protein or polypeptide of interest, under the control of the promoter, which functions together with a native transcriptional regulatory protein and an exogenously supplied DNA binding compound or (2) a DNA response element for a transcriptional regulatory protein, a compound-binding sequence, a promoter, and a transgene which encodes a recombinant protein or polypeptide of interest, under the control of the promoter, together with an engineered transcriptional regulatory protein or natural regulatory protein also under the control of a promoter, which functions together with an exogenously supplied DNA binding compound.

In some cases, gene expression is achieved by introducing two vectors or nucleic acid constructs into plant cells, wherein a first vector is effective to express an engineered transcriptional regulatory protein or natural regulatory protein, and a second vector includes a DNA binding sequence for the transcriptional regulatory protein, a compound-binding sequence, a promoter, and a transgene which encodes a protein or polypeptide of interest, under the control of the aforementioned promoter, which function together with an exogenously supplied DNA binding compound.

Both the one and two vector aspects, and the one and two promoter aspects of the molecular switch system of the invention include compounds or inducers which bind the compound-binding sequence. Exemplary compounds for use in the molecular switch system of the invention are further described above.

B. Exemplary Plant Transcription Factors and Associated Binding Proteins

Exemplary transcriptional regulatory factors for use in plants include the UL9/VP16 activator or UL9/KRAB repressor, together with a regulatable transgene operably linked to a promoter having one or more UL9 DNA response elements in the vicinity of one or more binding sequences for 21x.

It will be understood that the various components of the molecular switch system are interchangeable. For example, transcriptional regulatory factors for use in the methods of the invention may include any of a number of DNA binding domains, such as DAT1 from *Saccharomyces cerevisiae*. DAT1 specifically recognizes the minor groove of non-alternating oligo(A).oligo(T) sequences (Reardon, et al., 1995), and accordingly provides a sequence for the effective binding of 21x and compounds which act by a similar mechanism.

In one example, a heterologous nucleic acid construct is described which has the coding sequence for a reporter or gene of interest, linked to a minimal promoter (i.e. CaMV 35S) with two upstream lac operator sequences fused to the promoter sequence, which serve as the binding site for a transcription factor, "LhG4". LhG4 has a transcriptional activator domain from Gal4 fused to a mutant lac-repressor, which has enhanced binding affinity, and functions to regulate transcription of coding sequences downstream of the CaMV 35S promoter. (See, e.g., Moore, et al., 1998).

The tet repressor-operator system has been used to regulate the gene expression in transgenic tobacco plants. A transgenic plant constitutively synthesizing a large number of Tet repressor monomers per cell was made, followed by introduction of a heterologous nucleic acid construct containing the beta-glucuronidase (Gus) gene under the control of a CaMV 35S promoter, modified to contain two tet operators. Expression of the GUS gene was repressed 50- to 80-fold when both operators were positioned downstream of the TATA box. (See, e.g., Gatz, et al., 1991).

In some cases, the molecular switch system may make use of endogenous transcription factors found in plants. For example, the endogenous plant transcriptional activator 780BP (780 binding protein) of cauliflower inflorescence which binds to the 780 gene of T-DNA may be used. The DNA response element was determined (Adams and Gurley, 1994; TTGAAAAATCAACGCT, SEQ ID NO:23) and includes the preferred sequence for binding of 21x and other compounds which target "AT-rich" sequences.

In one exemplary embodiment, tandem repeats of the 780BP DNA response element are fused to the minimal CaMV 35S promoter sequence operably linked to a transgene, and 21x is used to regulate the binding of 780BP at the tandem repeated sites.

In a further exemplary embodiment, a plant tissue-specific transcription factor, NtBBF1, identified by its ability to bind to a regulatory domain of the rolB oncogene promoter (found in the *Agrobacterium rhizogenes* Ti plasmid in tobacco), is used to regulate transcription. The DNA response (cis) element for NtBBF1 has been identified in the rolB gene (ACTTTA, SEQ ID NO:27). Mutational studies have indicated that this sequence is essential for the expression of rolB in apical meristems (Baumann, et al., 1999). A tissue specific regulatable promoter may be designed using the DNA response element for NtBBF1 in the rolB promoter or an engineered promoter having the DNA response element for NtBBF1 fused to a minimal promoter sequence wherein the sequence in the vicinity of the DNA response (cis) element for NtBBF1 is modified to include small molecule binding sequences (i.e., 21x). For example, the NtBBF1 cis element (bold, uppercase), may be modified to include one or more introduced compound binding sequences (lowercase) for 21x or another compound that preferentially binds to "AT-rich" sequences. Potential compound binding sequences are indicated as "( )".

```
AC(TTTAtttt)        (SEQ ID NO:65)

(aaaACTTTA)         (SEQ ID NO:77)
```

The DNA response element for NtBBF1 may be fused to a minimal promoter in tandem to increase the activity of the promoter.

Overexpression of the natural plant transcription factor, "CBF1", which binds to a DNA response element, "CRT/DRE", found in the promoter of cold-inducible genes may find utility in regulating cold tolerance by incorporating CBF1 and CRT/DRE into the molecular switch systems of the invention. (See, e.g., Warren, 1998).

A cis-acting element identified in the promoter region of the rd29A gene is associated with dehydration and cold-induced gene expression. The sequence designated the dehydration response element ("DRE", TACCGACAT, SEQ ID NO:28), has been found in the promoter regions of other dehydration and cold-stress inducible genes. When the stress inducible promoter rd29A was used to drive expression of a DRE-binding protein, "DREB1A" in *Arabidopsis*, transgenic plants were produced that were drought-, salt- and freezing-tolerant. (Kasuga, et al., 1999). The DREB1A transcriptional regulatory protein and the DRE response element, may find utility in regulating drought-, salt- and cold-tolerance by incorporating them into the molecular switch systems of the invention.

Plant output traits of interest may be modified using the methods of the invention by introducing heterologous nucleic acid constructs which encode recombinant proteins, polypeptides, or intermediates in the biosynthetic pathway leading to the production of metabolites associated with such output traits.

Such heterologous nucleic acid constructs may encode native or non-native, e.g., mammalian or viral proteins or polypeptides.

In another aspect of the invention, recombinant proteins or polypeptides are produced in plants using the molecular switch methods of the invention.

C. Improved Output Traits

The development of plants having desired traits such as improved yield; disease resistance to fungal, bacterial, viral and other pathogens; insect resistance; herbicide resistance; improved fruit ripening characteristics; cold temperature and dehydration tolerance; increased salt and drought tolerance; improved food quality (i.e. nutritional content) and improved appearance has been the focus of agribusiness for many years.

Numerous genes involved in regulating such plant characteristics have been identified and characterized.

One example is the development of herbicide resistance in rice plants. Transformed rice has been shown to be resistant to at least imazethapyr, imazaquin, nicosulfuron, and primisulfuron, with suggested resistance to additional herbicides. (See, e.g., U.S. Pat. No. 5,773,703.)

Another example is genetically altered higher plants having a modified starch and sucrose biosynthesis phenotype, e.g., edible plants, such as peas with altered sucrose and starch content. (See, e.g., U.S. Pat. No. 5,773,693.)

Coding sequences for expression in plants using the regulatable expression vectors described herein include, but are not limited to, sequences which encode enzymes and other proteins or polypeptides that confer: disease resistance to fungal, bacterial, viral and other pathogens; insect resistance; herbicide resistance; fungicide resistance; and insecticide resistance.

Coding sequences associated with output traits of interest further include, those associated with: regulation of plant development; regulation of fruit ripening; increased salt and drought tolerance; and regulation of plant nutritional content, e.g., by altered oil composition in seeds, increased grain oil content, altered seed protein composition, altered carbohydrate composition in seeds, altered carbohydrate composition in fruits, and the like. (See, e.g., Brar, et al., 1996).

By way of example, numerous plant proteins associated with pathogenesis or pathogenesis-related proteins (PR proteins) which are induced in large amounts in response to infection by various pathogens, including viruses, bacteria and fungi have been identified.

In one aspect of the invention, the use of heterologous nucleic acid construct comprising the coding sequence for such pathogenesis-associated proteins can be used in the molecular switch systems of the invention to develop plants which have enhanced resistance to disease. (See, e.g., Redolfi, et al., 1983; Van Loon, 1985; and Uknes, et al., 1982; and U.S. Pat. No. 5,880,328, issued Mar. 9, 1999.)

D. Production of Recombinant Proteins and Polypeptides in Plants

Transgenic plants as the source of recombinant proteins and polypeptides offer the advantage of production at low cost, based on ease of plant transformation and scale up, correct assembly of the subunit components of multimeric proteins, and the lack of pathogens associated with recombinant protein or polypeptide production in cell culture. (See, e.g., Larrick, 1998).

Heterologous nucleic acid constructs for use in the methods of the invention may include coding sequences for recombinant proteins or polypeptides for pharmaceutical applications and nutraceutical production.

Exemplary recombinant proteins which have been produced in plants include vaccines, enzymes, hormones, plasma proteins, and antibodies. More recently technology has been developed for the production of polymers, such as microbial polyesters in plants. (See, e.g., Kolodziejczyk, 1999).

More specific examples of recombinant proteins which have been produced in plants include, SpaA of *S. mutans*, HBV surface antigen, M protein of HBV, LT of *E. coli*, CT of *V. cholerae*, capsid protein of Norwalk virus, rabies glycoprotein, VP1 of foot and mouth disease virus, secretory IgA and IgG. (See, e.g., Ma and Vine, 1999; Tian and Yang, 1998; Larrick, 1998).

E. Plant Transformation

Genetic transformation of plants is generally accomplished by introducing heterologous nucleic acid constructs into plants using *Agrobacterium* T-DNA vectors, microprojectile bombardment or by use of plant viral vectors, including, but not limited to, tobacco mosaic virus (TMV), cowpea mosaic virus (CPMV), tomato bushy stunt virus and alfalfa mosaic virus (AIMV), potato virus X (PVX) (Ma and Vine, 1999; Smolenska, et al., 1998).

Targeting recombinant proteins for secretion in plants may be accomplished using either native or plant-derived leader sequences, such that N-glycoslylation takes place. The expression of recombinant proteins or polypeptides may be targeted to extracellular spaces or to particular tissues, e.g., storage organs such as seeds, by use of tissue-specific promoters.

Once expressed, such recombinant proteins or polypeptides may be extracted and purified using techniques generally available to those of skill in the art. Optimal methods of plant transformation vary dependent upon the type of plant. It is preferred that the vector sequences be stably integrated into the plant genome.

Preferred methods for transformation of plant cells in molecular switch methods of the invention are *Agrobacterium*-mediated transformation, electroporation, microinjection, and microprojectile bombardment.

In another aspect of the invention, transgenic plants are produced following infection with a plant virus which has been genetically modified to encode one or more foreign genes, which are expressed following infection, as a soluble protein or polypeptide in the plant cytoplasm, targeted to cellular compartments, or alternatively fused to a viral coat protein which is displayed on the surface of the viral particle.

Expression vectors for use in the molecular switch methods of the invention comprise heterologous nucleic acid constructs, designed for operation in plants, with companion sequences upstream and downstream from the expression cassette. The companion sequences are of plasmid or viral origin and provide necessary characteristics to the vector to permit the vector to move DNA from bacteria to the plant host, such as, sequences containing an origin of replication and a selectable marker. Typical secondary hosts include bacteria and yeast.

In one embodiment, the secondary host is *E. coli*, the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

Vectors useful in the practice of the present invention may be microinjected directly into plant cells by use of micropipettes to mechanically transfer the nucleic acid construct or cassette (Crossway, Mol. Gen. Genet, 202: 179–185, 1985). Such nucleic acid constructs or cassettes may also be transferred into the plant cell using polyethylene glycol (Krens, et al., 1982).

High velocity ballistic penetration by small particles with the nucleic acid either within the matrix of small beads or particles, or on the surface may also be used for introduction of nucleic acid sequences into plant cells. (See, e.g., Klein, et al., 1987 and Knudsen and Muller, 1991).

Yet another method for introduction of nucleic acid sequences into plant cells is fusion of protoplasts with other entities, either minicells, cells, lysosomes or other fusible for introduction of nucleic acid segments into plant cells with lipid surfaces (Fraley, et al., 1982).

A preferred method for introduction of nucleic acid constructs or cassettes into the plant cells is electroporation (From, et al., 1985). In this technique, electrical impulses of high field strength reversibly permeabilize biomembranes allowing the introduction of plasmids into plant cells or protoplasts. Electroporated plant protoplasts reform the cell wall, divide, and form plant callus.

Another preferred method of introducing a nucleic acid construct comprising a sequence of interest into plant cells is to infect a plant cell, explant, meristem or seed with *Agrobacterium*, in particular *Agrobacterium tumefaciens*. A nucleic acid construct comprising such a sequence of interest can be introduced into appropriate plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch, et al., 1984; Fraley, et al., 1983; Schell, 1987).

Standard *Agrobacterium* binary vectors are known to those of skill in the art and many are commercially available. Expression vectors typically include polyadenylation sites, translation regulatory sequences (e.g., translation start sites), introns and splice sites, enhancer sequences (which can be inducible, tissue specific or constitutive), and may further include 5' and 3' regulatory and flanking sequences.

An exemplary binary vector suitable for use in the molecular switch methods of the invention include at least one T-DNA border sequence (left, right or both); restriction endonuclease sites for the addition of one or more heterologous nucleic acid coding sequences [adjacent flanking T-DNA border sequence(s)]; a heterologous nucleic acid coding sequence (i.e., the sequence encoding a protein or polypeptide of interest), operably linked to appropriate regulatory sequences and to the directional T-DNA border sequences; a selectable marker-encoding nucleotide sequence which is functional in plant cells, operably linked to a promoter effective to express the selectable marker encoding sequence; a termination element for the selectable marker-encoding nucleotide sequence; a heterologous Ti-plasmid promoter; a nucleic acid sequence which facilitates replication in a secondary host (e.g., an *E. coli* origin of replication) and a nucleic acid sequence for selection in the secondary host, i.e., *E. coli*.

In general, a selected nucleic acid sequence is inserted into an appropriate restriction endonuclease site or sites in the vector. Standard methods for cutting, ligating and *E. coli* transformation, known to those of skill in the art, are used in constructing vectors for use in the present invention. See, for example, Sambrook, et al. (1989) and Ausubel, et al., (1989).

In choosing a promoter it may be desirable to use a tissue-specific or developmentally regulated promoter for regulated expression in certain tissues without affecting expression in other tissues. Numerous examples of such promoters are known in the art or differential screening techniques may be used to isolate promoters expressed at specific (developmental) times, such as during seed development.

Generally, the construction of vectors for use in practicing the present invention are known by those of skill in the art. (See generally, Maniatis, et al., (1989), and Ausubel, et al., (c) 1987, 1988, 1989, 1990, 1993 by Current Protocols; Gelvin, et al., (1990), all three of which are expressly incorporated by reference, herein.

In one aspect of the invention, an *Agrobacterium* binary plant transformation vector is introduced into a disarmed strain of *A. tumefaciens* by electroporation (Nagel, et al., 1990), followed by co-cultivation with plant cells, to transfer the heterologous nucleic acid construct(s) into plant cells. Upon infection by *Agrobacterium tumefaciens*, the heterologous DNA sequence is stably integrated into the plant genome in one or more locations.

In a further aspect of the invention, transgenic plants are produced using *Agrobacterium* T-DNA vectors or microprojectile bombardment, where a heterologous nucleic acid coding sequence is integrated into the plant genome and traditional breeding is used to generate transgenic seed stock and transgenic plants.

In a further aspect, plant cells are transformed by infection with *Agrobacterium tumifaciens*. However, as will be appreciated, the optimal transformation method and tissue for transformation will vary depending upon the type of plant being transformed.

Suitable selectable markers for selection in plant cells include, but are not limited to, antibiotic resistance genes, such as, kanamycin (nptII), G418, bleomycin, hygromycin, chloramphenicol, ampicillin, tetracycline, and the like. Additional selectable markers include a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; and a methotrexate resistant DHFR gene.

The particular marker gene employed is one which allows for selection of transformed cells as compared to cells lacking the DNA which has been introduced. Preferably, the selectable marker gene is one which facilitates selection at the tissue culture stage of the molecular switch methods of the invention, e.g., a kanamyacin, hygromycin or ampicillin resistance gene.

Transformed explant cells are screened for the ability to be cultured in selective media having a threshold concentration of selective agent. Explants that can grow on the selective media are typically transferred to a fresh supply of the same media and cultured again. The explants are then cultured under regeneration conditions to produce regenerated plant shoots. After shoots form, the shoots are transferred to a selective rooting medium to provide a complete plantlet. The plantlet may then be grown to provide seed, cuttings, or the like for propagating the transformed plants. The method provides for high efficiency transformation of plant cells with expression of modified native or non-native plant genes and regeneration of transgenic plants, which can produce a protein, polypeptide or secondary metabolite of interest.

Once the expression of a protein, polypeptide or secondary metabolite of interest is confirmed using standard analytical techniques such as Western blot, ELISA, PCR, HPLC, NMR, or mass spectroscopy, whole plants are regenerated. Plant regeneration is described for example in Evans, et al., 1983 and in Vasil, 1984, and 1986).

XI. Utility of the Invention

The present invention can be used for (1) screening and optimizing as well as validation of the sequence specificity of a DNA binding molecule in cell based assays, (2) in vectors for controlled therapeutic gene expression in vivo, (3) in toxic protein production in eukaryotic expression systems, (4) for recombinant protein and secondary metabolite production, (5) in various agricultural uses, examples of which are described above, (6) as a research tool, and (7) in developmental and functional studies with transgenic animals, where molecular switches allow the temporal expression of the genes that are lethal if expressed at an early stage of development. Expression of disease or therapeutic genes in adult animals may aid the study of the function of these genes.

XII. Advantages

All of the prior art systems for regulated gene expression rely on the binding of a compound to a regulatory protein and each lacks some features of an effective regulatable expression system.

The molecular switch compositions and methods described herein provide the advantage of regulated gene expression using native transcriptional regulatory proteins which are present endogenously and which may also be exogenously provided.

In contrast to the prior art, in the molecular switch methods and compositions of the invention, the compound binds with double-stranded DNA and the binding of the compound to double-stranded DNA has an effect on the binding of a transcriptional regulatory protein to its DNA response element. In the methods of the invention, any compound which modulates the binding of a transcriptional regulatory protein to its DNA binding site can be used to regulate the expression of a gene operably linked to the promoter. The choice of inducer is not restricted by the transcriptional regulatory protein as long as it modifies the binding of the transcriptional regulatory protein to its DNA response element and thereby regulates the expression of a gene operably linked thereto.

By engineering one or more compound binding sequences in the vicinity of the DNA response element for an endogenous transcriptional regulatory protein, a compound can specifically target transcription factor binding to the engineered site or sites, resulting in greater specificity of regulation.

In addition, the invention provides a system that is tightly regulated by an exogenous factor which can regulate expression of the transgene without non-specifically affecting expression of endogenous cellular genes.

All patent and literature references cited in the present specification are hereby incorporated by reference in their entirety.

While the invention has been described with reference to specific methods and embodiments, it will be appreciated that various modifications and changes may be made without departing from the invention.

EXAMPLE 1

UL9 Chimeric Transcriptional Regulatory Constructs

Oligonucleotides comprising the UL9 DNA response element and one or two binding sequences for the A/T-rich binder, 21x were constructed. In each oligonucleotide the putative 21x-binding sequence(s) overlap the modified UL9 binding site (SEQ ID NO:18). The modified sequences include YK 202LX (FIG. 6, SEQ ID NO:19), YK 202RX-A (FIG. 6, SEQ ID NO:20), and YK 202RX (FIG. 6, SEQ ID NO:21), wherein the transcriptional regulatory protein DNA response site is indicated as bolded and uppercase, introduced compound binding sequences are indicated in lowercase and potential compound binding sequences are indicated as ( ) or [ ]. A gel mobility shift assay for protein displacement was used to measure compound induced protein displacement. A $^{32}P$ labeled oligonucleotide was incubated with 10 nM GST-UL9 at room temperature in the binding buffer (20 mM HEPES, pH 7.5, 50 mM KCl, 0.1 mM EDTA, 5% glycerol and 1 mM DTT) for 20 minutes, followed by the addition of 21x. The incubation was continued for 2 hours and the samples analyzed by polyacrylamide gel electrophoresis, with the amount of protein bound oligonucleotide quantitated. UL9 was displaced most efficiently when there was an overlap between protein and 21x binding sequences at 3' end of UL9 binding site, as shown in FIG. 7.

UL9 Activator Constructs

The strong sequence specific chimeric activator, UL9–VP16, was constructed the C-terminal DNA binding domain of UL9 fused to the N-terminus of the activation domain of VP16 utilizing pGEX-UL9 (Genelabs) and pACT (Promega), expressed under the control of a CMV immediate early enhancer/promoter. Luciferase reporter constructs with a series of tandem repeated UL9 binding sites and flanking compound-binding sites were made by modifying the pGSluc vector (Promega). In this vector the fire fly luciferase is under the control of synthetic promoter that is composed of five tandem repeats of GAL4 binding sites followed by the major late minimal promoter of adenovirus. Gal4 binding sites in the vector were replaced with 1 to 7 copies of the UL9 binding site.

The effect of the exogenously provided chimeric activator UL9–VP16 ("ULVP") on expression of four different engineered reporter constructs was evaluated. p5UL and p5ULE were engineered with the adeno major late minimal promoter fused to 5 tandem repeats of the UL9–21x response element and a firefly luciferase reporter in the pGL3-Basic or the pGL3Enhancer vector which has an SV40 enhancer, respectively. pULVP has a chimeric UL9/VP activator fused to a firefly luciferase reporter. p5Gal and p5GalE contain 5 tandem repeats of the Gal4 response element in place of the UL9–21x response element of p5UL and p5ULE, respectively. The promoterless pRL-Null plasmid containing the *Renilla* luciferase reporter was used as a copy number control.

HeLa cells ($5\times10^5$ cells) were co-transfected with 3 plasmids: 2 µg of reporter, 0.2 µg of pRL-Null co-reporter and varying amounts of pULVP (0 to 100 ng). Low concentrations of pULVP encoding the UL9–VP16 activator significantly increased the expression of specific reporter constructs that have UL9 response elements while non-specific reporter constructs were not activated significantly (Table 4). P5UL and p5ULE expression was increased 24 fold and 8 fold, respectively above basal expression, with 25 ng of pULVP. In contrast, 25 ng of pULVP activated p5Gal only 2 fold and did not activate p5GalE expression at all. SV40 enhancer in pSULE and p5GalE augmented the promoter activities 18 fold and 15-fold compared to the activities of comparable constructs with no enhancer (p5UL and p5Gal), respectively.

TABLE 4

Effect Of UL9-VP16 Activator On Reporter Expression

| Construct | no pULVP | pULVP (25 ng) | pULVP |
|---|---|---|---|
| p5UL | 1 x | 24 x | 31 x (1 ng), 77 x (20 ng) |
| p5ULE | 18 x | 138 x | ND[1] |
| p5Gal | 1 x | 2 x | ND |
| p5GalE | 15 x | 17 x | ND |
| pRL-Null | 1 x | 1.5–2.5 x | 3 x (10 ng) |

[1]ND = not done

The results indicate that exogenously provided ULVP acts as a transcriptional activator for promoters which have UL9 response elements. Further titration (0 to 40 ng) of pULVP was carried out to determine the optimal level of ULVP for the specific activation of p5UL and p5ULE. Based on firefly luciferase expression normalized by *Renilla* luciferase expression from pRL-Null, 1 ng of pULVP showed an activation level relative to p5ULE of over 30 fold. Expression of ULVP also increased expression of pRL-Null up to 3 fold increase was observed with 10 ng of pULVP. The non-normalized reporter activity indicated up to 77-fold activation of p5ULE with 20 ng of pULVP (Table 4).

The results show specific activation of expression by the ULVP activator promoter construct together with UL9 response elements.

$5\times10^4$ MCF7 cells were co-transfected with 3 µg of reporter, 0.5 µg of pRL-Null co-reporter and 20 ng of pULVP using 16 µg of LipofectAmine™ and 2 µl of Plus agent in a total volume of 0.4 ml in each well of a 24-well plate (1% fetal calf serum OPTI-DMEM medium). After 4 hours medium was changed to OPTI-DMEM containing 1% fetal calf serum plus varying amount of 21x. 20 ng of pULVP activator was shown to significantly increase the expression of p5UL which has UL9 response elements while the control reporter construct p5Gal was not activated significantly (FIG. 11). p5UL reporter expression in the presence of chimeric activator ULVP was down-regulated significantly with 21x treatment (7 fold at 20 µM 21x). The down-regulation was concentration dependent, suggesting that 21x displaced the ULVP chimeric activator from the promoter and that the 21x ligand response element was UL9 specific.

UL9 Repressor Construct

The sequence specific chimeric repressor, UL9-KRAB, was constructed the C-terminal DNA binding domain of UL9 fused to the N-terminus of the repressor domain of kruppel protein (KRAB, SEQ ID NO:10, Margolin JF, et al., 1994), expressed under the control of a CMV immediate early enhancer/promoter. Luciferase reporter constructs with a series of tandem repeated UL9 binding sites and flanking compound-binding sites were made by modifying the pG5luc vector (Promega). In this vector the firefly luciferase is under the control of synthetic promoter that is composed of five tandem repeated GAL4 binding sites followed by the major late minimal promoter of adenovirus. Gal4 binding sites in the vector were replaced with 1 to 7 copies of the UL9 binding site.

[1]ND=not done

The effect of the exogenously provided chimeric repressor UL9-KRAB ("ULKRAB") on expression of three different engineered reporter constructs was evaluated. p5ULE was engineered with the major late minimal promoter of adenovirus fused to 5 tandem repeats of the UL9–21x response element and a firefly luciferase reporter in the pGL3-Enhancer vector which has an SV40 enhancer. p5GalE has five tandem repeats of the GAL4 binding site followed by the major late minimal promoter of adenovirus and a firefly luciferase reporter in the pGL3-Enhancer vector which has an SV40 enhancer. The promoterless pRL-Null plasmid containing the *Renilla* luciferase reporter was used as a copy number control.

Previously expression of the chimeric ULKRAB repressor in HeLa cells exhibited specific repression of the p5ULE reporter activity by 6 fold (to 16% of basal level) in a triple plasmid co-transfection of plasmids pRL-SV40 copy control, co-reporter (15 ng), pSW5UL reporter (2 µg) and pULKRAB repressor (1 µg). The ULKRAB repressor plasmid was further titrated in a similar transfection assay to optimize the level of ULKRAB expression needed for specific repression of the pSW5ULE reporter. In this experiment 2 µg pSW5ULE reporter plasmid was co-transfected with varying amounts (0 to 2 µg) of pULKRAB plasmid and 0.2 µg of co-reporter pRL-Null. The basal activities of p5ULE and p5GalE were consistent with previous observations in the absence of pULKRAB (Table ULKRAB). Specific repression mediated by ULKRAB was observed: with 0.8 µg or more of pULKRAB pSW5UL was down regulated 20 fold (down to 5% of basal level). P5GalE was down regulated 1.7 fold (down to 62% of basal level) in the same experiment. Expression of up to 0.8 µg of pULKRAB did not affect the expression of pRL-Null significantly in triple plasmid co-transfection (data not shown).

TABLE 5

Effect Of UL9-KRAB Repressor On Reporter Expression

| Constructs | no pULKRAB | with pULKRAB (0.8 to about 1 µg) |
|---|---|---|
| p5ULE | 1x | 1/20x (5%) |
| p5GalE | 1x | 1/1.7x (62%) |
| pRL-Null | 1x | 1/1.3x |

EXAMPLE 2

Protein Displacement Studies with NF-KB

A purified Thioredoxin-p50 NF-kB fusion protein (p50C) (Genelabs Technologies, Inc.) was used to generate five oligonucleotides comprising an NF-kB DNA response element and one or two overlapping binding sites for the AT-rich binder, 21x.

The exemplified NF-kB binding sites, GGGACTTTCC (SEQ ID NO:29) and GGGATTTTCC (SEQ ID NO:30) are present in the Igk and IL-6 promoters, respectively. The exemplary oligonucleotides are presented in FIG. 7, with the transcriptional regulatory protein DNA response site indicated as bolded and uppercase, introduced compound binding sequences indicated in lowercase and potential compound binding sequences indicated as ( ) or [ ].

Oligonucleotides JF101 (SEQ ID NO:31) and 102 (SEQ ID NO:32), have compound binding sequences overlapping the right side of the NF-kB DNA response element, while in the case of JF103 (SEQ ID NO:33), the overlaps are from both sides (FIG. 7).

A gel mobility shift assay was carried out as described above for UL9, and the results presented in FIGS. 8A and B, indicated that: (1) 21x can efficiently displace NF-kB at concentrations as low as 1 µM, (2) the displacement is more efficient when the NF-kB binding site is an IL-6 sequence (SEQ ID NO:30) relative to an IgK sequence (SEQ ID NO:29), and (3) 21x displaces NF-kB more efficiently than distamycin.

The native CMV promoter has 3 NFKB response sites and 1 TATA binding protein (TBP) site. Purely engineered NF-kB/TBP based 21x ligand switchable constructs were created. In each of pMC, p2MC and p4MC, 0, 2 and 4 tandem repeats of a response element consisting of the NF-kB response sequence flanked by 21x sites were fused to a CMV minimal promoter with the TBP site modified to include a 9 A/T stretch to optimize 21x binding. These promoters were cloned into pGL3-Basic to create firefly luciferase reporter constructs, as set forth below.

Firefly luciferase reporter promoter constructs containing a minimal CMV system were constructed as follows:

pMC3 (SEQ ID NO:40), which includes a minimal CMV promoter with an introduced 21x site and a luciferase reporter; p2MC5 (SEQ ID NO:41), which includes a minimal CMV promoter with an introduced 21x site and a luciferase reporter and two NFKB sites; p4MC1 (SEQ ID NO:42), which includes a minimal CMV promoter with an introduced 21x site and a luciferase reporter plus four NFKB sites; pBKMC1 (SEQ ID NO:43), a wild type control vector which includes a minimal CMV promoter and a luciferase reporter and has a sequence of 8 to 9 A/T's near the TBP site; pBK2MC5 (SEQ ID NO:44), a control vector which includes a minimal CMV promoter, a luciferase reporter plus two tandem repeats of the NF-kB response element flanked by a poor 21x binding sequence and the flanking sequence of the TBP site was also modified to contain a 7 A/T stretch, which is less desirable for 21x binding; and pBK2MC12 (SEQ ID NO:45), a control vector which includes a minimal CMV promoter plus a luciferase reporter and two tandem repeats of the NF-kB response element.

Firefly luciferase reporter promoter constructs containing a complex CMV system were constructed as follows:

SWCMV (SEQ ID NO:46), which includes a native full CMV promoter with all 3 NFKB sites modified to contain introduced preferred binding sites for 21x and a luciferase reporter; MTCMV (SEQ ID NO:47), which includes a native full CMV promoter with all 3 NFKB sites and the TBP site modified to contain introduced preferred binding sites for 21x and a luciferase reporter; and BKCMV (SEQ ID NO:48), which includes a native full CMV promoter with 3 unmodified NFKB sites and an unmodified TBP site and a luciferase reporter.

The sequences of exemplary promoter constructs are provided below: pSWCMV (SEQ ID NO:46), as cloned in pGL3-Basic with KpnI and HindIII sites indicated as lowercase, ▓▓▓▓▓TCAATATTGGCCATTAGCCATATTATTCATTGGTTATATAGCAT
AAATTAATATTGGCTATTGGCCATTGCATACGTTGTATCTATATCATAA
TATGTACATTTATATTGGCTCATGTCCAATATGACCGCCATGTTGGCAT
TGATTATTGACTAGTTATTAATAGTAATCAATTACGGGGTCATTAGTTC
ATAGCCCATATATGGAGTTCCGCGTTACATAACTTACGGTAAATGGCCC
GCCTGGCTGACCGCCCAACGACCCCCGCCCATTGAC
GTCAATAATGACGTATGTTCCCATAGTAACGCAAATAGGGATTTTCCATT
AACGTCAATGGGTGGAGTATTTACGGTAAACTGCCCACTTGGCAGTACAT
CAAGTGTATCATATGCCAAGTCCGCCCCCTATTGACGTCAATGACGGTAA
ATGCCCGCCTGGCATTATGCCCAGTACATGACTTTATGGGATTTTCCTA
TTTGGCAGTACATCTACGTATTA
GTCATCGCTATTACCATGGTGATGCGGTTTTGGCAGTACACCAATGGGCG
TGGATAGCGGTTTGACTCACGGGGATTTCCAAGTCTCCACCCCATTGACG
TCAATGGGAGTTTGTTTTGGCACCAAGGTAAAAGGGATTTTCCAAAATGT
CGTAACAACTGCGATCGCCCGCCCCGTTGACGCAAATGGGCGGTAGGCGT
GTACGGTGGGAGGTTTATATAAGCAGAGCTCGTTTAGTGAACCGTCAGAT
C▓▓▓▓▓▓

MTCMV (SEQ ID NO:47), as cloned in pGL3-Basic with KpnI and HindIII sites indicated as lowercase, ▓▓▓▓▓TCAATATTGGCCATTAGCCATATTATTCATTGGTTATATAGCAT
AAATTAATATTGGCTATTGGCCATTGCATACGTTGTATCTATATCATAAT
ATGTACATTTATATTGGCTCATGTCCAATATGACCGCCATGTTGGCATTG
ATTATTGACTAGTTATTAATAGTAATCAATTACGGGGTCATTAGTTCATA
GCCCATATATGGAGTTCCGCGTTACAT
AACTTACGGTAAATGGCCCGCCTGGCTGACCGCCCAACGACCCCCGCCCA
TTGACGTCAATAATGACGTATGTTCCCATAGTAACGCAAATATTCCCGGG
AAATTAACGTCAATGGGTGGAGTATTTACGGTAAACTGCCCACTTGGCAG
TACATCAAGTGTATCATATGCCAAGTCCGCCCCCTATTGACGTCAATGAC
GGTAAATGCCCGCCTGGCATTATGCCCAGTACATGACTTTATTCTCGAG
GAATATTTGGCAGTACATCTACGTAT
TAGTCATCGCTATTACCATGGTGATGCGGTTTTGGCAGTACACCAATGGG
CGTGGATAGCGGTTTGACTCACGGGGATTTCCAAGTCTCCACCCCATTGA
CGTCAATGGGAGTTTGTTTTGGCACCAAGGTAAAATTACGCGTAAAAAAT
GTCGTAACAACTGCGATCGCCCGCCCCGTTGACGCAAATGGGCGGTAGGC
GTGTACGGTGGGAGGTTGCTAGCCGCAGAGCTCGTTTAGTGAACCGTCAG
ATC▓▓▓▓▓▓;

BKCMV, (SEQ ID NO:48), as cloned in pGL3-Basic with KpnI and HindIII sites indicated as lowercase, ▓▓▓▓▓TCAATATTGGCCATTAGCCATATTATTCATTGGTTATATAGCAT
AAATCAATATTGGCTATTGGCCATTGCATACGTTGTATCTATATCATAAT
ATGTACATTTATATTGGCTCATGTCCAATATGACCGCCATGTTGGCATTG
ATTATTGACTAGTTATTAATAGTAATCAATTACGGGGTCATTAGTTCATA
GCCCATATATGGAGTTCCGCGTTACAT -continued

```
AACTTACGGTAAATGGCCCGCCTGGCTGACCGCCCAACGACCCCCGCCCA

TTGACGTCAATAATGACGTATGTTCCCATAGTAACGCCAATAGGGACTTTC

CATTGACGTCAATGGGTGGAGTATTTACGGTAAACTGCCCACTTGGCAGT

ACATCAAGTGTATCATATGCCAAGTCCGCCCCCTATTGACGTCAATGACG

GTAAATGGCCCGCCTGGCATT
ATGCCCAGTACATGACCTTACGGGACTTTCCTACTTGGCACTACATCTACG

TATTAGTCATCGCTATTACCATGGTGATGCGGTTTTGGCAGTACACCAATG

GGCGTGGATAGCGGTTTGACTCACGGGGATTTCCAAGTCTCCACCCCATTG

ACGTCAATGGGAGTTTGTTTTGGCACCAAAATCAACGGGACTTTCCAAAAT

GTCGTAACAACTGCGATCGCCCGCCCCGTTGACGCAAATGGGCGGTAGGCG

TGTACGGTGGGAGGTCTATATAAGCAGAGCTCGTTTAGTGAACCGTCAGAT

C▓▓▓▓▓▓.
```

Expression of the firefly reporter using various engineered minimal CMV promoter constructs was analyzed in the presence or absence of various amount of exogenous NF-κB plasmid (pS50 and pS65 for the p50 and p65 NF-κB subunit, respectively). As shown in Table 6, the presence of NF-κB response elements in p2MC, p4MC, pBK2MC augmented the activity of the promoters approximately 4 to 17 fold relative to the activity of promoters lacking the NF-κB response element (pMC and PBKMC). This effect was incrementally increased based on the number of NF-κB response elements. These results suggest that NF-κB acted as the major activator for the promoters with NF-κB response element. Results are reported as normalized firefly luciferase activity relative to Renilla luciferase activity and as absolute firefly luciferase activity.

TABLE 6

Reporter Expression Regulated By NF-κB In A Minimal CMV System.

| Construct | endogenous NF kB | plus additional exogenous NF kB 0.1 μg (each of pS50 and pS65) |
|---|---|---|
| pMC3 | 1× (1×) | 2.2× (1.3×) |
| p2MC5 | 6× (12×) | 44× (32×) |
| p4MC1 | 17× (22×) | 85× (65×) |
| pBKMC1 | 1× (1.4×) | 1.4× (0.7×) |
| pBK2MC5 | 3.5× (3.8×) | 12× (5×) |
| pBK2MC12 | 4× (4.4×) | 18× (9×) |

As shown in Tables 6 and 7, the effect of additional exogenous NF-κB p50 and p65, expression following co-transfection, further increased the activity of all the promoter constructs which have NF-κB elements by approximately 4 to 7 fold. These results indicate that the endogenous intracellular NF-κB level is sub-optimal for the full activation of these engineered promoters. Additional expression of exogenous NF-κB did not significantly affect promoters without NF-κB element.

TABLE 7

Reporter Expression Regulated By NF-KB In A Complex CMV System.

| Construct | plus endogenous NF-kB |
|---|---|
| pBKCMV | 1× |
| pSWCMV | 1.2⁻1.6× |
| pMTCMV | 0.4⁻0.5× |

Firefly luciferase reporter expression results normalized relative to co-reporter Renilla luciferase to accommodate the differential transfection efficiency in each transfection. We have analyzed the effect of expression of exogenous NF-κB on Renilla luciferase co-reporter of pRL-Null. It was observed that with increasing amounts of NF-κB plasmid in all co-transfections, the level of Renilla luciferase expression was decreased 3 to 7 fold. The ideal copy and transfection control co-reporter is the one that is not affected either by the transcription factors or by the ligands. However, independent of the effect of NF-kB expression on the level of pRL-Null expression, absolute (un-normalized) expression of the firefly reporter showed a similar trend to normalized expression: that is addition of NF-kB response elements augmented the promoter activities of the reporter constructs and additional expression of exogenously provided NF-kB p50 and p65 increased the activity of the promoter in reporter constructs which had NF-kB response elements, indicating the endogenous level of NF-kB in HeLa cells is limiting for the full expression of the reporter constructs with NF-kB response element.

EXAMPLE 3

Protein Displacement Studies with Lacr

The feasibility of using LacR as an exogenous factor for a switch-on molecular switch system was evaluated using LacR, which is a repressor that represses transcription of the lac operon by binding to lacO operator sequences. Binding and displacement of LacR was tested using oligonucleotides with introduced drug binding sites that overlap the transcriptional regulatory protein binding site (FIG. 9).

In FIG. 9, both of oligonucleotides tested, SEQ ID NO:34 and SEQ ID NO:35, have introduced drug binding sites which overlap the LacR binding site on both sides of the lacO sequence.

A gel mobility shift assay was carried out as described above for UL9, and the results are presented in FIG. 10.

The results of the assay indicate that: (1) 21x can efficiently displace LacR, and that (2) 21x appears to displace LacR more efficiently than IPTG.

Preliminary experiments were carried out using reporter constructs. PBKLac has 3 wild type lacO response elements in an intron region of the RSV-LTR promoter fused to the firefly luciferase reporter gene. PSWLac has 3 modified lacO/21x response elements in place of wild type lacO sites. Basal activities of two clones each of pBKLac and pSWLac were determined. Two clones of pBKLac showed somewhat different activity. When compared to the expression of pBKLac34 (100%) pBKLac25 expression was 150%. Two pSWLac clones 27 and 30 each exhibited 71% and 83%, respectively. Two to four fold repression by exogenously supplied LacI was observed with as low as 0.1 μg of pLacI together with 2 μg of reporter construct.

EXAMPLE 4

Regulated Gene Expression in Prokaryotic Cells

The E. coli promoter rrnB P1 (SEQ ID NO:12), was selected as a prokaryotic model promoter for evaluating 21x in a cell-based aspect of the molecular switch system. The wild type UP element contains a 17 base pair stretch of AT-rich sequences, was used to test the effect of a DNA binding compound 21x, which preferably bind to AT-rich sequences (FIG. 2B, SEQ ID NO:13).

The effect of 21x on the interaction of the a subunit of RNAP with the rrnB P1 UP element was determined by evaluating the transcriptional activity of the promoter in several E. coli strains carrying a wild type or mutant rrnB P1 promoter fused to a lacZ reporter on its chromosome, as a phage monolysogen.

The promoters which were evaluated include a wild type rrnB P1 promoter (RLG3074, SEQ ID NO:15), which has a consensus UP sequence at a distal site, two mutant rrnB P1 promoters which have a consensus UP sequence at both proximal and distal sites (RLG4192, SEQ ID NO:16 and RLG4174, SEQ ID NO:17), and the "core" rrnB P1 promoter (RLG3097, SEQ ID NO:14), which functions as a negative control and lacks an UP sequence and a 21x binding site [Table 8 and FIG. 4A, wherein 21x binding sites are indicated as ( )].

TABLE 8

| | UP region sequence | | Relative Basal Activity |
|---|---|---|---|
| RLG 3097 | GACTGCAGTGGTACCTAGGAGG | (SEQ ID NO:14) | 1 X |
| RLG 3074 | AG(AAAATTATTTTAAATTT)CCT | (SEQ ID NO:15) | 30 X |
| RLG 4192 | GG(AAAATTTTTTTTCAAAA)GTA | (SEQ ID NO:16) | 110 X |
| RLG 4174 | TG(AAATTTATTTT)GCGAAAGGG | (SEQ ID NO:17) | 75 X |

Figure 4B:
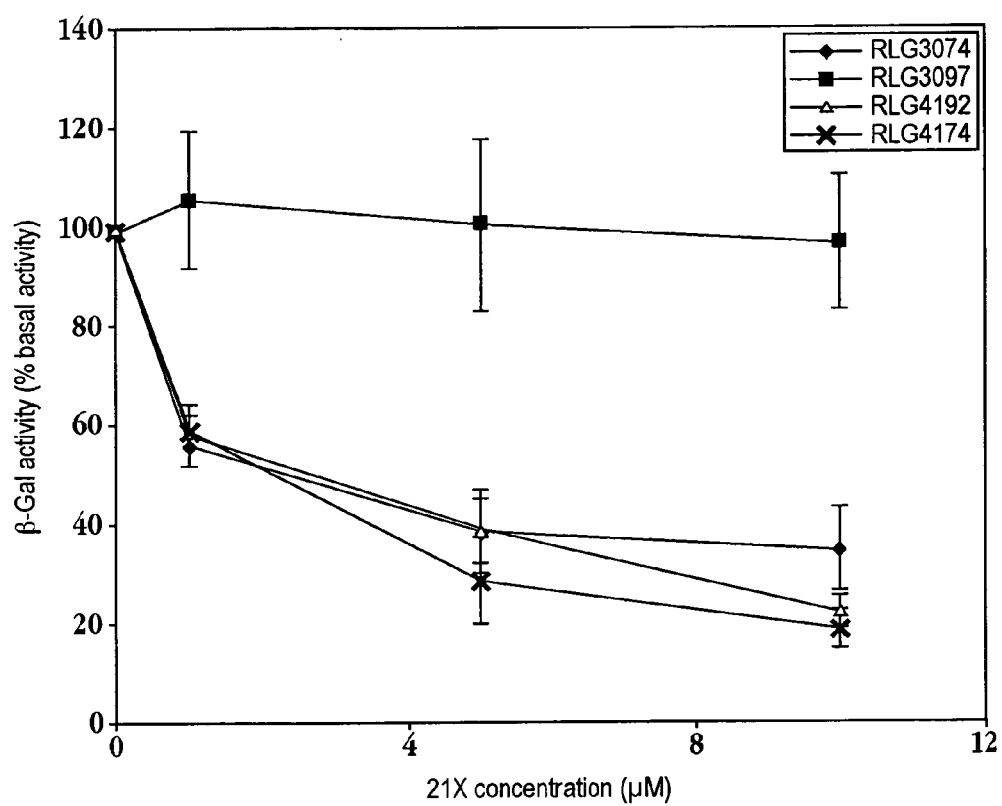
FIG. 4B depicts the effect of various concentrations of 21x on reporter expression in *E. coli* strains that carry rrnB P1 promoter constructs (the sequences for which are presented in FIG. 4A), fused to a lacZ reporter on the chromosome as a phage mono-lysogen, as indicated in the figure.

FIG. 4B shows the results of testing the activity of *E. coli* strains that carry the various rrnB P1 promoters fused to a lacZ reporter with 21X.

The promoter activity of RLG3097 (SEQ ID NO:14), which has the "core" sequence was not affected by 21x.

*E. coli* strains that carry rrnb P 1 promoters which have a distal UP element (RLG4174, SEQ ID NO:17) or both proximal and distal UP elements (RLG 3074, SEQ ID NO:15 and RLG4192, SEQ ID NO:16), exhibited similarly significant down-regulation of reporter gene expression, when treated with 21x.

The results indicate that targeting RNA polymerase α sites in the *E. coli* rrnB P 1 promoter with a small DNA-binding molecule, exemplified by 21x, may be used to effectively regulate prokaryotic gene expression in the chromosomal context.

Such targeting studies also suggest that a strong promoter like rrnB P1, and engineered variants thereof, can be down-regulated with a sequence preferential DNA-binding small molecule when the engineered promoter contains a small molecule binding sequence near the protein binding site.

EXAMPLE 5

Regulated Gene Expression Using the Cyclin D1 Promoter

A full-length 1900-bp fragment of the human cyclin D1 promoter representing nucleotides −1745 to +155 relative to the transcription start site and a series of cyclin D1 5' promoter deletions were constructed and PCR amplified. The −1745 wild-type and various site-directed mutants of the cyclin D1 promoter were inserted into the promoter-less firefly luciferase plasmid (pGL3-basic) and co-transfected into MCF7 cells human breast carcinoma cells, which over-express cyclin D1, together with an SV40 promoter driven *Renilla* luciferase control plasmid. Firefly luciferase activity for each construct was normalized to *Renilla* luciferase activity and compared to that of the full-length wild-type promoter (−1745). The data are presented as the mean+/−SEM for a minimum of two independent transfections done in triplicate. The promoter constructs were assayed in MCF7 cells, a second cyclin D1 overexpressing breast carcinoma cell line, ZR75; a breast cell line that expresses cyclin D1 normally, HMEC; a cyclin D1 overexpressing colon cancer cell line, HCT116; and a cyclin D1 overexpressing pancreatic cancer cell line, PANC-1.

The human breast carcinoma cell lines MCF7 and ZR75 were maintained in DMEM/F12 medium with 10% fetal bovine serum, 10 μg/ml bovine insulin and antibiotics (penicillin/streptomycin). The human colon carcinoma cell line HCT116 was maintained in McCoy's medium with 10% fetal bovine serum and pen/strep. The human pancreatic cell line PANC-1 was maintained in DMEM/F12 with 10% fetal bovine serum and pen/strep. Human mammary epithelial cells (HMEC) were maintained in Epithelial Growth Media supplemented with bovine pituitary extract (50 μg/ml), hydrocortisone (500ng/ml), hEGF (10 ng/ml), and insulin (5 μg/ml). All lines were maintained at 37° C., 5% $CO_2$. MCF7, ZR75, HCT116 and PANC-1 cells were purchased from the American Type Culture Collection. HMEC cells were purchased from Clonetics Corp.

Cells were transiently transfected with LipofectAMINE (GIBCO Life Sciences) in triplicate in 6-well tissue culture plates (Corning, N.Y.). Equal numbers of cells ($3 \times 10^5$/well) were seeded in each well, 24 hours prior to transfection. Prior to transfection, cells were equilibrated in 800 μl fresh medium (OptiMEM with 5% FBS and pen/strep). Cells were transfected with 5 μg of reporter plasmid containing a cyclin D1 promoter constructs in 200 μl transfection buffer. After 4 hours incubation with the transfection solution, cells were fed with 4 ml OptiMEM with 5% FBS and pen/strep. Cells were harvested 48 hours after transfection.

Following co-transfection into various cell lines, the cyclin D1 promoter constructs containing a mutation of the CRE and/or a mutation of the −30 to −21 region resulted in a reduction in luciferase activity, suggesting that both the CRE and the −30 to −21 sites are involved in transcriptional regulation of cyclin D1 basal expression in all of the overexpressing cancer cell lines tested, as well as in HMEC cells which express normal levels of cyclin D1.

Site-directed mutagenesis of the −30 to −21 promoter region was carried out and constructs assayed in MCF7 cells. The assay results indicate that bases between −30 and −24 (GAGTTTT SEQ ID NO:76) are the most important for transcriptional activation from this site (Table 9).

TABLE 9

Reporter Activity Of Cyclin D1 Promoter Constructs

| Construct | Mutations in -30-21 region | % Wild Type Activity |
|---|---|---|
| WT -1745 | GAGTTTTGTT (SEQ ID NO: 71) | 100 |
| -30 -21 -1745 | TCTGGGATCC (SEQ ID NO: 36) | 33 +/-2.2 |
| -30 -26 -1745 | TCTGGTTGTT (SEQ ID NO: 70) | 43 +/-3.5 |
| -25 -21 -1745 | GAGTTGGCGG (SEQ ID NO: 69) | 34 +/-4.7 |
| -30 -28 -1745 | TCTTTTGTT (SEQ ID NO: 68) | 33 +/-6.3 |
| -28 -23 -1745 | GATGGGATTT (SEQ ID NO: 67) | 46 +/-5.1 |
| -23 -21 -1745 | GAGTTTTTCC (SEQ ID NO: 66) | 138 +/-16.4 |
| 10 bp 21x -1745 | GAGTTTTTTTTAAG (SEQ ID NO: 37) | 87 +/-11.4 |
| 8 bp 21x -1745 | GAGTTTTAAAAGAG (SEQ ID NO: 38) | 85 +/-7.8 |

A dimer of netropsin, designated 21x, which has a high affinity for A/T-rich DNA sequences and has been shown to footprint a DNA site of about 10bp was used to regulate cyclin D1 promoter activity. A detailed biochemical characterization of 21x is provided in co-owned U.S. Ser. No. 06/154,415, expressly incorporated by reference herein.

Oligonucleotide binding sites for the netropsin dimer 21x, were introduced overlapping the −30 to −21 region of the CCND1 promoter. In one case, the site was introduced into the 3' end of the A/T-rich −30 to −21 site, by changing only 2 bp (10 bp 21x, SEQ ID NO:37). A second 21x binding site was constructed by mutating 5 bp of the wild-type promoter sequence to produce an uninterrupted 8 A/T stretch (8 bp 21x, SEQ ID NO:38). Binding of 21x to these sites was confirmed using a hybridization stabilization assay, as detailed herein and described in co-owned application U.S. Ser. No. 09/151,890 and U.S. Ser. No. 09/393,783, incorporated herein by reference. Both 21x site-containing constructs were cloned in the context of the −1745 cyclin D1 promoter in pGL3 basic, transfected into MCF7 cells and demonstrated to retain high levels of promoter activity in MCF7 cells in the absence of 21x (85% and 87% of wild-type promoter activity respectively).

When transiently transfected MCF7 cells were treated with 0, 1 or 10 μM 21x and assayed after 48 hr, activity of the wild-type cyclin D1 promoter constructs was unaffected by 21x, activity of the −30 to −21 mutant construct was approximately 25% of wild type and unaffected by 21x treatment, while both the 8 bp 21x (SEQ ID NO:38) and 10 bp 21x (SEQ ID NO:37) constructs showed reduced promoter activity at 1 μM 21x and levels as low as those of the −30 to −21 mutant construct at 10 μM 21x (FIG. 12).

The results of luciferase expression assays in mammalian MCF7 cells indicate that 21x treatment is effective to specifically lower cyclin D1 promoter activity 4-fold when a 21x-binding site is present overlapping the −30 to −21 transcriptional activator DNA response site, while promoter constructs lacking the 21x sites were unaffected (FIG. 12).

The results show that it is possible to specifically down-regulate overexpressed endogenous cyclin D1 in tumor cells by developing a DNA-binding compound with specificity for a regulatory sequence of the promoter.

EXAMPLE 6

Regulated Gene Expression Using the HBV core Promoter

A luciferase reporter construct was constructed with a linearized full-length copy of the HBV genome, with the core promoter positioned immediately upstream and driving the expression of the reporter. Mutagenic primers containing blocks of 15 nucleotides of targeted sequence mutation were designed to generate a series of linker scanner mutant promoter reporter clones using either a Morph™ (5' Prime to 3' Prime, Boulder, Colo.) or a QuikChange™ (Stratagene, La Jolla, Calif.) mutagenesis protocol.

Targeted segments of the promoter found to be resistant to mutagenesis were further sub-divided into smaller blocks of mutations consisting of 7–8 nucleotides. This series of linker scanner clones span the entire length of the core promoter segment. Mutagenic primers were also used to construct site-directed mutant constructs of known transcription factor binding sites including the hepatocyte nuclear factor sites, HNF3 and HNF4.

To determine potential critical regulatory elements in the core promoter, linker scanner analysis was performed using the series of systemic mutation clones constructed. Each linker scanner mutant construct was evaluated for promoter activity in transient transfection experiments based on luciferase reporter activity in the hepatoma-derived cell lines HepG2 and HuH7. The HBV stably-transfected cell lines, 22.1.5 and HepAD38, were also used in the linker scanner analysis. An increase or decrease in relative luciferase reporter activity relative to the wild type indicates potential presence of control elements critical to regulation of gene transcription.

Three regions of interest were identified by linker scanning analysis. All 3 regions align with cis-elements previously reported in the literature. One region contains sequences corresponding to a HNF4 transcription factor binding site (SEQ ID NO:50). A second region contains sequences corresponding to a proximal HNF3 transcription factor binding site (SEQ ID NO:48). Both of these protein factor sites have been described as important activation elements for the HBV core promoter. Mutation of a third region abolished the wild type TATA box sequence (SEQ ID NO:51) of the promoter. A second HNF3 site (Distal HNF3-1) has been reported, however, mutation of the distal HNF3 site did not show any adverse effects in promoter activity (Table 10).

TABLE 10

Reporter Analysis of Site-Directed Mutants of HNF3 and HNF4 Sites of the HBV Core Promoter.

| | Nucleotide Coordinates (HBV ayw Strain) | Site-Directed Mutant Sequence | Percent Wild Type HepAD38 |
| --- | --- | --- | --- |
| Distal HNF3 | 1680–1691 | CCAGGGCCCCGA (SEQ ID NO:72) | 102 |
| Proximal HNF3 | 1715–1726 | GCCGCGGTCTGT (SEQ ID NO:73) | 33 |
| HNF4 | 1661–1672 | CGTCCGCGGTGA (SEQ ID NO:74) | 29 |

Following identification of the TATA box and the HNF4 and proximal HNF3 sites as the control elements most critical for core promoter activity, transcriptional activation as a result of the binding of the TATA binding protein (TBP) and the HNF transcription factors was further studied. It will be appreciated that failure of these protein factors to bind would result in down-regulation of the promoter.

Small DNA-binding compounds were utilized to test their ability to alter the transcription level from wild type and engineered HBV core promoters, either by interference and/or displacement of protein factor binding to its cognate nucleotide binding sequences. The nucleotide composition at the core TATA box contains a run of seven (7) A and T bases that could serve as a binding site for the compound 21x, which exhibits a binding preference of A/T-rich sequences. As shown in Table 11, 21x down-regulated the core wild type promoter by approximately 50% in transient transfection assays at concentrations of 0.5–1 µM. An engineered promoter construct, TATA21xR (SEQ ID NO:52) was prepared containing an introduced 21x binding site located adjacent to and overlapping the TATA box sequence. The down-regulating effects were pronounced for cells transfected with the engineered TATA21xR construct, for which the reporter gene activity decreased by 4–5 fold, consistent with the premise that 21x may bind with higher affinity to the A/T-rich binding sequence present in TATA21xR than to the core TATA box native sequence, leading to enhanced interference and/or displacement of TBP binding to the DNA.

A promoter construct, TATAmut (SEQ ID NO:53), with the TATA box sequence mutated in a manner to abolish TBP binding exhibited a low level of transcription and was not responsive to 21x treatment. Another mutant construct, 3'TATAmut (SEQ ID NO:54), with a sequence alteration resulting in a shorter run of A/T nucleotides downstream of the TATA box also showed no effects upon 21x treatment. The DNA-binding compound (21x) is shown to be capable of altering levels of gene transcription through its interaction with a basal transcription factor.

As shown in Table 12 and FIG. 13, the DNA-binding compound GL046732 used to treat HepG2 cells transfected with wild type and engineered core promoter constructs, preferentially down-regulated the promoter activity of the TATARds1 clone (SEQ ID NO:55) in a dosage-dependent manner resulting in a 4 fold reduction in promoter activity at the 40 µM concentration. The promoter activity of clone TATARds3 (SEQ ID NO:57) was also affected, but the level of down-regulation observed was less of that seen for the "ds1" sequence. The core promoter activity of the wild type construct remained relatively unaffected.

TABLE 12

Effects of GL046732 on Promoter Activity of Core Promoter Constructs Containing Engineered Drug-Binding Sites

| Reporter Construct | Percent of no Drug Control | | |
|---|---|---|---|
| Wild type | 1 µM GL046732 | 10 µM GL046732 | 40 µM GL046732 |
| TATARds1 | 114 | 67 | 93 |
| TATARds2 | 56 | 39 | 25 |

TABLE 11

21x Down-regulates Expression of the HBV Core Promoter Through the TATA Box

| Reporter Construct | Sequence | Percent Wild Type Promoter Activity | |
|---|---|---|---|
| | | No Treatment | Treatment with 1 µM 21x |
| Wild type[2] | TACTAGGAGGCTGTAGGCATAAATTGGTCTGCGCACCAGCACCATG | 100 | 60 |
| TATA$_{mut}$[3] | TACTAGGA*TTAGTGCTTAAGCCC*TTGGTCTGCGCACCAGCACCATG | 15 | 13 |
| 3'TATA$_{mut}$[4] | TACTAGGAGGCTGTAGGCATAAA*GCTCGAGTATACAAC*GCACCATG | 31 | 36 |
| TATA$_{21XR}$[5] | TACTAGGAGGCTGTAGGCATAAATTAGTCTGCGCACCAGCACCATG | 98 | 21 |

[2]Wild type = wild type core promoter (SEQ ID NO:51)
[3]TATA$_{mut}$ = mutant construct with TATA (SEQ ID NO:53)
[4]3'TATA$_{mut}$ = mutant construct with 15 nucleotides downstream from TATA box mutated (SEQ ID NO:54)
[5]TATA$_{21xR}$ = construct with engineered 21x site on right side of TATA (SEQ ID NO:52)

Another DNA-binding compound, GL046732, was demonstrated to be effective in the regulation of promoter activity of HBV core promoter constructs with engineered compound binding sequences. Three types of potential compound binding sequences were designed and position-cloned to be adjacent and overlapping transcription factor recognition sites. The general designs of the three different types of potential compound binding sequences are (ds1) two core sequences of 5 A/T nucleotides on either end with a center block of 3 G/C nucleotides, (ds2) a run of 12 to 13 A/T nucleotides, and (ds3) a run of 8 to 9 A/T nucleotides. Exemplary promoter constructs include the following:

TABLE 12-continued

Effects of GL046732 on Promoter Activity of Core Promoter Constructs Containing Engineered Drug-Binding Sites

| Reporter Construct | Percent of no Drug Control | | |
|---|---|---|---|
| Wild type | 1 µM GL046732 | 10 µM GL046732 | 40 µM GL046732 |
| TATARds3 | 71 | 62 | 65 |
| | 102 | 73 | 39 |

TATARds1 TACTAGGAGGCTGTAGGCATAAATGCGTAAAAGCACCAGCACCATGCAAC (SEQ ID NO:55)

TATARds2 TACTAGGAGGCTGTAGGCATAAATTAAAAAACGCACCAGCACCATGCAAC (SEQ ID NO:56)

TATARds3 TACTAGGAGGCTGTAGGCATAAATTAATCCGCGCACCAGCACCATGCAAC (SEQ ID NO:57)

Similarly, ds1, ds2, and ds3 sequences were designed and placed adjacent and overlapping the proximal HNF3 site. Exemplary engineered sequences include the following:

```
HNF3Rds1 ACCTTGAGGCATACTTCAAAGACTGTTGATTTAGCGAATAAGAGGAGTTGG    (SEQ ID NO:58)

HNF3Rds2 ACCTTGAGGCATACTTCAAAGACTGTTTATTTTAATAACGGGAGGAGTTGG    (SEQ ID NO:59)

HNF3Rds3 ACCTTGAGGCATACTTCAAAGACTGTTTATTTAAGGACTGGGAGGAGTTGG    (SEQ ID NO:60)
```

Oligonucleotides containing these HNF3 engineered sequences were used along with a wild type oligomer in an in vitro gel mobility shift assay, and found to bind the HNF3 transcription factor specifically. GL046732 was then tested for its ability to bind to the engineered sequences and either cause displacement of HNF3 or prevent the transcription factor from binding. GL046732 was found to be most effective in displacement of protein-bound band in the gel shift assay with the same drug sequence (ds1). The $EC_{50}$ value for protein displacement was determined to be in the concentration range of 300–800 nM. Similar to the transfection results obtained from the TATAds constructs, GL046732 was also slightly effective in displacement of HNF3 with the ds3 type sequence, while having no effects on the wild type sequence.

These results, taken together, indicate that a compound binding site may be engineered into a promoter and thereby serves as a means for regulated gene expression of a coding sequence operably linked to it.

SEQUENCE LISTING TABLE
(all oligonucleotides shown as single stranded in 5' to 3' direction)

| Description | SEQ ID NO |
|---|---|
| UL9 DNA response element CGTTCGCACTT (11 bp) | 1 |
| GAL4 DNA response element CGGAGTACTGTCCTCCG (17 bp) | 2 |
| ZFHD1 DNA response element TAATTANGGGNG (12 bp) | 3 |
| NF-KB p65 Genbank Accession Number M62399, locus number HUMP65NFKB | 4 |
| tetO DNA response element TCCCTATCAGTGATAGAGA (19 bp) | 5 |
| lacO DNA response element CTTAACACTCG:CGAGTGTTAAG (22 bp) | 6 |
| Ecdysone receptor RG(GT)TCANTGA(CA)CY (15 bp) | 7 |
| VP16: aa 413–489 no sequence shown | 8 |
| VP64: tetramer of aa 437–447 of VP16 no sequence shown | 9 |
| KRAB: aa 1–97<br>MDAKSLTAWSRTLVTFKDVFVDFTREEWKLLDTAQQIVYRNVMLENYKNLVSLGYQLTKPDVILR<br>LEKGEEPWLVEREIHQETHPDSETAFEIKSSV | 10 |
| Mad: aa 1–36<br>MAAAVRMNIQMLLEAADYLERREREAEHGYASMLPY | 11 |
| Sequence of rrnB P1 promoter: from -66 to +50<br>CGCGGTCAGAAAATTATTTTAAATTTCCTCTTGTCAGGCCGGAATAACTCCCTATAA<br>TGCGCCACCACTGACACGGAACAACGGCAAACACGCCGCCGGGTCAGCGGGGTTCTC<br>CT | 12 |
| rrnB P1 promoter UP element AGAAAATTATTTTAAATTTCCT | 13 |
| RLG3097 (core) GACTGCAGTGGTACCTAGGAGG | 14 |
| RLG3074 (WILD TYPE) AG(AAAATTATTTTAAATTT)CCT | 15 |
| RLG4192 GG(AAAATTTTTTTTCAAAA)GTA | 16 |
| RLG4174 TG(AAATTTATTTT)GCGAAAGGG | 17 |
| modified UL-9 DNA response sequence TGTTCGCACTT | 18 |
| modified UL-9 DNA response sequence (YK 202LX, 52-mer)<br>CATGGACG CCACTG AGCCGtttt TGTTCGCACTT GAGGCGAGTCGATGCACC | 19 |
| modified UL-9 DNA response sequence (YK 202RX-A, 54-mer)<br>CATGGACG CCACTG AGCCG TGTTCGCACTT<br>tttttGAGGCGAGTCGATGCACC | 20 |
| modified UL-9 DNA response sequence (YK 202RX, 58-mer)<br>CATGGACG CCACTG AGCCGTTTT TGTTCGCACTT<br>tttttGAGGCGAGTCGATGCACC | 21 |
| MEF C(TTAAAAATAA)C | 22 |
| 780BP (TTGAAAAATCAA)CGCT | 23 |
| UL9 (modified) (ttttTGTT)CGCAC(TTttttt) | 24 |
| NFkB (modified) (tttttGGG[AtTTT)CCttttt] | 25 |
| lacO (modified) (aaaaAATT)GTGAGCGCTCAC(AATTtttt) | 26 |
| NtBBF1 (plant tissue-specific transcription factor) ACTTTA | 27 |
| DRE (plant element identified in the promoter region of the rd29A gene associated with dehydration and cold-induced gene expression) TACCGACAT | 28 |
| NF-kB DNA response sequence from Igk promoter: GGGACTTTCC | 29 |
| NF-kB DNA response sequence from IL-6 promoter: GGGATTTTCC | 30 |
| JF101 (NFKB1) (50mer) (right side)<br>cgac cgtgctcgag TTAACGGGACTTTCCAAaaa cgatcg gact ggactc | 31 |

SEQUENCE LISTING TABLE
(all oligonucleotides shown as single stranded in 5' to 3' direction)

| Description | SEQ ID NO |
|---|---|
| JF 102 (NFKB2) (60mer) (right side)<br>cgac cgtgctcgag TTAACGGGAtTTTCCAAaaa cgatcg gact ggactc | 32 |
| JF 103 (NFKB3) (60mer) (both sides)<br>cgac cgtgctcgag aaattGGGAtTTTCCAAaaa cgatcg gact ggactc | 33 |
| lacO aaaaAATTGTGAGCGCTCACAATTtttt | 34 |
| lacO ttttttTTGTGAGCGGATAACAAaa | 35 |
| Cyclin D1 -30-21 TCTGGGATCC | 36 |
| Cyclin D1 10bp 21x GAGTTTTTTTTAAG | 37 |
| Cyclin D1 8bp 21x GAGTTTTAAAAGAG | 38 |
| NFKB p50 Genbank Accession Number M55643, locus number HUMNFKB34 | 39 |
| pMC3 (NheI to BglI)<br>GCTAGCCCCGCCCCGTTGACGCAAATGGGCGGTAGGCGTGTACGGTGGGAGGTTTAT<br>ATAAGCAGAGCTCGTTTAGTGAACCGTCAGATCAGATCT | 40 |
| 2MC5 (NheI to BglI)<br>GCTAGCGCCCAAATTGGGATTTTCCAAAAAGCCGAAATTGGGATTTTCCAAAAACCG<br>CCGATCGCCCGCCCCGTTGACGCAAATGGGCGGTAGGCGTGTACGGTGGGAGGTTTA<br>TATAAGCAGAGCTCGTTTAGTGAACCGTCAGATCAGATCT | 41 |
| 4MC1 (MluII to BglI)<br>ACGCGTGCCCAAATTGGGATTTTCCAAAAAGCCGAAATTGGGATTTTCCAAAAACCG<br>CGCTAGCGCCCAAATTGGGATTTTCCAAAAAGCCGAAATTGGGATTTTCCAAAAACC<br>GCCGATCGCCCGCCCCGTTGACGCAAATGGGCGGTAGGCGTGTACGGTGGGAGGTTT<br>ATATAAGCAGAGCTCGTTTAGTGAACCGTCAGATCAGATCT | 42 |
| BKMC1 (NheI to BglI)<br>GCTAGCCCCGCCCCGTTGACGCAAATGGGCGGTAGGCGTGTACGGTGGGAGGTCTAT<br>ATAAGCAGAGCTCGTTTAGTGAACCGTCAGATCAGATCT | 43 |
| BK2MC5 (NheI to BglI)<br>GCTAGCGCCCAGGTCGGGATTTTCCGAGGAGCCGAGGTCGGGATTTTCCGAGGACCG<br>CCGATCGCCCGCCCCGTTGACGCAAATGGGCGGTAGGCGTGTACGGTGGGAGGCCTA<br>TATAAGCAGAGCTCGTTTAGTGAACCGTCAGATCAGATCT | 44 |
| BK2MC12 (NheI to BglI)<br>GCTAGCGCCCAGGTCGGGATTTTCCGAGGAGCCGAGGTCGGGATTTTCCGAGGACCG<br>CCGATCGCCCGCCCCGTTGACGCAAATGGGCGGTAGGCGTGTACGGTGGGAGGCCTA<br>TATAAGCAGAGCTCGTTTAGTGAACCGTCAGATCAGATCT | 45 |
| SWCMV | 46 |
| MTCMV | 47 |
| BKCMV | 48 |
| HBV core proximal, HNF3-2 binding site (GACTGTTTGTTT) | 49 |
| HBV core HNF4 binding site (AGGACTCTTGGA) | 50 |
| HBV core WT<br>TACTAGGAGGCTGTAGGCATAAATTGGTCTGCGCACCAGCACCATG | 51 |
| HBV core TATA21xR<br>TACTAGGAGGCTGTAGGCATAAATTAGTCTGCGCACCAGCACCATG | 52 |
| HBV core TATAmut<br>(TACTAGGA*TTAGTGCTTAAGCCC*TTGGTCTGCGCACCAGCACCATG) | 53 |
| HBV core 3'TATAmut<br>(TACTAGGAGGCTGTAGGCATAAA*GCTCGAGTATACAAC*GCACCATG) | 54 |
| HBV core TATARds1<br>TACTAGGAGGCTGTAGGCATAAATGCGTAAAAGCACCAGCACCATGCAAC | 55 |
| HBV core TATARds2<br>TACTAGGAGGCTGTAGGCATAAATTAAAAAACGCACCAGCACCATGCAAC | 56 |
| HBV core TATARds3<br>TACTAGGAGGCTGTAGGCATAAATTAATCCGCGCACCAGCACCATGCAAC | 57 |
| HNF3Rds1<br>ACCTTGAGGCATACTTCAAAGACTGTTGATTTAGCGAATAAGAGGAGTTGG | 58 |
| HNF3Rds2<br>ACCTTGAGGCATACTTCAAAGACTGTTTATTTTAATAACGGGAGGAGTTGG | 59 |
| HNF3Rds3<br>ACCTTGAGGCATACTTCAAAGACTGTTTATTTAAGGACTGGGAGGAGTTGG | 60 |
| pACTULVP activator construct-FIGS. 14A/B | 61 |
| pACT ULKRAB repressor construct-FIGS. 15A/B | 62 |

It is claimed:

1. A method of producing a cell having a molecular switch for modulating gene expression, said method comprising:
   (i) transforming said cell with a nucleic acid construct having a DNA response element which binds a transcriptional regulatory protein operably linked to a promoter, a non-native compound-binding sequence which is the same as, overlapping, or adjacent to said DNA response element for binding to a DNA binding compound, and a transgene under the control of said first promoter, wherein the DNA binding compound is seperate and different from the transcriptional regulatory protein; and
   (ii) exposing said transformed cell to a DNA binding compound, wherein binding of the DNA binding compound to said compound binding sequence is effective to inhibit binding of a transcriptional regulatory protein to the DNA response element, thereby derepressing or deactivating expression of the gene, where the transcriptional regulatory protein is a repressor or activator protein, respectively.

2. The method of claim 1, comprising:
   (iii) further transforming said cell with a second nucleic acid construct having a nucleic acid sequence encoding a transcriptional regulatory protein operably linked to a second promoter.

3. A molecular switch, comprising:
   (a) a first nucleic acid construct, having
      (i) a DNA response element for a transcriptional regulatory protein, operably linked to a first promoter;
      (ii) a non-native compound binding sequence which is the same as, overlapping, or adjacent to said DNA response element, for binding to a DNA binding compound;
      (iii) a transgene under the control of said first promoter; and
   (b) a DNA binding compound, wherein the DNA binding compound is seperate and different from the transcriptional regulatory protein; and
   (c) a second nucleic acid construct, having the coding sequence for said transcriptional regulatory protein operably linked to a second promoter;
   wherein said DNA binding compound, when bound to said binding sequence, is effective to modulate binding of said transcriptional regulatory protein to said DNA response element and wherein a first vector is including said first nucleic acid construct and a second vector is including said second nucleic acid construct.

4. A molecular switch, comprising:
   (a) a first nucleic acid construct, having
      (i) a DNA response element for a transcriptional regulatory protein, operably linked to a first promoter;
      (ii) a non-native compound binding sequence which is the same as, overlapping, or adjacent to said DNA response element, for binding to a DNA binding compound;
      (iii) a transgene under the control of said first promoter; and
   (b) a DNA binding compound, wherein the DNA binding compound is seperate and different from the transcriptional regulatory protein;
   wherein said DNA binding compound, when bound to said binding sequence, is effective to modulate binding of said transcriptional regulatory protein to said DNA response element and wherein said compound binding sequence has from about 8 to 20 nucleotides.

5. A molecular switch, comprising:
   (a) a first nucleic acid construct, having
      (i) a DNA response element for a transcriptional regulatory protein, operably linked to a first promoter;
      (ii) a non-native compound binding sequence which is the same as, overlapping, or adjacent to said DNA response element, for binding to a DNA binding compound;
      (iii) a transgene under the control of said first promoter; and
   (b) a DNA binding compound, wherein the DNA binding compound is seperate and different from the transcriptional regulatory protein;
   wherein said DNA binding compound, when bound to said binding sequence, is effective to modulate binding of said transcriptional regulatory protein to said DNA response element and wherein said nucleic acid construct has from 1 to 12 compound binding sequences.

6. A molecular switch, comprising:
   (a) a first nucleic acid construct, having
      (i) a DNA response element for a transcriptional regulatory protein, operably linked to a first promoter;
      (ii) a non-native compound binding sequence which is the same as, overlapping, or adjacent to said DNA response element, for binding to a DNA binding compound;
      (iii) a transgene under the control of said first promoter; and
   (b) a DNA binding compound, wherein the DNA binding compound is seperate and different from the transcriptional regulatory protein;
   wherein said DNA binding compound, when bound to said binding sequence, is effective to modulate binding of said transcriptional regulatory protein to said DNA response element and wherein said nucleic acid construct has from 1 to 12 tandem repeated transcriptional regulatory protein DNA response elements.

* * * * *

SEQUENCE LISTING

<160> NUMBER OF SEQ ID NOS: 77

<210> SEQ ID NO 1
<211> LENGTH: 11
<212> TYPE: DNA

-continued

```
<213> ORGANISM: Artificial Sequence
<220> FEATURE:
<223> OTHER INFORMATION: DNA response element

<400> SEQUENCE: 1
cgttcgcact t                                                            11

<210> SEQ ID NO 2
<211> LENGTH: 17
<212> TYPE: DNA
<213> ORGANISM: Artificial Sequence
<220> FEATURE:
<223> OTHER INFORMATION: DNA response element

<400> SEQUENCE: 2
cggagtactg tcctccg                                                      17

<210> SEQ ID NO 3
<211> LENGTH: 12
<212> TYPE: DNA
<213> ORGANISM: Artificial Sequence
<220> FEATURE:
<223> OTHER INFORMATION: DNA response element
<220> FEATURE:
<221> NAME/KEY: misc_feature
<222> LOCATION: (1)...(12)
<223> OTHER INFORMATION: n = A,T,C or G

<400> SEQUENCE: 3
taattanggg ng                                                           12

<210> SEQ ID NO 4
<211> LENGTH: 551
<212> TYPE: PRT
<213> ORGANISM: Homo sapiens
<220> FEATURE:
<221> NAME/KEY: VARIANT
<222> LOCATION: (0)...(0)
<223> OTHER INFORMATION: transcriptional regulatory protein

<400> SEQUENCE: 4

Met Asp Glu Leu Phe Pro Leu Ile Phe Pro Ala Glu Pro Ala Gln Ala
 1               5                  10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
```

```
                   165                 170                 175
Pro Val Leu Pro His Pro Ile Phe Asp Asn Arg Ala Pro Asn Thr Ala
                180                 185                 190
Glu Leu Lys Ile Cys Arg Val Asn Arg Asn Ser Gly Ser Cys Leu Gly
            195                 200                 205
Gly Asp Glu Ile Phe Leu Leu Cys Asp Lys Val Gln Lys Glu Asp Ile
        210                 215                 220
Glu Val Tyr Phe Thr Gly Pro Gly Trp Glu Ala Arg Gly Ser Phe Ser
225                 230                 235                 240
Gln Ala Asp Val His Arg Gln Val Ala Ile Val Phe Arg Thr Pro Pro
                245                 250                 255
Tyr Ala Asp Pro Ser Leu Gln Ala Pro Val Arg Val Ser Met Gln Leu
                260                 265                 270
Arg Arg Pro Ser Asp Arg Glu Leu Ser Glu Pro Met Glu Phe Gln Tyr
            275                 280                 285
Leu Pro Asp Thr Asp Asp Arg His Arg Ile Glu Glu Lys Arg Lys Arg
        290                 295                 300
Thr Tyr Glu Thr Phe Lys Ser Ile Met Lys Lys Ser Pro Phe Ser Gly
305                 310                 315                 320
Pro Thr Asp Pro Arg Pro Pro Arg Arg Ile Ala Val Pro Ser Arg
                325                 330                 335
Ser Ser Ala Ser Val Pro Lys Pro Ala Pro Gln Pro Tyr Pro Phe Thr
                340                 345                 350
Ser Ser Leu Ser Thr Ile Asn Tyr Asp Glu Phe Pro Thr Met Val Phe
            355                 360                 365
Pro Ser Gly Gln Ile Ser Gln Ala Ser Ala Leu Ala Pro Ala Pro Pro
        370                 375                 380
Gln Val Leu Pro Gln Ala Pro Ala Pro Ala Pro Ala Pro Ala Met Val
385                 390                 395                 400
Ser Ala Leu Ala Gln Ala Pro Ala Pro Val Pro Val Leu Ala Pro Gly
                405                 410                 415
Pro Pro Gln Ala Val Ala Pro Pro Ala Pro Lys Pro Thr Gln Ala Gly
                420                 425                 430
Glu Gly Thr Leu Ser Glu Ala Leu Leu Gln Leu Gln Phe Asp Asp Glu
            435                 440                 445
Asp Leu Gly Ala Leu Leu Gly Asn Ser Thr Asp Pro Ala Val Phe Thr
        450                 455                 460
Asp Leu Ala Ser Val Asp Asn Ser Glu Phe Gln Gln Leu Leu Asn Gln
465                 470                 475                 480
Gly Ile Pro Val Ala Pro His Thr Thr Glu Pro Met Leu Met Glu Tyr
                485                 490                 495
Pro Glu Ala Ile Thr Arg Leu Val Thr Gly Ala Gln Arg Pro Pro Asp
                500                 505                 510
Pro Ala Pro Ala Pro Leu Gly Ala Pro Gly Leu Pro Asn Gly Leu Leu
            515                 520                 525
Ser Gly Asp Glu Asp Phe Ser Ser Ile Ala Asp Met Asp Phe Ser Ala
        530                 535                 540
Leu Leu Ser Gln Ile Ser Ser
545                 550

<210> SEQ ID NO 5
<211> LENGTH: 19
<212> TYPE: DNA
<213> ORGANISM: Artificial Sequence
```

```
<220> FEATURE:
<223> OTHER INFORMATION: DNA response element

<400> SEQUENCE: 5
tccctatcag tgatagaga                                                  19

<210> SEQ ID NO 6
<211> LENGTH: 22
<212> TYPE: DNA
<213> ORGANISM: Artificial Sequence
<220> FEATURE:
<223> OTHER INFORMATION: response element

<400> SEQUENCE: 6
cttaacactc gcgagtgtta ag                                              22

<210> SEQ ID NO 7
<211> LENGTH: 13
<212> TYPE: DNA
<213> ORGANISM: Artificial Sequence
<220> FEATURE:
<223> OTHER INFORMATION: response element
<220> FEATURE:
<221> NAME/KEY: misc_feature
<222> LOCATION: (3)...(3)
<223> OTHER INFORMATION: n = G or T
<220> FEATURE:
<221> NAME/KEY: misc_feature
<222> LOCATION: (7)...(7)
<223> OTHER INFORMATION: n = A,T,C or G
<220> FEATURE:
<221> NAME/KEY: misc_feature
<222> LOCATION: (12)...(12)
<223> OTHER INFORMATION: n = A or C

<400> SEQUENCE: 7
rgntcantga cny                                                        13

<210> SEQ ID NO 8
<211> LENGTH: 77
<212> TYPE: PRT
<213> ORGANISM: Artificial Sequence
<220> FEATURE:
<223> OTHER INFORMATION: activator sequence

<400> SEQUENCE: 8

Ala Pro Pro Thr Asp Val Ser Leu Gly Asp Glu Leu His Leu Asp Gly
 1               5                  10                  15

Glu Asp Val Ala Met Ala His Ala Asp Ala Leu Asp Asp Phe Asp Leu
            20                  25                  30

Asp Met Leu Gly Asp Gly Asp Ser Pro Gly Pro Gly Phe Thr Pro His
        35                  40                  45

Asp Ser Ala Pro Tyr Gly Ala Leu Asp Met Ala Asp Phe Glu Phe Glu
    50                  55                  60

Gln Met Phe Thr Asp Ala Leu Gly Ile Asp Glu Tyr Gly
65                  70                  75

<210> SEQ ID NO 9
<211> LENGTH: 11
<212> TYPE: PRT
<213> ORGANISM: Artificial Sequence
<220> FEATURE:
<223> OTHER INFORMATION: activator sequence
<220> FEATURE:
<221> NAME/KEY: VARIANT
<222> LOCATION: (1)...(11)
<223> OTHER INFORMATION: tetramer
```

```
<400> SEQUENCE: 9

Asp Ala Leu Asp Asp Phe Asp Leu Asp Met Leu
1               5                   10

<210> SEQ ID NO 10
<211> LENGTH: 97
<212> TYPE: PRT
<213> ORGANISM: Artificial Sequence
<220> FEATURE:
<223> OTHER INFORMATION: repressor sequence

<400> SEQUENCE: 10

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
                20                  25                  30

Thr Ala Gln Gln Ile Val Tyr Arg Asn Val Met Leu Glu Asn Tyr Lys
            35                  40                  45

Asn Leu Val Ser Leu Gly Tyr Gln Leu Thr Lys Pro Asp Val Ile Leu
        50                  55                  60

Arg Leu Glu Lys Gly Glu Glu Pro Trp Leu Val Arg Glu Ile His
65                  70                  75                  80

Gln Glu Thr His Pro Asp Ser Glu Thr Ala Phe Glu Ile Lys Ser Ser
                85                  90                  95

Val

<210> SEQ ID NO 11
<211> LENGTH: 36
<212> TYPE: PRT
<213> ORGANISM: Artificial Sequence
<220> FEATURE:
<223> OTHER INFORMATION: repressor sequence

<400> SEQUENCE: 11

Met Ala Ala Ala Val Arg Met Asn Ile Gln Met Leu Leu Glu Ala Ala
1               5                   10                  15

Asp Tyr Leu Glu Arg Arg Glu Arg Glu Ala Glu His Gly Tyr Ala Ser
                20                  25                  30

Met Leu Pro Tyr
            35

<210> SEQ ID NO 12
<211> LENGTH: 116
<212> TYPE: DNA
<213> ORGANISM: Escherichia coli
<220> FEATURE:
<221> NAME/KEY: misc_feature
<222> LOCATION: (0)...(0)
<223> OTHER INFORMATION: partial promoter sequence

<400> SEQUENCE: 12
cgcggtcaga aaattatttt aaatttcctc ttgtcaggcc ggaataactc cctataatgc      60
gccaccactg acacggaaca acggcaaaca cgccgccggg tcagcggggt tctcct        116

<210> SEQ ID NO 13
<211> LENGTH: 22
<212> TYPE: DNA
<213> ORGANISM: Escherichia coli
<220> FEATURE:
<221> NAME/KEY: misc_feature
<222> LOCATION: (0)...(0)
```

-continued

<223> OTHER INFORMATION: partial promoter sequence

<400> SEQUENCE: 13
agaaaattat tttaaatttc ct                                          22

<210> SEQ ID NO 14
<211> LENGTH: 22
<212> TYPE: DNA
<213> ORGANISM: Artificial Sequence
<220> FEATURE:
<223> OTHER INFORMATION: modified promoter sequence

<400> SEQUENCE: 14
gactgcagtg gtacctagga gg                                          22

<210> SEQ ID NO 15
<211> LENGTH: 22
<212> TYPE: DNA
<213> ORGANISM: Artificial Sequence
<220> FEATURE:
<223> OTHER INFORMATION: modified promoter sequence

<400> SEQUENCE: 15
agaaaattat tttaaatttc ct                                          22

<210> SEQ ID NO 16
<211> LENGTH: 22
<212> TYPE: DNA
<213> ORGANISM: Artificial Sequence
<220> FEATURE:
<223> OTHER INFORMATION: modified promoter sequence

<400> SEQUENCE: 16
ggaaaatttt ttttcaaaag ta                                          22

<210> SEQ ID NO 17
<211> LENGTH: 22
<212> TYPE: DNA
<213> ORGANISM: Artificial Sequence
<220> FEATURE:
<223> OTHER INFORMATION: modified promoter sequence

<400> SEQUENCE: 17
tgaaatttat tttgcgaaag gg                                          22

<210> SEQ ID NO 18
<211> LENGTH: 11
<212> TYPE: DNA
<213> ORGANISM: Artificial Sequence
<220> FEATURE:
<223> OTHER INFORMATION: engineered DNA response element

<400> SEQUENCE: 18
tgttcgcact t                                                      11

<210> SEQ ID NO 19
<211> LENGTH: 52
<212> TYPE: DNA
<213> ORGANISM: Artificial Sequence
<220> FEATURE:
<223> OTHER INFORMATION: engineered DNA response element

<400> SEQUENCE: 19
catggacgcc actgagccgt ttttgttcgc acttgaggcg agtcgatgca cc          52

```
<210> SEQ ID NO 20
<211> LENGTH: 54
<212> TYPE: DNA
<213> ORGANISM: Artificial Sequence
<220> FEATURE:
<223> OTHER INFORMATION: engineered DNA response element

<400> SEQUENCE: 20
catggacgcc actgagccgt gttcgcactt tttttgagg cgagtcgatg cacc        54

<210> SEQ ID NO 21
<211> LENGTH: 58
<212> TYPE: DNA
<213> ORGANISM: Artificial Sequence
<220> FEATURE:
<223> OTHER INFORMATION: engineered DNA response element

<400> SEQUENCE: 21
catggacgcc actgagccgt ttttgttcgc acttttttttt gaggcgagtc gatgcacc   58

<210> SEQ ID NO 22
<211> LENGTH: 12
<212> TYPE: DNA
<213> ORGANISM: Artificial Sequence
<220> FEATURE:
<223> OTHER INFORMATION: engineered DNA response element

<400> SEQUENCE: 22
cttaaaaata ac                                                     12

<210> SEQ ID NO 23
<211> LENGTH: 16
<212> TYPE: DNA
<213> ORGANISM: Artificial Sequence
<220> FEATURE:
<223> OTHER INFORMATION: engineered DNA response element

<400> SEQUENCE: 23
ttgaaaaatc aacgct                                                 16

<210> SEQ ID NO 24
<211> LENGTH: 21
<212> TYPE: DNA
<213> ORGANISM: Artificial Sequence
<220> FEATURE:
<223> OTHER INFORMATION: engineered DNA response element

<400> SEQUENCE: 24
tttttgttcg cactttttt t                                            21

<210> SEQ ID NO 25
<211> LENGTH: 20
<212> TYPE: DNA
<213> ORGANISM: Artificial Sequence
<220> FEATURE:
<223> OTHER INFORMATION: engineered DNA response element

<400> SEQUENCE: 25
tttttgggat tttccttttt                                             20

<210> SEQ ID NO 26
<211> LENGTH: 28
<212> TYPE: DNA
<213> ORGANISM: Artificial Sequence
<220> FEATURE:
<223> OTHER INFORMATION: engineered DNA response element
```

```
<400> SEQUENCE: 26
aaaaaattgt gagcgctcac aatttttt                                          28

<210> SEQ ID NO 27
<211> LENGTH: 6
<212> TYPE: DNA
<213> ORGANISM: Artificial Sequence
<220> FEATURE:
<223> OTHER INFORMATION: tissue-specific transcription factor

<400> SEQUENCE: 27 acttta                                                                  6

<210> SEQ ID NO 28
<211> LENGTH: 9
<212> TYPE: DNA
<213> ORGANISM: Artificial Sequence
<220> FEATURE:
<223> OTHER INFORMATION: engineered DNA response element

<400> SEQUENCE: 28 taccgacat                                                               9

<210> SEQ ID NO 29
<211> LENGTH: 10
<212> TYPE: DNA
<213> ORGANISM: Artificial Sequence
<220> FEATURE:
<223> OTHER INFORMATION: engineered DNA response element

<400> SEQUENCE: 29
gggactttcc                                                              10

<210> SEQ ID NO 30
<211> LENGTH: 10
<212> TYPE: DNA
<213> ORGANISM: Artificial Sequence
<220> FEATURE:
<223> OTHER INFORMATION: engineered DNA response element

<400> SEQUENCE: 30
gggattttcc                                                              10

<210> SEQ ID NO 31
<211> LENGTH: 50
<212> TYPE: DNA
<213> ORGANISM: Artificial Sequence
<220> FEATURE:
<223> OTHER INFORMATION: engineered DNA response element

<400> SEQUENCE: 31
cgaccgtgct cgagttaacg ggactttcca aaaacgatcg gactggactc                  50

<210> SEQ ID NO 32
<211> LENGTH: 50
<212> TYPE: DNA
<213> ORGANISM: Artificial Sequence
<220> FEATURE:
<223> OTHER INFORMATION: engineered DNA response element

<400> SEQUENCE: 32
cgaccgtgct cgagttaacg ggattttcca aaaacgatcg gactggactc                  50

<210> SEQ ID NO 33
<211> LENGTH: 50
```

```
<210> SEQ ID NO 33
<211> LENGTH: 50
<212> TYPE: DNA
<213> ORGANISM: Artificial Sequence
<220> FEATURE:
<223> OTHER INFORMATION: engineered DNA response element

<400> SEQUENCE: 33
cgaccgtgct cgagaaattg ggattttcca aaaacgatcg gactggactc         50

<210> SEQ ID NO 34
<211> LENGTH: 28
<212> TYPE: DNA
<213> ORGANISM: Artificial Sequence
<220> FEATURE:
<223> OTHER INFORMATION: engineered DNA response element

<400> SEQUENCE: 34
aaaaaattgt gagcgctcac aatttttt                                 28

<210> SEQ ID NO 35
<211> LENGTH: 25
<212> TYPE: DNA
<213> ORGANISM: Artificial Sequence
<220> FEATURE:
<223> OTHER INFORMATION: engineered DNA response element

<400> SEQUENCE: 35
ttttttttgt gagcggataa caaaa                                    25

<210> SEQ ID NO 36
<211> LENGTH: 10
<212> TYPE: DNA
<213> ORGANISM: Artificial Sequence
<220> FEATURE:
<223> OTHER INFORMATION: engineered DNA response element

<400> SEQUENCE: 36
tctgggatcc                                                     10

<210> SEQ ID NO 37
<211> LENGTH: 14
<212> TYPE: DNA
<213> ORGANISM: Artificial Sequence
<220> FEATURE:
<223> OTHER INFORMATION: engineered DNA response element

<400> SEQUENCE: 37
gagttttttt taag                                                14

<210> SEQ ID NO 38
<211> LENGTH: 14
<212> TYPE: DNA
<213> ORGANISM: Artificial Sequence
<220> FEATURE:
<223> OTHER INFORMATION: engineered DNA response element

<400> SEQUENCE: 38
gagttttaaa agag                                                14

<210> SEQ ID NO 39
<211> LENGTH: 969
<212> TYPE: PRT
<213> ORGANISM: Homo sapiens
<220> FEATURE:
<221> NAME/KEY: VARIANT
<222> LOCATION: (0)...(0)
<223> OTHER INFORMATION: transcriptional regulatory protein
```

<400> SEQUENCE: 39

```
Met Ala Glu Asp Asp Pro Tyr Leu Gly Arg Pro Glu Gln Met Phe His
 1               5                   10                  15
Leu Asp Pro Ser Leu Thr His Thr Ile Phe Asn Pro Glu Val Phe Gln
            20                  25                  30
Pro Gln Met Ala Leu Pro Thr Ala Asp Gly Pro Tyr Leu Gln Ile Leu
        35                  40                  45
Glu Gln Pro Lys Gln Arg Gly Phe Arg Phe Arg Tyr Val Cys Glu Gly
50                  55                  60
Pro Ser His Gly Gly Leu Pro Gly Ala Ser Ser Glu Lys Asn Lys Lys
65                  70                  75                  80
Ser Tyr Pro Gln Val Lys Ile Cys Asn Tyr Val Gly Pro Ala Lys Val
                85                  90                  95
Ile Val Gln Leu Val Thr Asn Gly Lys Asn Ile His Leu His Ala His
            100                 105                 110
Ser Leu Val Gly Lys His Cys Glu Asp Gly Ile Cys Thr Val Thr Ala
        115                 120                 125
Gly Pro Lys Asp Met Val Val Gly Phe Ala Asn Leu Gly Ile Leu His
130                 135                 140
Val Thr Lys Lys Lys Val Phe Glu Thr Leu Glu Ala Arg Met Thr Glu
145                 150                 155                 160
Ala Cys Ile Arg Gly Tyr Asn Pro Gly Leu Leu Val His Pro Asp Leu
                165                 170                 175
Ala Tyr Leu Gln Ala Glu Gly Gly Asp Arg Gln Leu Gly Asp Arg
            180                 185                 190
Glu Lys Glu Leu Ile Arg Gln Ala Ala Leu Gln Gln Thr Lys Glu Met
        195                 200                 205
Asp Leu Ser Val Val Arg Leu Met Phe Thr Ala Phe Leu Pro Asp Ser
210                 215                 220
Thr Gly Ser Phe Thr Arg Arg Leu Glu Pro Val Val Ser Asp Ala Ile
225                 230                 235                 240
Tyr Asp Ser Lys Ala Pro Asn Ala Ser Asn Leu Lys Ile Val Arg Met
                245                 250                 255
Asp Arg Thr Ala Gly Cys Val Thr Gly Gly Glu Glu Ile Tyr Leu Leu
            260                 265                 270
Cys Asp Lys Val Gln Lys Asp Asp Ile Gln Ile Arg Phe Tyr Glu Glu
        275                 280                 285
Glu Glu Asn Gly Gly Val Trp Glu Gly Phe Gly Asp Phe Ser Pro Thr
290                 295                 300
Asp Val His Arg Gln Phe Ala Ile Val Phe Lys Thr Pro Lys Tyr Lys
305                 310                 315                 320
Asp Ile Asn Ile Thr Lys Pro Ala Ser Val Phe Val Gln Leu Arg Arg
                325                 330                 335
Lys Ser Asp Leu Glu Thr Ser Glu Pro Lys Pro Phe Leu Tyr Tyr Pro
            340                 345                 350
Glu Ile Lys Asp Lys Glu Glu Val Gln Arg Lys Arg Gln Lys Leu Met
        355                 360                 365
Pro Asn Phe Ser Asp Ser Phe Gly Gly Gly Ser Gly Ala Gly Ala Gly
370                 375                 380
Gly Gly Gly Met Phe Gly Ser Gly Gly Gly Gly Gly Thr Gly Ser
385                 390                 395                 400
Thr Gly Pro Gly Tyr Ser Phe Pro His Tyr Gly Phe Pro Thr Tyr Gly
                405                 410                 415
```

```
Gly Ile Thr Phe His Pro Gly Thr Thr Lys Ser Asn Ala Gly Met Lys
            420                 425                 430

His Gly Thr Met Asp Thr Glu Ser Lys Lys Asp Pro Glu Gly Cys Asp
            435                 440                 445

Lys Ser Asp Asp Lys Asn Thr Val Asn Leu Phe Gly Lys Val Ile Glu
            450                 455                 460

Thr Thr Glu Gln Asp Gln Glu Pro Ser Glu Ala Thr Val Gly Asn Gly
465                 470                 475                 480

Glu Val Thr Leu Thr Tyr Ala Thr Gly Thr Lys Glu Glu Ser Ala Gly
            485                 490                 495

Val Gln Asp Asn Leu Phe Leu Glu Lys Ala Met Gln Leu Ala Lys Arg
            500                 505                 510

His Ala Asn Ala Leu Phe Asp Tyr Ala Val Thr Gly Asp Val Lys Met
            515                 520                 525

Leu Leu Ala Val Gln Arg His Leu Thr Ala Val Gln Asp Glu Asn Gly
530                 535                 540

Asp Ser Val Leu His Leu Ala Ile Ile His Leu His Ser Gln Leu Val
545                 550                 555                 560

Arg Asp Leu Leu Glu Val Thr Ser Gly Leu Ile Ser Asp Asp Ile Ile
            565                 570                 575

Asn Met Arg Asn Asp Leu Tyr Gln Thr Pro Leu His Leu Ala Val Ile
            580                 585                 590

Thr Lys Gln Glu Asp Val Val Glu Asp Leu Leu Arg Ala Gly Ala Asp
            595                 600                 605

Leu Ser Leu Leu Asp Arg Leu Gly Asn Ser Val Leu His Leu Ala Ala
            610                 615                 620

Lys Glu Gly His Asp Lys Val Leu Ser Ile Leu Leu Lys His Lys Lys
625                 630                 635                 640

Ala Ala Leu Leu Leu Asp His Pro Asn Gly Asp Gly Leu Asn Ala Ile
            645                 650                 655

His Leu Ala Met Met Ser Asn Ser Leu Pro Cys Leu Leu Leu Leu Val
            660                 665                 670

Ala Ala Gly Ala Asp Val Asn Ala Gln Glu Gln Lys Ser Gly Arg Thr
            675                 680                 685

Ala Leu His Leu Ala Val Glu His Asp Asn Ile Ser Leu Ala Gly Cys
            690                 695                 700

Leu Leu Leu Glu Gly Asp Ala His Val Asp Ser Thr Thr Tyr Asp Gly
705                 710                 715                 720

Thr Thr Pro Leu His Ile Ala Ala Gly Arg Gly Ser Thr Arg Leu Ala
            725                 730                 735

Ala Leu Leu Lys Ala Ala Gly Ala Asp Pro Leu Val Glu Asn Phe Glu
            740                 745                 750

Pro Leu Tyr Asp Leu Asp Asp Ser Trp Glu Asn Ala Gly Glu Asp Glu
            755                 760                 765

Gly Val Val Pro Gly Thr Thr Pro Leu Asp Met Ala Thr Ser Trp Gln
770                 775                 780

Val Phe Asp Ile Leu Asn Gly Lys Pro Tyr Glu Pro Glu Phe Thr Ser
785                 790                 795                 800

Asp Asp Leu Leu Ala Gln Gly Asp Met Lys Gln Leu Ala Glu Asp Val
            805                 810                 815

Lys Leu Gln Leu Tyr Lys Leu Leu Glu Ile Pro Asp Pro Asp Lys Asn
            820                 825                 830
```

```
Trp Ala Thr Leu Ala Gln Lys Leu Gly Leu Gly Ile Leu Asn Asn Ala
        835                 840                 845

Phe Arg Leu Ser Pro Ala Pro Ser Lys Thr Leu Met Asp Asn Tyr Glu
    850                 855                 860

Val Ser Gly Gly Thr Val Arg Glu Leu Val Glu Ala Leu Arg Gln Met
865                 870                 875                 880

Gly Tyr Thr Glu Ala Ile Glu Val Ile Gln Ala Ala Ser Ser Pro Val
                885                 890                 895

Lys Thr Thr Ser Gln Ala His Ser Leu Pro Leu Ser Pro Ala Ser Thr
            900                 905                 910

Arg Gln Gln Ile Asp Glu Leu Arg Asp Ser Asp Ser Val Cys Asp Thr
            915                 920                 925

Gly Val Glu Thr Ser Phe Arg Lys Leu Ser Phe Thr Glu Ser Leu Thr
        930                 935                 940

Ser Gly Ala Ser Leu Leu Thr Leu Asn Lys Met Pro His Asp Tyr Gly
945                 950                 955                 960

Gln Glu Gly Pro Leu Glu Gly Lys Ile
                965
```

<210> SEQ ID NO 40
<211> LENGTH: 96
<212> TYPE: DNA
<213> ORGANISM: Artificial Sequence
<220> FEATURE:
<223> OTHER INFORMATION: engineered regulatory sequence

<400> SEQUENCE: 40
gctagccccg ccccgttgac gcaaatgggc ggtaggcgtg tacggtggga ggtttatata    60
agcagagctc gtttagtgaa ccgtcagatc agatct    96

<210> SEQ ID NO 41
<211> LENGTH: 154
<212> TYPE: DNA
<213> ORGANISM: Artificial Sequence
<220> FEATURE:
<223> OTHER INFORMATION: engineered regulatory sequence

<400> SEQUENCE: 41
gctagcgccc aaattgggat tttccaaaaa gccgaaattg ggattttcca aaaaccgccg    60
atcgcccgcc ccgttgacgc aaatgggcgg taggcgtgta cggtgggagg tttatataag   120
cagagctcgt ttagtgaacc gtcagatcag atct    154

<210> SEQ ID NO 42
<211> LENGTH: 212
<212> TYPE: DNA
<213> ORGANISM: Artificial Sequence
<220> FEATURE:
<223> OTHER INFORMATION: engineered regulatory sequence

<400> SEQUENCE: 42
acgcgtgccc aaattgggat tttccaaaaa gccgaaattg ggattttcca aaaaccgcgc    60
tagcgcccaa attgggattt tccaaaaagc cgaaattggg attttccaaa accgccgat    120 cgcccgcccc gttgacgcaa atgggcggta ggcgtgtacg gtgggaggtt tataagca    180 gagctcgttt agtgaaccgt cagatcagat ct    212

<210> SEQ ID NO 43
<211> LENGTH: 96
<212> TYPE: DNA

```
<213> ORGANISM: Artificial Sequence
<220> FEATURE:
<223> OTHER INFORMATION: engineered regulatory sequence

<400> SEQUENCE: 43
gctagccccg ccccgttgac gcaaatgggc ggtaggcgtg tacggtggga ggtctatata    60
agcagagctc gtttagtgaa ccgtcagatc agatct                              96

<210> SEQ ID NO 44
<211> LENGTH: 154
<212> TYPE: DNA
<213> ORGANISM: Artificial Sequence
<220> FEATURE:
<223> OTHER INFORMATION: engineered regulatory sequence

<400> SEQUENCE: 44
gctagcgccc aggtcgggat tttccgagga gccgaggtcg ggattttccg aggaccgccg    60
atcgcccgcc ccgttgacgc aaatgggcgg taggcgtgta cggtgggagg cctatataag   120
cagagctcgt ttagtgaacc gtcagatcag atct                               154

<210> SEQ ID NO 45
<211> LENGTH: 154
<212> TYPE: DNA
<213> ORGANISM: Artificial Sequence
<220> FEATURE:
<223> OTHER INFORMATION: engineered regulatory sequence

<400> SEQUENCE: 45
gctagcgccc aggtcgggat tttccgagga gccgaggtcg ggattttccg aggaccgccg    60
atcgcccgcc ccgttgacgc aaatgggcgg taggcgtgta cggtgggagg cctatataag   120
cagagctcgt ttagtgaacc gtcagatcag atct                               154

<210> SEQ ID NO 46
<211> LENGTH: 762
<212> TYPE: DNA
<213> ORGANISM: Artificial Sequence
<220> FEATURE:
<223> OTHER INFORMATION: engineered promoter construct

<400> SEQUENCE: 46
ggtacctcaa tattggccat tagccatatt attcattggt tatatagcat aaattaatat    60
tggctattgg ccattgcata cgttgtatct atatcataat atgtacattt atattggctc   120
atgtccaata tgaccgccat gttggcattg attattgact agttattaat agtaatcaat   180 tacgggtca ttagttcata gcccatatat ggagttccgc gttacataac ttacggtaaa   240
tggcccgcct ggctgaccgc ccaacgaccc ccgcccattg acgtcaataa tgacgtatgt   300
tcccatagta acgcaaatag ggattttcca ttaacgtcaa tgggtggagt atttacggta   360
aactgcccac ttggcagtac atcaagtgta tcatatgcca gtccgcccc ctattgacgt   420 caatgacggt aaatggcccg cctggcatta tgcccagtac atgactttat gggattttcc   480
tatttggcag tacatctacg tattagtcat cgctattacc atggtgatgc ggttttggca   540
gtacaccaat gggcgtggat agcggtttga ctcacgggga tttccaagtc tccacccat   600 tgacgtcaat gggagtttgt tttggcacca aggtaaaagg gattttccaa aatgtcgtaa   660
caactgcgat cgcccgcccc gttgacgcaa atgggcggta ggcgtgtacg gtgggaggtt   720
tatataagca gagctcgttt agtgaaccgt cagatcaagc tt                     762
```

<210> SEQ ID NO 47
<211> LENGTH: 762
<212> TYPE: DNA
<213> ORGANISM: Artificial Sequence
<220> FEATURE:
<223> OTHER INFORMATION: engineered promoter construct

<400> SEQUENCE: 47

| | | | | | |
|---|---|---|---|---|---|
| ggtacctcaa | tattggccat | tagccatatt | attcattggt | tatatagcat | aaattaatat | 60 |
| tggctattgg | ccattgcata | cgttgtatct | atatcataat | atgtacattt | atattggctc | 120 |
| atgtccaata | tgaccgccat | gttggcattg | attattgact | agttattaat | agtaatcaat | 180 |
| tacgggtca | ttagttcata | gcccatatat | ggagttccgc | gttacataac | ttacggtaaa | 240 |
| tggcccgcct | ggctgaccgc | ccaacgaccc | ccgcccattg | acgtcaataa | tgacgtatgt | 300 |
| tcccatagta | acgcaaatat | tcccgggaaa | ttaacgtcaa | tgggtggagt | atttacggta | 360 |
| aactgcccac | ttggcagtac | atcaagtgta | tcatatgcca | agtccgcccc | ctattgacgt | 420 |
| caatgacggt | aaatggcccg | cctggcatta | tgcccagtac | atgactttat | tctcgaggaa | 480 |
| tatttggcag | tacatctacg | tattagtcat | cgctattacc | atggtgatgc | ggttttggca | 540 |
| gtacaccaat | gggcgtggat | agcggtttga | ctcacgggga | tttccaagtc | tccaccccat | 600 |
| tgacgtcaat | gggagtttgt | tttggcacca | aggtaaaatt | acgcgtaaaa | aatgtcgtaa | 660 |
| caactgcgat | cgcccgcccc | gttgacgcaa | atgggcggta | ggcgtgtacg | gtgggaggtt | 720 |
| gctagccgca | gagctcgttt | agtgaaccgt | cagatcaagc | tt | | 762 |

<210> SEQ ID NO 48
<211> LENGTH: 762
<212> TYPE: DNA
<213> ORGANISM: Artificial Sequence
<220> FEATURE:
<223> OTHER INFORMATION: engineered promoter construct

<400> SEQUENCE: 48

| | | | | | |
|---|---|---|---|---|---|
| ggtacctcaa | tattggccat | tagccatatt | attcattggt | tatatagcat | aaatcaatat | 60 |
| tggctattgg | ccattgcata | cgttgtatct | atatcataat | atgtacattt | atattggctc | 120 |
| atgtccaata | tgaccgccat | gttggcattg | attattgact | agttattaat | agtaatcaat | 180 |
| tacgggtca | ttagttcata | gcccatatat | ggagttccgc | gttacataac | ttacggtaaa | 240 |
| tggcccgcct | ggctgaccgc | ccaacgaccc | ccgcccattg | acgtcaataa | tgacgtatgt | 300 |
| tcccatagta | acgccaatag | ggactttcca | ttgacgtcaa | tgggtggagt | atttacggta | 360 |
| aactgcccac | ttggcagtac | atcaagtgta | tcatatgcca | agtccgcccc | ctattgacgt | 420 |
| caatgacggt | aaatggcccg | cctggcatta | tgcccagtac | atgaccttac | gggactttcc | 480 |
| tacttggcag | tacatctacg | tattagtcat | cgctattacc | atggtgatgc | ggttttggca | 540 |
| gtacaccaat | gggcgtggat | agcggtttga | ctcacgggga | tttccaagtc | tccaccccat | 600 |
| tgacgtcaat | gggagtttgt | tttggcacca | aaatcaacgg | gactttccaa | aatgtcgtaa | 660 |
| caactgcgat | cgcccgcccc | gttgacgcaa | atgggcggta | ggcgtgtacg | gtgggaggtc | 720 |
| tatataagca | gagctcgttt | agtgaaccgt | cagatcaagc | tt | | 762 |

<210> SEQ ID NO 49
<211> LENGTH: 12
<212> TYPE: DNA
<213> ORGANISM: Artificial Sequence
<220> FEATURE:
<223> OTHER INFORMATION: wild type regulatory sequence

```
<400> SEQUENCE: 49
gactgtttgt tt                                                    12

<210> SEQ ID NO 50
<211> LENGTH: 12
<212> TYPE: DNA
<213> ORGANISM: Artificial Sequence
<220> FEATURE:
<223> OTHER INFORMATION: wild type regulatory sequence

<400> SEQUENCE: 50
aggactcttg ga                                                    12

<210> SEQ ID NO 51
<211> LENGTH: 46
<212> TYPE: DNA
<213> ORGANISM: Artificial Sequence
<220> FEATURE:
<223> OTHER INFORMATION: wild type regulatory sequence

<400> SEQUENCE: 51
tactaggagg ctgtaggcat aaattggtct gcgcaccagc accatg               46

<210> SEQ ID NO 52
<211> LENGTH: 46
<212> TYPE: DNA
<213> ORGANISM: Artificial Sequence
<220> FEATURE:
<223> OTHER INFORMATION: engineered regulatory sequence

<400> SEQUENCE: 52
tactaggagg ctgtaggcat aaattagtct gcgcaccagc accatg               46

<210> SEQ ID NO 53
<211> LENGTH: 46
<212> TYPE: DNA
<213> ORGANISM: Artificial Sequence
<220> FEATURE:
<223> OTHER INFORMATION: engineered regulatory sequence

<400> SEQUENCE: 53
tactaggatt agtgcttaag cccttggtct gcgcaccagc accatg               46

<210> SEQ ID NO 54
<211> LENGTH: 46
<212> TYPE: DNA
<213> ORGANISM: Artificial Sequence
<220> FEATURE:
<223> OTHER INFORMATION: engineered regulatory sequence

<400> SEQUENCE: 54
tactaggagg ctgtaggcat aaagctcgag tatacaacgc accatg               46

<210> SEQ ID NO 55
<211> LENGTH: 50
<212> TYPE: DNA
<213> ORGANISM: Artificial Sequence
<220> FEATURE:
<223> OTHER INFORMATION: engineered regulatory sequence

<400> SEQUENCE: 55
tactaggagg ctgtaggcat aaatgcgtaa aagcaccagc accatgcaac           50

<210> SEQ ID NO 56
<211> LENGTH: 50
```

```
<212> TYPE: DNA
<213> ORGANISM: Artificial Sequence
<220> FEATURE:
<223> OTHER INFORMATION: engineered regulatory sequence

<400> SEQUENCE: 56
tactaggagg ctgtaggcat aaattaaaaa acgcaccagc accatgcaac              50

<210> SEQ ID NO 57
<211> LENGTH: 50
<212> TYPE: DNA
<213> ORGANISM: Artificial Sequence
<220> FEATURE:
<223> OTHER INFORMATION: engineered regulatory sequence

<400> SEQUENCE: 57
tactaggagg ctgtaggcat aaattaatcc gcgcaccagc accatgcaac              50

<210> SEQ ID NO 58
<211> LENGTH: 51
<212> TYPE: DNA
<213> ORGANISM: Artificial Sequence
<220> FEATURE:
<223> OTHER INFORMATION: engineered regulatory sequence

<400> SEQUENCE: 58
accttgaggc atacttcaaa gactgttgat ttagcgaata agaggagttg g            51

<210> SEQ ID NO 59
<211> LENGTH: 51
<212> TYPE: DNA
<213> ORGANISM: Artificial Sequence
<220> FEATURE:
<223> OTHER INFORMATION: engineered regulatory sequence

<400> SEQUENCE: 59
accttgaggc atacttcaaa gactgtttat tttaataacg ggaggagttg g            51

<210> SEQ ID NO 60
<211> LENGTH: 51
<212> TYPE: DNA
<213> ORGANISM: Artificial Sequence
<220> FEATURE:
<223> OTHER INFORMATION: engineered regulatory sequence

<400> SEQUENCE: 60
accttgaggc atacttcaaa gactgtttat ttaaggactg ggaggagttg g            51

<210> SEQ ID NO 61
<211> LENGTH: 6513
<212> TYPE: DNA
<213> ORGANISM: Artificial Sequence
<220> FEATURE:
<223> OTHER INFORMATION: heterologous nucleic acid construct

<400> SEQUENCE: 61
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca taacttacgg taaatggccc   240
gcctggctga ccgcccaacg accccgccc attgacgtca ataatgacgt atgttcccat   300
agtaacgcca atagggactt tccattgacg tcaatgggtg gagtatttac ggtaaactgc   360
```

| | |
|---|---|
| ccacttggca gtacatcaag tgtatcatat gccaagtccg ccccctattg acgtcaatga | 420 |
| cggtaaatgg cccgcctggc attatgccca gtacatgacc ttacgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca agtctccacc ccattgacgt | 600 |
| caatgggagt ttgttttggc accaaaatca acgggacttt ccaaaatgtc gtaacaactg | 660 |
| cgatcgcccg ccccgttgac gcaaatgggc ggtaggcgtg tacggtggga ggtctatata | 720 |
| agcagagctc gtttagtgaa ccgtcagatc actagaagct ttattgcggt agtttatcac | 780 |
| agttaaattg ctaacgcagt cagtgcttct gacacaacag tctcgaactt aagctgcagt | 840 |
| gactctctta aggtagcctt gcagaagttg gtcgtgaggc actgggcagg taagtatcaa | 900 |
| ggttacaaga caggtttaag gagaccaata gaaactgggc ttgtcgagac agagaagact | 960 |
| cttgcgtttc tgataggcac ctattggtct tactgacatc cactttgcct ttctctccac | 1020 |
| aggtgtccac tcccagttca attacagctc ttaaggctag agtacttaat acgactcact | 1080 |
| ataggctagc cagcttgaag caagcctcct gaaagatgga ggcgtcgctg ccggcccagg | 1140 |
| ccgccgagac ggaggaggtg ggtcttttcg tcgaaaaata cctccggtcc gatgtcgcgc | 1200 |
| cggcggaaat tgtcgcgctc atgcgcaacc tcaacagcct gatgggacgc acgcggttta | 1260 |
| tttacctggc gttgctggag gcctgtctcc gcgttcccat ggccacccgc agcagcgcca | 1320 |
| tatttcggcg gatctatgac cactacgcca cgggcgtcat ccccacgatc aacgtcaccg | 1380 |
| gagagctgga gctcgtggcc ctgcccccca ccctgaacgt aaccccgtc tgggagctgt | 1440 |
| tgtgcctgtg cagcaccatg gccgcgcgcc tgcattggga ctcggcggcc ggggatctg | 1500 |
| ggaggacctt cggccccgat gacgtgctgg acctactgac cccccactac gaccgctaca | 1560 |
| tgcagctggt gttcgaactg ggccactgta acgtaaccga cggacttctg ctctcggagg | 1620 |
| aagccgtcaa gcgcgtcgcc gacgcccaa gcggctgtcc cccgcgcggg tccgttagcg | 1680 |
| agacggacca cgcggtggcg ctgttcaaga taatctgggg cgaactgttt ggcgtgcaga | 1740 |
| tggccaaaag cacgcagacg tttcccgggg cggggcgcgt taaaaacctc accaaacaga | 1800 |
| caatcgtggg gttgttggac gcccaccaca tcgaccacag cgcctgccgg acccacaggc | 1860 |
| agctgtacgc cctgcttatg gcccacaagc gggagtttgc gggcgcgcgc ttcaagctac | 1920 |
| gcgtgcccgc gtgggggcgc tgtttgcgca cgcactcatc cagcgccaac cccaacgctg | 1980 |
| acatcatcct ggaggcggcg ctgtcggagc tccccaccga ggcctggccc atgatgcagg | 2040 |
| gggcggtgaa ctttagcacc ctaatgaagc tactgtcttc tatcgaacaa gcatgcccaa | 2100 |
| aaaagaagag aaaggtagat gaattcccgg ggatctcgac ggcccccccg accgatgtca | 2160 |
| gcctggggga cgagctccac ttagacgcg aggacgtggc gatggcgcat gccgacgcgc | 2220 |
| tagacgattt cgatctggac atgttggggg acgggattc cccgggtccg ggatcgccag | 2280 |
| ggatccgtcg acttgacgcg ttgatatcat ctagagcggc cgcaggtacc tgaataacta | 2340 |
| aggccgcttc cctttagtga gggttaatgc ttcgagcaga catgataaga tacattgatg | 2400 |
| agtttggaca aaccacaact agaatgcagt gaaaaaaatg ctttatttgt gaaatttgtg | 2460 |
| atgctattgc tttatttgta accattataa gctgcaataa acaagttaac aacaacaatt | 2520 |
| gcattcattt tatgtttcag gttcagggg agatgtggga ggttttttaa agcaagtaaa | 2580 |
| acctctacaa atgtggtaaa atccgataag gatcgattcc ggagcctgaa tggcgaatgg | 2640 |
| acgcgccctg tagcggcgca ttaagcgcgg cgggtgtggt ggttacgcgc acgtgaccgc | 2700 |
| tacacttgcc agcgccctag cgcccgctcc tttcgctttc ttcccttcct ttctcgccac | 2760 |

```
gttcgccggc tttccccgtc aagctctaaa tcggggcctc cctttagggt tccgatttag    2820
tgctttacgg cacctcgacc ccaaaaaact tgattagggt gatggttcac gtagtgggcc    2880
atcgccctga tagacggttt ttcgcccttt gacgttggag tccacgttct ttaatagtgg    2940
actcttgttc caaactggaa caacactcaa ccctatctcg gtctattctt ttgatttata    3000
agggattttg ccgatttcgg cctattggtt aaaaaatgag ctgatttaac aaaaatttaa    3060
cgcgaatttt aacaaaatat taacgcttac aatttcgcct gtgtaccttc tgaggcggaa    3120
agaaccagct gtggaatgtg tgtcagttag ggtgtggaaa gtccccaggc tccccagcag    3180
gcagaagtat gcaaagcatg catctcaatt agtcagcaac caggtgtgga aagtccccag    3240
gctccccagc aggcagaagt atgcaaagca tgcatctcaa ttagtcagca accatagtcc    3300
cgcccctaac tccgcccatc ccgcccctaa ctccgcccag ttccgcccat tctccgcccc    3360
atggctgact aattttttt atttatgcag aggccgaggc cgcctcggcc tctgagctat    3420
tccagaagta gtgaggaggc ttttttggag gcctaggctt ttgcaaaaag cttgattctt    3480
ctgacacaac agtctcgaac ttaaggctag agccaccatg attgaacaag atggattgca    3540
cgcaggttct ccggccgctt gggtggagag gctattcggc tatgactggg cacaacagac    3600
aatcggctgc tctgatgccg ccgtgttccg gctgtcagcg caggggcgcc cggttctttt    3660
tgtcaagacc gacctgtccg gtgccctgaa tgaactgcag gacgaggcag cgcggctatc    3720
gtggctggcc acgacgggcg ttccttgcgc agctgtgctc gacgttgtca ctgaagcggg    3780
aagggactgg ctgctattgg gcgaagtgcc ggggcaggat ctcctgtcat ctcaccttgc    3840
tcctgccgag aaagtatcca tcatggctga tgcaatgcgg cggctgcata cgcttgatcc    3900
ggctacctgc ccattcgacc accaagcgaa acatcgcatc gagcgagcac gtactcggat    3960
ggaagccggt cttgtcgatc aggatgatct ggacgaagag catcaggggc tcgcgccagc    4020
cgaactgttc gccaggctca aggcgcgcat gcccgacggc gaggatctcg tcgtgaccca    4080
tggcgatgcc tgcttgccga atatcatggt ggaaaatggc cgcttttctg gattcatcga    4140
ctgtggccgg ctgggtgtgg cggaccgcta tcaggacata gcgttggcta cccgtgatat    4200
tgctgaagag cttggcggcg aatgggctga ccgcttcctc gtgctttacg gtatcgccgc    4260
tcccgattcg cagcgcatcg ccttctatcg ccttcttgac gagttcttct gagcgggact    4320
ctggggttcg aaatgaccga ccaagcgacg cccaacctgc catcacgatg gccgcaataa    4380
aatatcttta ttttcattac atctgtgtgt tggttttttg tgtgaagatc cgcgtatggt    4440
gcactctcag tacaatctgc tctgatgccg catagttaag ccagccccga cacccgccaa    4500
cacccgctga cgcgccctga cgggcttgtc tgctcccggc atccgcttac agacaagctg    4560
tgaccgtctc cgggagctgc atgtgtcaga ggttttcacc gtcatcaccg aaacgcgcga    4620
gacgaaaggg cctcgtgata cgcctatttt tataggttaa tgtcatgata taatggtttc    4680
cttagacgtc aggtggcact tttcggggaa atgtgcgcgg aacccctatt tgtttatttt    4740
tctaaataca ttcaaatatg tatccgctca tgagacaata accctgataa atgcttcaat    4800
aatattgaaa aaggaagagt atgagtattc aacatttccg tgtcgccctt attcccttt    4860 ttgcggcatt ttgccttcct gttttgctc acccagaaac gctggtgaaa gtaaaagatg    4920
ctgaagatca gttgggtgca cgagtgggtt acatcgaact ggatctcaac agcggtaaga    4980
tccttgagag ttttcgcccc gaagaacgtt ttccaatgat gagcactttt aaagttctgc    5040
tatgtggcgc ggtattatcc cgtattgacg ccgggcaaga gcaactcggt cgccgcatac    5100
```

```
actattctca gaatgacttg gttgagtact caccagtcac agaaaagcat cttacggatg    5160
gcatgacagt aagagaatta tgcagtgctg ccataaccat gagtgataac actgcggcca    5220
acttacttct gacaacgatc ggaggaccga aggagctaac cgcttttttg cacaacatgg    5280
gggatcatgt aactcgcctt gatcgttggg aaccggagct gaatgaagcc ataccaaacg    5340
acgagcgtga caccacgatg cctgtagcaa tggcaacaac gttgcgcaaa ctattaactg    5400
gcgaactact tactctagct tcccggcaac aattaataga ctggatggag gcggataaag    5460
ttgcaggacc acttctgcgc tcggcccttc cggctggctg gtttattgct gataaatctg    5520
gagccggtga gcgtgggtct cgcggtatca ttgcagcact ggggccagat ggtaagccct    5580
cccgtatcgt agttatctac acgacgggga gtcaggcaac tatggatgaa cgaaatagac    5640
agatcgctga gataggtgcc tcactgatta agcattggta actgtcagac caagtttact    5700
catatatact ttagattgat ttaaaacttc attttaatt taaaaggatc taggtgaaga    5760
tcctttttga taatctcatg accaaaatcc cttaacgtga gttttcgttc cactgagcgt    5820
cagaccccgt agaaaagatc aaaggatctt cttgagatcc ttttttctg cgcgtaatct    5880 gctgcttgca acaaaaaaa ccaccgctac cagcggtggt ttgtttgccg gatcaagagc    5940
taccaactct ttttccgaag gtaactggct tcagcagagc gcagatacca aatactgtcc    6000
ttctagtgta gccgtagtta ggccaccact tcaagaactc tgtagcaccg cctacatacc    6060
tcgctctgct aatcctgtta ccagtggctg ctgccagtgg cgataagtcg tgtcttaccg    6120
ggttggactc aagacgatag ttaccggata aggcgcagcg tcgggctga acggggggtt    6180 cgtgcacaca gcccagcttg gagcgaacga cctacaccga actgagatac ctacagcgtg    6240
agctatgaga aagcgccacg cttcccgaag ggagaaaggc ggacaggtat ccggtaagcg    6300
gcagggtcgg aacaggagag cgcacgaggg agcttccagg gggaaacgcc tggtatcttt    6360
atagtcctgt cgggtttcgc cacctctgac ttgagcgtcg attttgtga tgctcgtcag    6420 ggggcggag cctatggaaa aacgccagca acgcggcctt tttacggttc ctggccttt    6480 gctggccttt tgctcacatg gctcgacaga tct                                6513
```

<210> SEQ ID NO 62
<211> LENGTH: 6439
<212> TYPE: DNA
<213> ORGANISM: Artificial Sequence
<220> FEATURE:
<223> OTHER INFORMATION: heterologous nucleic acid construct

<400> SEQUENCE: 62

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg accccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccctattg acgtcaatga    420 cggtaaatgg cccgcctggc attatgccca gtacatgacc ttcgggact tcctacttg    480 gcagtacatc tacgtattag tcatcgctat taccatggtg atgcggtttt ggcagtacac    540
caatgggcgt ggatagcggt ttgactcacg gggatttcca gtctccacc ccattgacgt    600 caatgggagt ttgttttggc accaaaatca acgggacttt ccaaaatgtc gtaacaactg    660
```

```
                                                              -continued cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc cagcttgaag caagcctcct gaaagatgga ggcgtcgctg ccggcccagg   1140
ccgccgagac ggaggaggtg ggtcttttcg tcgaaaaata cctccggtcc gatgtcgcgc   1200
cggcggaaat tgtcgcgctc atgcgcaacc tcaacagcct gatgggacgc acgcggttta   1260
tttacctggc gttgctggag gcctgtctcc gcgttccat ggccacccgc agcagcgcca   1320
tatttcggcg gatctatgac cactacgcca cgggcgtcat ccccacgatc aacgtcaccg   1380
gagagctgga gctcgtggcc ctgccccca ccctgaacgt aaccccgtc tgggagctgt   1440 tgtgcctgtg cagcaccatg gccgcgcgcc tgcattggga ctcggcggcc ggggatctg   1500 ggaggacctt cggccccgat gacgtgctgg acctactgac cccccactac gaccgctaca   1560
tgcagctggt gttcgaactg ggccactgta acgtaaccga cggacttctg ctctcggagg   1620
aagccgtcaa gcgcgtcgcc gacgccctaa gcggctgtcc cccgcgcggg tccgttagcg   1680
agacggacca cgcggtggcg ctgttcaaga taatctgggg cgaactgttt ggcgtgcaga   1740
tggccaaaag cacgcagacg tttcccgggg cggggcgcgt taaaaacctc accaaacaga   1800
caatcgtggg gttgttggac gcccaccaca tcgaccacag cgcctgccgg acccacaggc   1860
agctgtacgc cctgcttatg gcccacaagc gggagtttgc gggcgcgcgc ttcaagctac   1920
gcgtgcccgc gtggggcgc tgtttgcgca cgcactcatc cagcgccaac cccaacgctg   1980
acatcatcct ggaggcggcg ctgtcggagc tccccaccga ggcctggccc atgatgcagg   2040
gggcggtgaa ctttagcacc ctaccaaaaa agaagagaaa ggtagatcgg acactggtga   2100
ccttcaagga tgtatttgtg gacttcacca gggaggagtg gaagctgctg gacactgctc   2160
agcagatcgt gtacagaaat gtgatgctgg agaactataa gaacctggtt tccttgggtt   2220
attgatgaga tatcatctag agcggccgca ggtacctgaa taactaaggc cgcttccctt   2280

tagtgagggt taatgcttcg agcagacatg ataagataca ttgatgagtt tggacaaacc   2340
acaactagaa tgcagtgaaa aaaatgcttt aттттgтgaaa tttgtgatgc tattgcttta   2400

tttgtaacca ttataagctg caataaacaa gttaacaaca acaattgcat tcattttatg   2460

tttcaggttc agggggagat gtgggaggtt ttttaaagca agtaaaacct ctacaaatgt   2520
ggtaaaatcc gataaggatc gattccggag cctgaatggc gaatgacgc gccctgtagc   2580 ggcgcattaa gcgcggcggg tgtggtggtt acgcgcacgt gaccgctaca cttgccagcg   2640
ccctagcgcc cgctcctttc gctttcttcc cttcctttct cgccacgttc gccggctttc   2700
cccgtcaagc tctaaatcgg gggctccctt tagggttccg atttagtgct tacggcacc   2760

tcgaccccaa aaaacttgat tagggtgatg gttcacgtag tgggccatcg ccctgataga   2820
cggtttttcg ccctttgacg ttggagtcca cgttctttaa tagtggactc tgttccaaa   2880 ctggaacaac actcaaccct atctcggtct attcttttga tttataaggg attttgccga   2940

tttcggccta ttggttaaaa atgagctga tttaacaaaa atttaacgcg aattttaaca   3000
```

```
aaatattaac gcttacaatt tcgcctgtgt accttctgag gcggaaagaa ccagctgtgg    3060
aatgtgtgtc agttagggtg tggaaagtcc ccaggctccc cagcaggcag aagtatgcaa    3120
agcatgcatc tcaattagtc agcaaccagg tgtggaaagt ccccaggctc cccagcaggc    3180
agaagtatgc aaagcatgca tctcaattag tcagcaacca tagtcccgcc cctaactccg    3240
cccatcccgc ccctaactcc gcccagttcc gcccattctc cgccccatgg ctgactaatt    3300
ttttttattt atgcagaggc cgaggccgcc tcggcctctg agctattcca gaagtagtga    3360
ggaggctttt ttggaggcct aggcttttgc aaaaagcttg attcttctga cacaacagtc    3420
tcgaacttaa ggctagagcc accatgatta acaagatgg attgcacgca ggttctccgg     3480
ccgcttgggt ggagaggcta ttcggctatg actgggcaca acagacaatc ggctgctctg    3540
atgccgccgt gttccggctg tcagcgcagg ggcgcccggt tctttttgtc aagaccgacc    3600
tgtccggtgc cctgaatgaa ctgcaggacg aggcagcgcg gctatcgtgg ctggccacga    3660
cgggcgttcc ttgcgcagct gtgctcgacg ttgtcactga agcgggaagg gactggctgc    3720
tattgggcga agtgccgggg caggatctcc tgtcatctca ccttgctcct gccgagaaag    3780
tatccatcat ggctgatgca atgcggcggc tgcatacgct tgatccggct acctgcccat    3840
tcgaccacca agcgaaacat cgcatcgagc gagcacgtac tcggatggaa gccggtcttg    3900
tcgatcagga tgatctggac gaagagcatc agggctcgc gccagccgaa ctgttcgcca    3960
ggctcaaggc gcgcatgccc gacggcgagg atctcgtcgt gacccatggc gatgcctgct    4020
tgccgaatat catggtggaa aatggccgct tttctggatt catcgactgt ggccggctgg    4080
gtgtggcgga ccgctatcag gacatagcgt tggctacccg tgatattgct gaagagcttg    4140
gcggcgaatg ggctgaccgc ttcctcgtgc tttacggtat cgccgctccc gattcgcagc    4200
gcatcgcctt ctatcgcctt cttgacgagt tcttctgagc gggactctgg ggttcgaaat    4260
gaccgaccaa gcgacgccca acctgccatc acgatggccg caataaaata tctttatttt    4320
cattacatct gtgtgttggt tttttgtgtg aagatccgcg tatggtgcac tctcagtaca    4380
atctgctctg atgccgcata gttaagccag ccccgacacc cgccaacacc cgctgacgcg    4440
ccctgacggg cttgtctgct cccggcatcc gcttacagac aagctgtgac cgtctccggg    4500
agctgcatgt gtcagaggtt ttcaccgtca tcaccgaaac gcgcgagacg aaagggcctc    4560
gtgatacgcc tatttttata ggttaatgtc atgataataa tggtttctta cgtcaggt     4620 ggcacttttc ggggaaatgt gcgcggaacc cctatttgtt tatttttcta aatacattca    4680
aatatgtatc cgctcatgag acaataaccc tgataaatgc ttcaataata ttgaaaaagg    4740
aagagtatga gtattcaaca tttccgtgtc gcccttattc ccttttttgc ggcattttgc    4800
cttcctgttt ttgctcaccc agaaacgctg gtgaaagtaa aagatgctga agatcagttg    4860
ggtgcacgag tgggttacat cgaactggat ctcaacagcg gtaagatcct tgagagtttt    4920
cgccccgaag aacgttttcc aatgatgagc acttttaaag ttctgctatg tggcgcggta    4980
ttatcccgta ttgacgccgg gcaagagcaa ctcggtcgcc gcatacacta ttctcagaat    5040
gacttggttg agtactcacc agtcacagaa aagcatctta cggatggcat gacagtaaga    5100
gaattatgca gtgctgccat aaccatgagt gataacactg cggccaactt acttctgaca    5160
acgatcggag gaccgaagga gctaaccgct tttttgcaca acatggggga tcatgtaact    5220
cgccttgatc gttgggaacc ggagctgaat gaagccatac caaacgacga gcgtgacacc    5280
acgatgcctg tagcaatggc aacaacgttg cgcaaactat taactggcga actacttact    5340
ctagcttccc ggcaacaatt aatagactgg atggaggcgg ataaagttgc aggaccactt    5400
```

```
ctgcgctcgg cccttccggc tggctggttt attgctgata atctggagc cggtgagcgt      5460 gggtctcgcg gtatcattgc agcactgggg ccagatggta agccctcccg tatcgtagtt      5520
atctacacga cggggagtca ggcaactatg gatgaacgaa atagacagat cgctgagata      5580
ggtgcctcac tgattaagca ttggtaactg tcagaccaag tttactcata tatactttag      5640
attgatttaa aacttcattt ttaatttaaa aggatctagg tgaagatcct ttttgataat      5700
ctcatgacca aaatcccctta acgtgagttt tcgttccact gagcgtcaga ccccgtagaa      5760
aagatcaaag gatcttcttg agatccttt tttctgcgcg taatctgctg cttgcaaaca      5820 aaaaaccac cgctaccagc ggtggtttgt ttgccggatc aagagctacc aactcttttt      5880
ccgaaggtaa ctggcttcag cagagcgcag ataccaaata ctgtccttct agtgtagccg      5940
tagttaggcc accacttcaa gaactctgta gcaccgccta catacctcgc tctgctaatc      6000
ctgttaccag tggctgctgc cagtggcgat aagtcgtgtc ttaccgggtt ggactcaaga      6060
cgatagttac cggataaggc gcagcggtcg ggctgaacgg ggggttcgtg cacacagccc      6120
agcttggagc gaacgaccta caccgaactg agatacctac agcgtgagct atgagaaagc      6180
gccacgcttc ccgaagggag aaaggcggac aggtatccgg taagcggcag ggtcggaaca      6240
ggagagcgca cgagggagct tccaggggga aacgcctggt atctttatag tcctgtcggg      6300
tttcgccacc tctgacttga gcgtcgattt ttgtgatgct cgtcaggggg gcggagccta      6360
tggaaaaacg ccagcaacgc ggcctttta cggttcctgg cctttgctg gccttttgct      6420 cacatggctc gacagatct                                                  6439
```

<210> SEQ ID NO 63
<211> LENGTH: 77
<212> TYPE: PRT
<213> ORGANISM: Herpes simplex virus type 2

<400> SEQUENCE: 63

Thr Ala Pro Ile Thr Asp Val Ser Leu Gly Asp Glu Leu Arg Leu Asp
1               5                   10                  15

Gly Glu Glu Val Asp Met Thr Pro Ala Asp Ala Leu Asp Asp Phe Asp
                20                  25                  30

Leu Glu Met Leu Gly Asp Val Glu Ser Pro Ser Pro Gly Met Thr His
            35                  40                  45

Asp Pro Val Ser Tyr Gly Ala Leu Asp Val Asp Phe Glu Phe Glu
        50                  55                  60

Gln Met Phe Thr Asp Ala Leu Gly Ile Asp Asp Phe Gly
65                  70                  75

<210> SEQ ID NO 64
<211> LENGTH: 44
<212> TYPE: PRT
<213> ORGANISM: Herpes simplex virus type 2

<400> SEQUENCE: 64

Ala Asp Ala Leu Asp Asp Phe Asp Leu Glu Met Ala Asp Ala Leu Asp
1               5                   10                  15

Asp Phe Asp Leu Glu Met Ala Asp Ala Leu Asp Phe Asp Leu Glu
                20                  25                  30

Met Ala Asp Ala Leu Asp Asp Phe Asp Leu Glu Met
            35                  40

<210> SEQ ID NO 65

```
<211> LENGTH: 10
<212> TYPE: DNA
<213> ORGANISM: Artificial Sequence
<220> FEATURE:
<223> OTHER INFORMATION: engineered DNA response element

<400> SEQUENCE: 65
actttatttt                                                              10

<210> SEQ ID NO 66
<211> LENGTH: 10
<212> TYPE: DNA
<213> ORGANISM: Artificial Sequence
<220> FEATURE:
<223> OTHER INFORMATION: engineered DNA response element

<400> SEQUENCE: 66
gagttttcc                                                               10

<210> SEQ ID NO 67
<211> LENGTH: 10
<212> TYPE: DNA
<213> ORGANISM: Artificial Sequence
<220> FEATURE:
<223> OTHER INFORMATION: engineered DNA response element

<400> SEQUENCE: 67
gatgggattt                                                              10

<210> SEQ ID NO 68
<211> LENGTH: 10
<212> TYPE: DNA
<213> ORGANISM: Artificial Sequence
<220> FEATURE:
<223> OTHER INFORMATION: engineered DNA response element

<400> SEQUENCE: 68
tcttttgtt                                                               10

<210> SEQ ID NO 69
<211> LENGTH: 10
<212> TYPE: DNA
<213> ORGANISM: Artificial Sequence
<220> FEATURE:
<223> OTHER INFORMATION: engineered DNA response element

<400> SEQUENCE: 69
gagttggcgg                                                              10

<210> SEQ ID NO 70
<211> LENGTH: 10
<212> TYPE: DNA
<213> ORGANISM: Artificial Sequence
<220> FEATURE:
<223> OTHER INFORMATION: engineered DNA response element

<400> SEQUENCE: 70
tctggttgtt                                                              10

<210> SEQ ID NO 71
<211> LENGTH: 10
<212> TYPE: DNA
<213> ORGANISM: Artificial Sequence
<220> FEATURE:
<223> OTHER INFORMATION: engineered DNA response element

<400> SEQUENCE: 71
```

-continued gagttttgtt                                                              10

<210> SEQ ID NO 72
<211> LENGTH: 12
<212> TYPE: DNA
<213> ORGANISM: Artificial Sequence
<220> FEATURE:
<223> OTHER INFORMATION: engineered DNA response element

<400> SEQUENCE: 72
ccagggcccc ga                                                           12

<210> SEQ ID NO 73
<211> LENGTH: 12
<212> TYPE: DNA
<213> ORGANISM: Artificial Sequence
<220> FEATURE:
<223> OTHER INFORMATION: engineered DNA response element

<400> SEQUENCE: 73
gccgcggtct gt                                                           12

<210> SEQ ID NO 74
<211> LENGTH: 12
<212> TYPE: DNA
<213> ORGANISM: Artificial Sequence
<220> FEATURE:
<223> OTHER INFORMATION: engineered DNA response element

<400> SEQUENCE: 74
cgtccgcggt ga                                                           12

<210> SEQ ID NO 75
<211> LENGTH: 12
<212> TYPE: DNA
<213> ORGANISM: Artificial Sequence
<220> FEATURE:
<223> OTHER INFORMATION: engineered DNA response element

<400> SEQUENCE: 75
tttacttatt tt                                                           12

<210> SEQ ID NO 76
<211> LENGTH: 7
<212> TYPE: DNA
<213> ORGANISM: Artificial Sequence
<220> FEATURE:
<223> OTHER INFORMATION: engineered DNA response element

<400> SEQUENCE: 76 gagtttt                                                                  7

<210> SEQ ID NO 77
<211> LENGTH: 9
<212> TYPE: DNA
<213> ORGANISM: Artificial Sequence
<220> FEATURE:
<223> OTHER INFORMATION: sequence complementary to SEQ ID No:33

<400> SEQUENCE: 77 aaaacttta                                                                9